United States Patent
Howley

(10) Patent No.: US 11,173,206 B2
(45) Date of Patent: Nov. 16, 2021

(54) IMMUNE MODULATION

(71) Applicant: SEMENTIS LIMITED, Berwick (AU)

(72) Inventor: Paul Michael Howley, Berwick (AU)

(73) Assignee: Sementis Limited, Berwick (AU)

( * ) Notice: Subject to any disclaimer, the term of this patent is extended or adjusted under 35 U.S.C. 154(b) by 782 days.

(21) Appl. No.: 14/777,457

(22) PCT Filed: Mar. 17, 2014

(86) PCT No.: PCT/AU2014/000286
§ 371 (c)(1),
(2) Date: Sep. 15, 2015

(87) PCT Pub. No.: WO2014/138824
PCT Pub. Date: Sep. 18, 2014

(65) Prior Publication Data
US 2016/0030552 A1    Feb. 4, 2016

Related U.S. Application Data

(60) Provisional application No. 61/852,239, filed on Mar. 15, 2013.

(51) Int. Cl.
*A61K 39/35* (2006.01)
*C12N 7/00* (2006.01)
*C12N 15/86* (2006.01)
*A61K 39/00* (2006.01)

(52) U.S. Cl.
CPC .......... *A61K 39/35* (2013.01); *C12N 7/00* (2013.01); *C12N 15/86* (2013.01); *A61K 2039/515* (2013.01); *A61K 2039/5154* (2013.01); *A61K 2039/572* (2013.01); *C07K 2319/95* (2013.01); *C12N 2710/24134* (2013.01); *C12N 2710/24142* (2013.01); *C12N 2710/24143* (2013.01); *C12N 2710/24171* (2013.01)

(58) Field of Classification Search
None
See application file for complete search history.

(56) References Cited

U.S. PATENT DOCUMENTS

| | | | | |
|---|---|---|---|---|
| 5,773,705 | A | 6/1998 | Vierstra et al. | 800/250 |
| 6,037,135 | A | 3/2000 | Kubo et al. | 435/7.24 |
| 2009/0191157 | A1* | 7/2009 | Albrecht | A61K 39/35 424/93.2 |
| 2009/0317389 | A1* | 12/2009 | Saxon | C07K 16/00 424/134.1 |

FOREIGN PATENT DOCUMENTS

| | | |
|---|---|---|
| JP | 2011-231112 A | 11/2011 |
| JP | 2016-513963 A | 5/2016 |
| WO | WO 2001/040264 | 6/2001 |
| WO | WO 2003/076591 | 9/2003 |
| WO | WO 2007/104581 | 9/2007 |
| WO | WO 2010/018378 | 2/2010 |
| WO | WO 2014/138824 | 9/2014 |

OTHER PUBLICATIONS

Metzler et al. 'Solution structure of~uman CTLA-4 and delineation of a CD80/CD86 binding site conserved in CD28.' Nature Structural Biol. 4:527-531, 1997.*
Bork et al. 'Powers and Pitfalls in Sequence Analysis: The 70% Hurdle.' Gen. Res. 10:398-400, 2000.*
Doerks et al. 'Protein annotation: detective work for function prediction.' Trends in Genetics. 14:248-250, 1998.*
Smith et al. The challenges of genome sequence annotation or "the devil is in the details". Nat. Biotech. 15:1222-1223, 1997.*
Brenner S. 'Errors in genome annotation.' Trends in Genetics 15:132-133, 1999.*
Bowie et al. Decipering the Message in Protein Sequences: Tolerance to Amino Acid Substitutions. Science 247:1306-1310, 1990.*
Hartl et al. 'DNA vaccines for allergy treatment.' Methods 32:328-339, 2004.*
Yu et al. 'Allergen-specific CD8+ T cells in peanut-allergic individuals.' vol. 143, Issue 5, pp. 1948-1952, 2019.*
Blumenthal et al. 'Definition of an Allergen.' Allergens and Allergen Immunotherapy. Ed. R Lockey, S. Bukantz and J. Bousquet. New York: Marcel Decker, 2004.37-50.*
Yu W, Zhou X, Davis MM, Nadeau KC, Regulation of peanut-specific CD8+T cells from nonallergic individuals., Journal of Allergy and Clinical Immunology (2020), doi: https://doi.org/10.1016/j.jaci.2020.07.032.*
Sampath et al. 'Newly identified T cell subsets in mechanistic studies of food immunotherapy.' J Clin Invest Apr. 1, 2019; 129(4):1431-1440. doi: 10.1172/JCI124605. Epub Apr. 1, 2019.*
Draghi et al. 'Different profile of CD8+ effectorT cells induced in Der p 1-allergic and naive mice by DNA vaccination.' Eur J Immunol. 2002;32:3720-3728.*
Letter/Written Disclosure of the Information Disclosure Statement for the above-referenced application, filed herewith on Dec. 9, 2015, 2 pages.
Albani et al., "DcE2F, a functional plant E2F-like transcriptional activator from Daucus carota," J. Biol. Chem. 275(25):19258-19267 (2000).

(Continued)

*Primary Examiner* — Nora M Rooney
(74) *Attorney, Agent, or Firm* — Dentons US LLP; Stephanie Seidman

(57) ABSTRACT

The present invention relates to a poxvirus vector comprising a nucleic acid sequence encoding a fusion protein comprising: (i) a peanut allergen selected from list consisting of at least two peanut allergens from ara h 1, ara h 2, ara h 3, ara h 4, ara h 5, ara h 6. ara h 7, ara h 8, ara h 9, ara h I O and ara h I I or a derivative or part thereof having at least 70% sequence identity thereto, and (ii) a profeasome degradation tag to enhance intracellular degradation of the fusion protein. Methods of desensitizing or inducing tolerance to a peanut allergen and/or suppressing an allergic response to a peanut allergen are also disclosed.

15 Claims, 17 Drawing Sheets
Specification includes a Sequence Listing.

(56) References Cited

OTHER PUBLICATIONS

Burks et al., "Identification and characterization of a second major peanut allergen, Ara h II, with use of the sera of patients with atopic dermatitis and positive peanut challenge," J. Allergy Clin. Immunol. 90(6):962-969 (1992).
Dai et al., "The basic helix-loop-helix factor, HAND2, functions as a transcriptional activator by binding to E-boxes as a heterodimer," J. Biol. Chem. 277(15):12604-12612 (2002).
DeLong et al., "Ara h 1-reactive T cells in individuals with peanut allergy," J. Allergy Clin. Immunol. 127 (5):1211-1218.e3 (2011).
DeVries et al. "Receptors and cytokines involved in allergic TH2 cell responses," J. Allergy Clin. Immunol. 103(5 Pt 2):S492-S496 (1999).
Dudek et al., "Replication-defective viruses as vaccines and vaccine vectors," Virology 344:230-239 (2006).
Flinterman et al., "Children with peanut allergy recognize predominantly Ara h2 and Ara h6, which remains stable over time," Clin Exp Allergy. 37(8):1221-1228 (2007).
Genbank Accession No. ACH91862, "arachin Arah3 isoform [Arachis hypogaea]," Published on Oct. 22, 2009 [online][retrieved on Dec. 1, 2015] Retrieved from: <URL:nbci.nlm.nih.gov/nuccore/ACH91862 [1 page].
Genbank Accession No. AF059616, "Arachis hypogaea profilin (Ara h 5) mRNA, complete cds," Published on Oct. 8, 1999 [online][retrieved on Nov. 11, 2015] Retrieved from: <URL:nbci.nlm.nih.gov/nuccore/AF059616 [1 page].
Genbank Accession No. AF086821, "Arachis hypogaea glycinin (Arah4) mRNA, complete cds," Published on Sep. 29, 1999 [online][retrieved on Nov. 11, 2015] Retrieved from: <URL:nbci.nlm.nih.gov/nuccore/AF086821[2 pages].
Genbank Accession No. AF091737, "Arachis hypogaea allergen (Ara h 7) mRNA, complete cds," Published on Oct. 8, 1999 [online][retrieved on Nov. 11, 2015] Retrieved from: <URL:nbci.nlm.nih.gov/nuccore/AF091737 [1 page].
Genbank Accession No. AF092846, "Arachis hypogaea allergen (Arah6 (Ara h 6) mRNA, partial cds," Published on Oct. 8, 1999 [online][retrieved on Nov. 11, 2015] Retrieved from: <URL:nbci.nlm.nih.gov/nuccore/AF092846 [1 page].
Genbank Accession No. AF093541, "Arachis hypogaea glycinin (Arah3) mRNA, partial cds," Published on Oct. 31, 2001 [online][retrieved on Dec. 1, 2015] Retrieved from: <URL:nbci.nlm.nih.gov/nuccore/AF093541 [2 pages].
Genbank Accession No. AY328088, "Arachis hypogaea allergen Ara h 8 mRNA, complete cds," Published on Feb. 8, 2005 [online][retrieved on Nov. 11, 2015] Retrieved from: <URL:nbci.nlm.nih.gov/nuccore/AY328088 [1 page].
Genbank Accession No. AY722694, "Arachis hypogaea oleosin 1 mRNA, complete cds," Published on Aug. 25, 2006 [online][retrieved on Nov. 11, 2015] Retrieved from: <URL:nbci.nlm.nih.gov/nuccore/AY722694 [1 page].
Genbank Accession No. AY722695, "Arachis hypogaea oleosin 2 mRNA, partial cds," Published on Sep. 19, 2004 [online][retrieved on Nov. 11, 2015] Retrieved from: <URL:nbci.nlm.nih.gov/nuccore/AY722695 [1 page].
Genbank Accession No. DQ097716, "Arachis hypogaea oleosin 1 mRNA, complete cds," Published in Jul. 25, 2005 [online][retrieved on Nov. 11, 2015] Retrieved from: <URL:nbci.nlm.nih.gov/nuccore/DQ097716 [1 page].
Genbank Accession No. EF436550, "Arachis hypogaea Ara h 8 allergen isoform mRNA, complete cds," Published on Feb. 12, 2008 [online] [retrieved on Nov. 11, 2015] Retrieved from: <URL:nbci.nlm.nih.gov/nuccore/EF436550 [1 page].
Genbank Accession No. EU159429, "Arachis hypogaea LTP isoallergen 1 precursor, mRNA, complete cds," Published on Oct. 7, 2009 [online][retrieved on Nov. 11, 2015] Retrieved from: <URL:nbci.nlm.nih.gov/nuccore/EU159429 [1 page].
Genbank Accession No. EU161278, "Arachis hypogaea LTP isoallergen 2 mRNA, partial cds," Published on Oct. 7, 2009 [online][retrieved on Nov. 11, 2015] Retrieved from: <URL:nbci.nlm.nih.gov/nuccore/EU161278 [1 page].
Genbank Accession No. L34402, "Arachis hypogaea (clone 941b) Ara h I mRNA, complete cds," Published on May 24, 1996 [online][retrieved on Dec. 1, 2015] Retrieved from: <URL:nbci.nlm.nih.gov/nuccore/L34402 [2 pages].
Genbank Accession No. L38853, "Arachis hypogaea (clone P17) Ara h 1 mRNA, complete cds," Published on Jan. 10, 1995 [online][retrieved on Dec. 1, 2015] Retrieved from: <URL:nbci.nlm.nih.gov/nuccore/L38853 [2 pages].
Genbank Accession No. NM_021009, "*Homo sapiens* ubiquitin C (UBC), mRNA," Published on Mar. 15, 2015 [online][retrieved on Nov. 11, 2015] Retrieved from: <URL:nbci.nlm.nih.gov/nuccore/NM_021009 [5 pages].
Hartl et al., "Characterization of the protective and therapeutic efficiency of a DNA vaccine encoding the major birch pollen allergen Bet v la," Allergy 59:65-73 (2004).
Hartl et al., "Immune responses after immunization with plasmid DNA encoding Bet v 1, the major allergen of birch pollen," J. Allergy Clin. Immunol.103(1): 107-113 (1999).
Heath et al., "Cytotoxic T lymphocyte activation by cross-priming," Curr. Opin. Immunol 11: 314-318 (1999).
Herzig et al., "Dynein light chain interacts with NRF-1 and EWG, structurally and functionally related transcription factors from humans and *drosophila*," J. Cell Sci. 113: 4263-4273 (2000).
Hoe et al., "Molecular cloning of Gaf1, a Schizosaccharomyces pombe GATA factor, which can function as a transcriptional activator," Gene 215:319-328 (1998).
Holgate, S., "The epidemic of allergy and asthma," Nature 402 (6760 Suppl): B2-B4 (1999).
Hsu et al., "Immunoprophylaxis of allergen-induced immunoglobulin E synthesis and airway hyperresponsiveness in vivo by genetic immunization," Nat. Med. 2(5):540-544 (1996).
Itoh et al., "The transcriptional co-activator P/CAF potentiates TGF-β/Smad signaling," Nucl. Acids Res. 28(21):4291-4298 (2000).
Jilek et al., "Antigen-independent suppression of the allergic immune response to bee venom phospholipase A2 by DNA vaccination in CBA/J mice," J. Immunol. 166:3612-3621 (2001).
Kataoka et al., "MafA is a glucose-regulated and pancreatic β-cell-specific transcriptional activator for the insulin gene," J. Biol. Chem. 277(51):49903-49910 (2002).
Kumaraguru et al., "Involvement of an ATP-dependent peptide chaperone in cross-presentation after DNA immunization," J. Immunol. 165 (2):750-759 (2000).
Leitner et al., "Nucleic acid for treatment of cancer: genetic vaccines and DNA adjuvants," J. Curr. Pharm. Des. 7(16):1641-1667 (2001).
Li et al., "Engineered recombinant peanut protein and heat-killed Listeria monocytogenes coadministration protects against peanut-induced anaphylaxis in a murine model," J Immunol. 170(6):3289-3295 (2003).
Li et al., "Persistent protective effect of heat-killed *Escherichia coli* producing "engineered" recombinant peanut proteins in a murine model of peanut allergy," J. Allergy Clin. Immunol. 112(1):159-167 (2003).
Liu et al., "Blockage of peanut allergy with a novel Ara h 2-Fcγ fusion protein in mice," J. Allergy Clin. Immunol. 131(1):213-221 (2013).
Liu et al., "Characterization of Bcl10 as potential transcriptional activator that interacts with general transcription factor TFIIB," Biochem. Biophys. Res. Comm. 320(1): 1-6 (2004).
Long, A., "The nuts and bolts of peanut allergy," N. Engl. J. Med. 346 (17):1320-1322 (2002).
Lu et al., "CD40-independent pathways of T cell help for priming of CD8(+) cytotoxic T lymphocytes," J. Exp. Med. 191(3):541-550 (2000).
Mosmann et al., "TH1 and TH2 cells: different patterns of lymphokine secretion lead to different functional properties," Annu. Rev. Immunol. 7:145-173 (1989).
Omori et al., "CREB-H: a novel mammalian transcription factor belonging to the CREB/ATF family and functioning via the box-B element with a liver-specific expression," Nucl. Acids Res. 29(10): 2154-2162 (2001).

(56) References Cited

OTHER PUBLICATIONS

Letter/Written Disclosure of the Supplemental Information Disclosure Statement for the above-referenced application, filed herewith on Aug. 29, 2017, 2 pages.
Changqin, Q. and C, and Xuepeng (eds.), "Research and Development of Genetic Engineering Vaccine for Animal Disease," China Agricultural Publishing House, 146-150 (2005) [English translation, 6 pages].
Daiming, F. (ed.), "Introduction to Tumor Research," vol. 3, Xi'an Jiaotong University Press, 79-82 (2003) [English translation, 4 pages].
Miller et al., "Current and emerging immunotherapeutic approaches to treat and prevent peanut allergy," Expert Review of Vaccines 11(12):1471-1481 (2012).
Office Action, dated May 2, 2017, in connection with corresponding Chinese Patent Application No. 201480024524.2 [Translation of Office Action in English], 5 pages.
Office Action, dated May 22, 2017, in connection with corresponding Russian Patent Application No. 2015144308 [Translation of Office Action in English], 5 pages.
Extended European Search Report, dated Sep. 8, 2016, in connection with European Patent Application No. 14763738.3, 8 pages.
Response, filed Apr. 5, 2017, to European Search Report, dated Sep. 8, 2016, in connection with corresponding European Patent Application No. 14763738.3, 9 pages.
Letter/Written Disclosure of the Supplemental Information Disclosure Statement for the above-referenced application, filed herewith on Feb. 2, 2018, 2 pages.
Ecker et al., "Increasing Gene Expression in Yeast by Fusion to Ubiquitin," JBC 264(13):7715-7719 (1989).
International Preliminary Report on Patentability, dated Sep. 15, 2015, in connection with International Patent Application No. PCT/AU2014/000286, 5 pages.
Communication pursuant to Article 94(3) EPC (Examination Report), dated Nov. 30, 2017, in connection with European Patent Application No. 14 763 738.3, 6 pages.
Letter/Written Disclosure of the Supplemental Information Disclosure Statement for the above-referenced application, filed herewith on Jun. 5, 2018, 2 pages.
Notice of Acceptance, dated Mar. 1, 2018, in connection with corresponding Australian Patent Application No. 2014231734, 3 pages.
Office Action, dated Mar. 6, 2018, in connection with corresponding Japanese Patent Application No. 561833/2015 [English translation], 8 pages.
Letter/Written Disclosure of the Supplemental Information Disclosure Statement for the above-referenced application, filed herewith on Dec. 10, 2015, 2 pages.
Oppenheimer et al., "Treatment of peanut allergy with rush immunotherapy," J. Allergy Clin. Immunol. 90(2):256-262 (1992).
Parronchi et al., "Redirecting Th2 responses in allergy," Curr. Top. Microbiol. Immunol. 238:27-56 (1999).
Polo et al., "Virus-based vectors for human vaccine applications," Drug Discov. Today 7(13):719-727 (2002).
Raz et al., "Preferential induction of a Th1 immune response and inhibition of specific IgE antibody formation by plasmid DNA immunization," Proc. Natl. Acad. Sci. USA. 93(10):5141-5145 (1996).
Ridge et al., "A conditioned dendritic cell can be a temporal bridge between a CD4+ T-helper and a T-killer cell," Nature 393(6684):474-478 (1998).
Rocha et al., "Recombinant viruses as tools to induce protective cellular immunity against infectious diseases," Int. Microbiol. 7(2):83-94 (2004).
Roy et al., "Oral gene delivery with chitosan—DNA nanoparticles generates immunologic protection in a murine model of peanut allergy," Nat. Med. 5(4):387-391 (1999).
Sachs et al., "Isolation and partial characterization of a major peanut allergen," J. Allergy Cin. Immuno. 67(1):27-34 (1981).

Sakai et al., "*Arabidopsis* ARR1 and ARR2 response regulators operate as transcriptional activators," The Plant J. 24(6):703-711 (2000).
Sanderson et al., "Uptake and transport of macromolecules by the intestine: Possible role in clinical disorders (an Update)," Gastroenterology 104(2):622-639 (1993).
Shaheen et al., "Measles and atopy in Guinea-Bissau," The Lancet 347:1792-1796 (1996).
Sicherer et al., "Advances in allergic skin disease, anaphylaxis, and hypersensitivity reactions to foods, drugs, and insects in 2009," J. Allergy Clin. Immunol. 125(1):85-97 (2010).
Singh et al., "The paradigm of Th1 and Th2 cytokines: Its relevance to autoimmunity and allergy," Immunol. Res. 20(2):147-161 (1999).
Slater et al., "A DNA vaccine for allergen immunotherapy using the latexallergen Hev b 5," Arb. Paul Ehrlich Int. Bundesamt Sera ImpfstoffeFrankf. A. M. 91:230-235 (1997).
Smith, G., "Expression of genes by vaccinia virus vectors," In *Molecular Virology: A practical approach*, Edited by A. Dawson and R. Elliott. IRL Press at Oxford University Press, Oxford UK 9:257-283 (1993).
Spiegelberg et al., "DNA immunization: a novel approach to allergen-specific immunotherapy," Allergy 52(10):964-970 (1997).
Srivastava et al., "Food allergy herbal formula-2 silences peanut-induced anaphylaxis for a prolonged posttreatment period via IFN-gamma-producing CD8+ T cells," J. Allergy Clin. Immunol. 123(2):443-451 (2009).
Szuts et al., "LexA chimeras reveal the function of *Drosophila* Fos as a context-dependent transcriptional activator," Proc. Natl. Acad. Sci. 97(10):5351-5356 (2000).
Tanabe et al., "The mammalian HSF4 gene generates both an activator and a repressor of heat shock genes by alternative splicing," J. Biol. Chem. 274(39):27845-27856 (1999).
Toda et al., "Inhibition of immunoglobulin E response to Japanese cedar pollen allergen (Cry j 1) in mice by DNA immunization: Different outcomes dependent on the plasmid DNA inoculation method," Immunology 99:179-186 (2000).
Turcanu et al., "IgE-mediated facilitated antigen presentation underlies higher immune responses in peanut allergy," Allergy 65(10):1274-1281 (2010).
UniProt Database Accession No. P43238, "Allergen Ara h 1, clone P41B precursor [Arachis hypogaea]" Published on Nov. 26, 2014 [online] [retrieved on Nov. 11, 2015] Retrieved from:<URL:ncbi.nlm.nih.gov/protein/P43238 [4 pages].
UniProt Database Accession No. P43238, "Allergen Ara h 1, clone P41B [Arachis hypogaea]" Published on Nov. 26, 2014 [online][retrieved on Dec. 1, 2015] Retrieved from:<URL:ncbi.nlm.nih.gov/protein/P43238.1 [5 page].
UniProt Database Accession No. Q647G9, "Conglutin, Allergen Ara h 6 precursor [Arachis hypogaea]" Published on Oct. 14, 2015 [online][retrieved on Nov. 11, 2015] Retrieved from:<URL:ncbi.nlm.nih.gov/protein/Q647G9 [3 pages].
UniProt Database Accession No. Q8GV20, "Allergen Ara h 2.02 [Arachis hypogaea]" Published on Oct. 31, 2006 [online] [retrieved on Dec. 1, 2015] Retrieved from:<URL:ncbi.nlm.nih.gov/protein/Q8GV20?report=genpept [1 page].
Wu et al., "MAML1, a human homologue of *Drosophila* Mastermind, is a transcriptional co-activator for NOTCH receptors," Nat. Genet. 26:484-489 (2000).
International Search Report and Written Opinion of the Internatinal Searching Authority, dated Apr. 4, 2014, in connection with corresponding International Patent Application PCT/AU2014/000286, 7 pages.
Letter/Written Disclosure of the Supplemental Information Disclosure Statement for the above-referenced application, filed herewith on Dec. 26, 2018, 2 pages.
Examiner's Report, dated Aug. 16, 2018, in connection with corresponding Canadian Patent Application No. 2,906,735, 4 pages.
Response, filed Jun. 7, 2018, to Communication pursuant to Article 94(3) EPC (Examination Report), dated Nov. 30, 2017, in connection with corresponding European Patent Application No. 14 763 738.3, 13 pages.

(56) References Cited

OTHER PUBLICATIONS

Communication Pursuant to Article 94(3) EPC (Examination Report), dated Dec. 19, 2018, in connection with corresponding European Patent Application No. 14 763 738.3, 12 pages.
Albrecht et al., "Vaccination with a modified vaccinia virus Ankara-based vaccine protects mice from allergic sensitization," Journal of Gene Medicine 10(12):1324-1333 (2008).
Bohnen et al., "Vaccination with recombinant modified vaccinia virus Ankara prevents the onset of intestinal allergy in mice," Clinical and Translational Allergy 3(Suppl. 3):O24 (2013).
Bohnen et al., "Vaccination with recombinant modified vaccinia virus Ankara prevents the onset of intestinal allergy in mice," Allergy 68(8):1021-1028 (2013).
Jentarra et al., "Vaccinia viruses with mutations in the E3L gene as potential replication-competent, attenuated vaccines: Scarification vaccination," Vaccine 26(23):2860-2872 (2008).
Tewari et al., "A cytosolic pathway for MHC class II-restricted antigen processing that is proteasome and TAP dependent," Nature Immunology 6(3):287-294 (2005).
Letter/Written Disclosure of the Supplemental Information Disclosure Statement for the above-referenced application, filed herewith on Nov. 7, 2019, 2 pages.
Response, filed Feb. 19, 2019, to Examiner's Report, dated Aug. 16, 2018, in connection with corresponding Canadian Patent Application No. 2,906,735, 65 pages.
Response, filed Apr. 12, 2019, to Communication Pursuant to Article 94(3) EPC (Examination Report), dated Dec. 19, 2018, in connection with corresponding European Patent Application No. 14 763 738.3, 14 pages.
Communication Pursuant to Article 94(3) EPC (Examination Report), dated Aug. 16, 2019, in connection with corresponding European Patent Application No. 14 763 738.3, 7 pages.
Zhuang, Y. and Dreskin, S. C., "Redefining the major peanut allergens," Immunol. Res. 55:125-134 (2013).
Letter/Written Disclosure of the Supplemental Information Disclosure Statement for the above-referenced application, filed herewith on Jun. 29, 2020, 2 pages.
Response, filed Nov. 18, 2019, to Communication Pursuant to Article 94(3) EPC (Examination Report), dated Aug. 16, 2019, in connection with corresponding European Patent Application No. 14 763 738.3, 9 pages.
Communication Pursuant to Article 94(3) EPC (Examination Report), dated Feb. 28, 2020, in connection with corresponding European Patent Application No. 14 763 738.3, 4 pages.
Response, filed Apr. 23, to M Communication Pursuant to Article 94(3) EPC (Examination Report), dated Feb. 28, 2020, in connection with corresponding European Patent Application No. 14 763 738.3, 105 pages.
Aalberse et al., "In silico predictability of allergenicity: From amino acid sequence via 3-D structure to allerginicity," Mol. Nutr. Food Res. 50:625-627 (2006).
Bercovici et al., "New Methods for Assessing T-Cell Responses," Clin. Diagn. Lab. Immunol. 7(6):859-864 (2000).
Burks et al., "Recombinant Peanut Allergen *Ara h* 1 Expression and IgE Binding in Patients with Peanut Hypersensitivity," J. Clin. Invest. 96:1715-1721 (1995).
Cabanos et al., "Crystal structure of the major peanut allergen Ara h 1," Mol. Immunol. 49:115-123 (2011).
Chen et al., "Determination of Specific CD4 and CD8 T Cell Epitopes after AAV2- and AAV8-hF.IX Gene Therapy," Mol. Ther. 13(2):260-269 (2006).
Chruszcz et al., "Structural and Immunologic Characterization of Ara h 1, a Major Peanut Allergen," J. Biol. Chem. 286(45):39318-39327 (2011).
Dodo et al., "A Genetic Engineering Strategy to Eliminate Peanut Allergy," Current Allergy and Asthma Reports 5:67-73 (2005).
Duncan et al., "Stabilization of an E3 Ligase-E2-Ubiquitin Complex Increases Cell Surface MHC Class I Expression," J. Immunol. 184:6978-6985 (2010).

Finley et al., "Inhibition of Proteolysis and Cell Cycle Progression in a Multiubiquitination-Deficient Yeast Mutant," Mol. Cell. Biol. 14(8): 5501-5509 (1994).
Food and Agriculture Organization of the United Nations (FAO), "Evaluation of Allergenicity of Genetically Modified Foods. Report of a Joint FAO/WHO Expert Consultation on Allergenicity of Foods Derived from Biotechnology," Rome, Italy, Jan. 22-25, 2001, 29 pages.
Gomez et al., "Poxvirus vectors as HIV/AIDS vaccines in humans," Human Vaccines & Immunotherapeutics 8(9):1192-1207 (2012).
Karosiene et al.,"*NetMHCcons*: a consensus method for the major histocompatibility complex class I predictions," Immunogeneties 64:177-186 (2012).
Lehmann et al., "Structure and Stability of 2S Albumin-Type Peanut Allergens: Implications for the Severity of Peanut Allergic Reactions," Biochem. J. 395(3):463-472 (2006).
Lehmann et al., "High-yield expression in *Escherichia coli*, purification, and characterization of properly folded major peanut allergen Ara h 2," Protein Expression and Purification 31:250-259 (2003).
Lin et al., "Evaluation of MHC class I peptide binding prediction servers: Applications for vaccine research," BMC Immunology 9:8 (2008), 13 pages.
Lundegaard et al., "Prediction of epitopes using neural network based methods," Journal of Immunological Methods 374:26-34 (2011).
Lundegaard et al., "Accurate approximation method for prediction of class I MHC affinities for peptides of length 8, 10 and 11 using prediction tools trained on 9mers," Bioinformatics 24(11): 1397-1398 (2008).
Lundegaard et al., "NetMHC-3.0: accurate web accessible predictions of human, mouse and monkey MHC class I affinities for peptides of length 8-11," Nucleic Acids Research 36:W509-W512 (2008).
MacNamara et al., "T-Cell Epitope Prediction: Resealing Can Mask Biological Variation between MHC Molecules," PLoS Comput. Biol. 5(3):e1000327 (2009), 7 pages.
Marsland et al., "Bystander suppression of allergic airway inflammation by lung resident memory CD8+ T cells," Proc. Natl. Acad Sci. USA 101(16):6116-6121 (2004).
Mueller et al., "The Molecular Basis of Peanut Allergy," Curr. Allergy Asthma Rep. 14(5):429 (2014), 18 pages.
Mueller et al., "Ara h 2: crystal structure and IgE binding distinguish two sub-populations of peanut allergic patients by epitope diversity," Allergy, 66(7):878-885 (2011).
Nielsen et al., "*NetMHCpan*, a Method for Quantitative Predictions of Peptide Binding to Any HLA-A and -B Locus Protein of Known Sequence," PLoS ONE 2(8):e796 (2007), 10 pages.
Parrino, J. and Graham, B. S., "Smallpox vaccines: Past, present, and future," J. Allergy Clin. Immunol. 118(6):1320-1326 (2006).
Pastoret, P. P., and Vanderplasschen, A., "Poxviruses as vaccine vectors," Comp. Immun. Microbiol. Infect. Dis. 26:343-355 (2003).
Pickart, C. M. and Eddins, M. J., "Ubiquitin: structures, functions, mechanisms," Biochimica et Biophysica Acta 1695:55-72 (2004).
Plant Food Allergens, E. N. Clare Mills & Peter R. Shewry, p. 50 (2008).
Pricked et al., "Ara h 2 peptides containing dominant CD4$^+$T-cell epitopes: Candidates for a peanut allergy therapeutic," J. Allergy Clin. Immunol. 127(3):608-615 (2011).
Schein et al., "Bioinformatics Approaches to Classifying Allergens and Predicting Cross-Reactivity," Immunol. Allergy Clin. North Am. 27(1):1-27 (2007).
Search results for "peanut." Allergen Nomenclature, available from the IUIS website, at <URL:allergen.org/search.php?allergensource=peanut&searchsource=Search, 2 pages.
Spence et al., "A Ubiquitin Mutant with Specific Defects in DNA Repair and Multiubiquitination," Mol. Cell. Biol. 15(3):1265-1273 (1995).
Suhrbier, A., "Polytope vaccines for the codelivery of multiple CD8T-cell epitopes," Expert Rev. Vaccines 1(2):207-213 (2002).
Thomas et al., "CD8 T Cells Inhibit IgE via Dendritic Cell IL-12 Induction That Promotes Th1 T Cell Counter-Regulation," J. Immunol. 168:216-223 (2002).

(56) References Cited

OTHER PUBLICATIONS

Tong et al., "Methods and protocols for prediction of immunogenic epitopes," *Briefings in Bioinformatics* 8(2):96-108 (2006).
Tripathi et al., "Recombinant Allergens—gateway to efficient Diagnosis and Therapy for Atopic Asthma and Rhinitis," *Indian J. Allergy Asthma Immunol.* 20(1):41-51, p. 45, Table 1, (2006).
Tsirigotis et al., "Sensitivity of Mammalian Cells Expressing Mutant Ubiquitin to Protein-damaging Agents," *J. Biol. Chem.* 276(49):46073-46078 (2001).
Vaughan et al., "Strategies to Query and Display Allergy-Derived Epitope Data from the Immune Epitope Database," *Int. Arch. Allergy Immunol.* 160:334-345 (2013).
Wells et al., "Regulation of allergic airway inflammation by class I-restricted allergen presentation and CD8 T-cell infiltration," *J. Allergy Clin. Immunol.* 119(1):226-234 (2007).
Yoshida et al., "Effect of Interferon-γ on Allergic Airway Responses in Interferon-γ-deficient Mice," *Am. J. Respir Crit. Care Med.* 166:451-456 (2002).
Ziv et al., "A Perturbed Ubiquitin Landscape Distinguishes Between Ubiquitin in Trafficking and in Proteolysis," *Molecular & Cellular Proteomics* 10.5, DOI: 10.1074/mcp.M111.009753 (2011), 22 pages.
Letter/Written Disclosure of the Supplemental Information Disclosure Statement for the above-referenced application, filed herewith on Jul. 21, 2020, 4 pages.
Liu et al., "Blockade of peanut allergy with a novel Ara h 2-Fcγ fusion protein in mice," J. Allergy Clin. Immunol. 131(1):213-221. e5 (2013), 14 pages.
Extended European Search Report, dated Apr. 23, 2020, issued in connection with corresponding European Patent Application No. 20156953.0, 22 pages.
Letter/Written Disclosure of the Supplemental Information Disclosure Statement for the above-referenced application, filed herewith on Mar. 5, 2021, 2 pages.
Office Action, dated Jan. 19, 2018, in connection with corresponding Chinese Patent Application No. 201480024524.2 [English translation of Office Action; and original document as issued in Chinese], 14 pages.
Response and Amendment, filed Jun. 6, 2018, to the Office Action, dated Mar. 6, 2018, in connection with corresponding Japanese Patent Application No. 2015-561833 [English translation; and original Response as filed in Japanese], 17 pages.
Decision of Refusal, dated Nov. 27, 2018, in connection with corresponding Japanese Patent Application No. 2015-561833 [English translation; and original document as issued in Japanese], 10 pages.
Request for Trial and Appeal, submitted Mar. 26, 2019, responsive to the Decision of Refusal, dated Nov. 27, 2018, in connection with corresponding Japanese Patent Application No. 2015-561833 [English translation; and original document as filed in Japanese], 18 pages.
Decision to Grant, dated Jun. 7, 2019 (dated Jun. 18, 2019), in connection with corresponding Japanese Patent Application No. 2015-561833 [English translation; and original document as issued in Japanese], 5 pages.
Office Action, dated Jun. 2, 2020, issued in connection with corresponding Japanese Patent Application No. 2019-059511 [English translation; and original document as issued in Japanese], 10 pages.
Response, submitted Aug. 25, 2020, to the Office Action, dated Jun. 2, 2020, in connection with corresponding Japanese Patent Application No. 2019-059511 [English translation; and original documents as submitted in Japanese], 100 pages.
Office Action, dated Jan. 12, 2021, issued in connection with corresponding Japanese Patent Application No. 2019-059511 [English translation; and original document as issued in Japanese], 6 pages.
Office Action, dated Nov. 26, 2018, in connection with corresponding Korean Patent Application No. 10-2015-7029396 [English translation; and original document as issued in Korean], 11 pages.
Response, submitted Mar. 21, 2019, to the Office Action, dated Nov. 26, 2018, in connection with corresponding Korean Patent Application No. 10-2015-7029396 [English translation; and original documents as filed in Korean], 46 pages.
Notice of Final Rejection, dated May 28, 2019, in connection with corresponding Korean Patent Application No. 10-2015-7029396 [English translation; and original document as issued in Korean], 5 pages.
Response, submitted Jul. 16, 2019, to Notice of Final Rejection, dated May 28, 2019, in connection with corresponding Korean Patent Application No. 10-2015-7029396 [English translation; and original documents as filed in Korean], 20 pages.
Notice of Final Rejection, dated Aug. 15, 2019, in connection with corresponding Korean Patent Application No. 10-2015-7029396 [English translation; and original document as issued in Korean], 6 pages.
Decision, dated Feb. 24, 2020, on the Appeal, filed Nov. 13, 2019, against the Notice of Final Rejection, dated Aug. 15, 2019, in connection with corresponding Korean Patent Application No. 10-2015-7029396 [English translation; and original document as issued in Korean], 39 pages.
Decision to Grant, dated Mar. 27, 2020, in connection with corresponding Korean Patent Application No. 10-2015-7029396 [English translation; and original document as issued in Korean], 2 pages.
Notification of Reason for Refusal (Office Action), dated Dec. 26, 2019, in connection with corresponding Korean Patent Application No. 10-2019-7033558 [English translation; and original document as issued in Korean], 7 pages.
Response and Amendment, submitted Jun. 25, 2020, to Notification of Reason for Refusal (Office Action), dated Dec. 26, 2019, in connection with corresponding Korean Patent Application No. 10-2019-7033558 [English translation; and original documents as filed in Korean], 44 pages.
Decision to Grant, dated Oct. 30, 2020, in connection with corresponding Korean Patent Application No. 10-2019-7033558 [English translation; and original document as issued in Korean], 2 pages.
Response, filed Jan. 8, 2021, to Communication under Rule 71(3) EPC (Intention to Grant), dated Sep. 9, 2020, issued in connection with corresponding European Patent Application No. 14 763 738.3, 15 pages.
Communication under Rule 71(3) EPC (Intention to Grant), dated Feb. 12, 2021, issued in connection with corresponding European Patent Application No. 14 763 738.3, 162 pages [including text intended for grant].
Communication Noting Loss of Rights Pursuant to Rule 112(1) EPC, dated Feb. 19, 2021, issued in connection with corresponding European Patent Application No. 20156953.0, 2 pages.
Letter/Written Disclosure of the Supplemental Information Disclosure Statement for the above-referenced application, filed herewith on Jun. 21, 2021, 2 pages.
Response, filed Apr. 12, 2021, to Communication under Rule 71(3) EPC (Intention to Grant), dated Feb. 12, 2021, in connection with corresponding European Patent Application No. 14 763 738.3, 5 pages.
Result of Consultation providing a Communication pursuant to Article 94(3) EPC (Examination Report), dated Apr. 20, 2021, resulting from the Consultation by Telephone with Applicant/ Representative that took place on Apr. 14, 2021, in connection with corresponding European Patent Application No. 14 763 738.3, 4 pages.
Response, filed May 4, 2021, to Communication pursuant to Article 94(3) EPC (Examination Report), dated Apr. 20, 2021, in connection with corresponding European Patent Application No. 14 763 738.3, 5 pages.
Response, filed Aug. 28, 2017, to Office Action, dated May 11, 2017, in connection with corresponding Israeli Patent Application No. 241596 [Response as filed with a partial English translation, as accessed from <URL:israelpatents.justice.gov.il/#/en/patent-file/details/241596 on Jun. 14, 2021], 3 pages.
Letter/Written Disclosure of the Supplemental Information Disclosure Statement for the above-referenced application, filed herewith on Nov. 24, 2020, 2 pages.

(56) References Cited

OTHER PUBLICATIONS

Result of Consultation, dated Aug. 27, 2020, providing a summary of the Consultation by Telephone with Applicant/Representative that took place on Aug. 14, 2020, in connection with corresponding European Patent Application No. 14 763 738.3, 3 pages.

Communication under Rule 71(3) EPC (Intention to Grant), dated Sep. 9, 2020, issued in connection with corresponding European Patent Application No. 14 763 738.3, 162 pages [including text intended for grant].

* cited by examiner

FIGURE 2

*UBc.PHAVag Expression Cassette*

```
LOCUS       UBc.PHAVag expression cassette         4705 bp    DNA      linear    SYN
10-MAR-2014
DEFINITION  SCV-UBcPHAVag expression cassette
ORGANISM    Vaccinia Virus
COMMENT     Textco/File created by Gene Construction Kit (TextcoBioSoftware)
FEATURES             Location/Qualifiers
misc_feature    9..52
                     /label="prPs"
                     /note="Vaccinia early/late promoter"
     CDS             53..4690
                     /label="UBc.PHAV"
                     /note="Protein coding sequence of the ubiquitinated peanut
hypoallergy vaccine antigen"
     CDS             53..280
                     /label="Ubc"
                     /note="Ubiquitin C monomer.  Terminal amino acid changed to
""A"""
     CDS             281..2155
                     /label="ara h1"
                     /note="protein coding sequence of ara h 1"
     CDS             2156..2668
                     /label="ara h2"
                     /note="Protein coding sequence of ara h 2"
     CDS             2669..4255
                     /label="ara h3"
                     /note="Protein coding sequence of ara h 3"
     CDS             4256..4690
                     /label="ara h6"
                     /note="Protein coding sequence of ara h 6"
misc_feature    4691..4697
                     /label="T5NT"
                     /note="Pox virus early transcriptional stop sequence"
ORIGIN
        1 TTAattaaca AAAAATTGAA ATTTTATTTT TTTTTTTTGG AATATAAATA AtATGCAGAT
       61 CTTTGTGAAA ACACTCACGG GAAAAACTAT AACTCTTGAG GTGGAGCCCT CTGACACAAT
      121 CGAAAATGTG AAAGCCAAGA TCCAAGATAA GGAAGGCATC CCTCCAGACC AGCAACGGCT
      181 CATCTTTGCG GGCAAACAAC TGGAGGATGG GCGCACTCTC AGTGATTACA ATATTCAAAA
      241 GGAATCTACA CTGCACCTGG TTCTTAGGCT GCGGGGAGCC CGAGGCAGAG TCAGCCCTCT
      301 GATGCTGCTG TTGGGGATCT TGGTTCTTGC ATCCGTTTCA GCCACACATG CCAAGTCCAG
      361 CCCATACCAG AAAAAGACCG AGAACCCATG TGCTCAGCGG TGCCTCCAGT CATGTCAGCA
      421 GGAACCCGAT GACCTCAAGC AAAAGGCGTG TGAAAGCAGA TGTACGAAAC TGGAATACGA
      481 CCCCAGATGC GTGTACGATC CACGAGGCCA TACTGGCACC ACCAATCAAA GATCACCACC
      541 TGGCGAGCGA ACCAGGGGAC GACAGCCAGG GGATTACGAT GACGATAGAC GACAGCCTCG
      601 CCGGGAAGAG GGTGGGCGCT GGGGTCCAGC CGGTCCCAGA GAGCGAGAAC GGGAAGAGGA
      661 CTGGCGCCAA CCCCGGGAGG ACTGGCGCAG ACCTTCACAC CAGCAGCCCC GGAAAATACG
      721 CCCGGAGGGC AGAGAGGGTG AACAGGAATG GGAACCCCT GGCAGTCACG TCAGGGAAGA
      781 AACCAGCCGG AACAACCCCT TCTATTTCCC CTCCCGGAGG TTTAGCACTC GGTACGGGAA
      841 CCAAAACGGA CGCATTCGCG TACTTCAGAG ATTTGATCAA CGCTCACGGC AGTTCCAGAA
      901 CCTTCAAAAC CATCGGATTG TTCAGATCGA GGCCAAACCA AACACTTTGG TTCTGCCAAA
      961 ACATGCTGAT GCAGACAACA TACTGGTGAT ACAGCAGGGT CAAGCCACAG TGACAGTAGC
     1021 CAATGGGAAC AATCGCAAAT CATTCAATCT CGATGAGGGA CACGCACTGA GGATCCCTTC
     1081 TGGCTTTATC TCCTATATAC TGAATCGGCA CGACAATCAA AATCTCAGGG TTGCTAAGAT
     1141 CTCTATGCCA GTCAACACTC CGGGTCAGTT CGAGGATTTC TTTCCCGCGT CCTCACGGGA
     1201 CCAGTCTAGT TATCTTCAAG GATTCAGCAG AAACACCTTG GAAGCGGCCT TTAACGCCGA
     1261 GTTTAACGAG ATCAGGCGGG TGCTTCTCGA GGAGAACGCT GGCGGGAAC AGGAGGAGAG
     1321 AGGCCAACGG CGGTGGTCTA CCAGGTCCAG TGAGAACAAT GAGGGCGTGA TCGTCAAGGT
```

FIGURE 2 (CONTINUED)

```
1381 ATCTAAGGAG CATGTCGAGG AACTGACCAA ACATGCAAAG TCCGTTTCCA AGAAAGGCTC
1441 CGAGGAGGAA GGGGACATTA CGAATCCGAT CAACCTTCGG GAGGGCGAGC CGGATCTGTC
1501 AAATAACTTT GGAAAACTCT TCGAAGTCAA GCCCGACAAA AAGAATCCGC AGTTGCAAGA
1561 TCTGGACATG ATGCTCACGT GTGTCGAGAT TAAGGAAGGA GCACTGATGT TGCCTCACTT
1621 TAACTCCAAA GCCATGGTGA TAGTCGTAGT AAACAAAGGA ACCGGCAATC TGGAGTTGGT
1681 GGCTGTCCGA AAGGAACAAC AGCAAAGAGG GCGGAGGGAA GAAGAGGAAG ATGAGGACGA
1741 GGAGGAGGAG GGATCAAACC GGGAGGTACG CCGATACACA GCGAGGCTGA AAGAGGGAGA
1801 CGTGTTTATC ATGCCGGCAG CACATCCTGT CGCTATCAAC GCCTCTAGCG AGCTCCATTT
1861 GCTGGGGTTC GGGATCAATG CGGAGAACAA TCATCGCATT TTCCTGGCAG GCGACAAGGA
1921 CAACGTTATT GACCAAATTG AGAAGCAAGC CAAGGACCTG GCCTTCCCTG GATCAGGTGA
1981 ACAGGTCGAG AAGCTCATCA AAACCAGAA GGAATCCCAC TTTGTATCTG CCAGACCACA
2041 GTCACAGTCC CAGAGCCCCT CTAGTCCCGA GAAGGAGAGC CCCGAAAAGG AAGATCAAGA
2101 GGAGGAGAAC CAGGGTGGAA AGGGCCCACT GCTTTCCATT CTCAAAGCCT TCAATGCTAA
2161 GCTGACAATA TTGGTGGCAC TGGCACTGTT CCTTCTTGCT GCACACGCGT CAGCCCGGCA
2221 GCAGTGGGAA TTGCAGGGCG ATCGAAGGTG TCAGTCACAG CTGGAGAGGG CGAACCTCCG
2281 GCCTTGTGAA CAGCACCTGA TGCAGAAGAT TCAGCGGGAC GAGGATTCTT ACGGGCGAGA
2341 TCCTTACAGT CCCTCCCAAG ATCCATATAG CCCGTCTCAA GACCCAGATC GCAGGGACCC
2401 ATATAGCCCC AGCCCCTATG ATCGAAGAGG TGCCGGAAGC AGCCAGCATC AGGAAGGTG
2461 CTGCAATGAG CTGAACGAGT TCGAGAACAA CCAGAGATGT ATGTGCGAGG CTCTGCAGCA
2521 GATTATGGAA AATCAATCTG ACCGGCTGCA GGGACGGCAG CAGGAGCAGC AGTTCAAAAG
2581 GGAGCTCCGC AACCTTCCAC AGCAGTGCGG TTTGCGCGCA CCTCAGCGCT GCGACTTGGA
2641 GGTGAAAGC GGAGGTAGAG ACAGATACGC GAAGCTGCTG GAACTCAGCT TCTGTTTCTG
2701 TTTCCTGGTA CTCGGCGCTT CATCAATATC TTTTAGGCAG CAGCCAGAGG AAAATGCCTG
2761 CCAGTTCCAA CGGCTGAACG CTCAGCGACC AGACAATAGG ATCGAATCAG AAGGTGGATA
2821 CATCGAGACT TGGAACCCGA ATAACCAGGA GTTCGAATGT GCAGGCGTGG CACTGTCTCG
2881 CCTTGTTCTC CGACGCAATG CGCTCAGGCG CCCATTCTAT TCCAATGCAC CCCAAGAAAT
2941 CTTTATCCAA CAGGGCAGAG GGTACTTCGG GCTGATCTTT CCCGGCTGTC CCCGGCACTA
3001 TGAGGAACCC CACACACAGG GCAGAAGGAG CCAGAGCCAG CGGCCTCCCC GGAGATTGCA
3061 AGGGGAGGAT CAGAGCCAGC AGCAGAGAGA TTCTCATCAG AAAGTACATA GGTTCGATGA
3121 GGGTGACCTG ATAGCTGTGC CAACCGGTGT TGCCTTTTGG TTGTATAATG ACCACGACAC
3181 AGACGTGGTG GCTGTGTCTC TGACCGATAC AAACAACAAT GACAATCAGC TTGATCAGTT
3241 CCCTAGGCGC TTTAACCTGG CTGGCAACAC CGAACAGGAG TTCTTGAGAT ATCAGCAGCA
3301 GTCTAGGCAG TCTAGGAGGA GGTCCCTGCC ATACTCCCCT TACAGCCCTC AGAGTCAGCC
3361 TAGGCAGGAA GAGAGAGAAT TCAGTCCCAG AGGCCAGCAC TCTAGGCGGG AGCGGGCTGG
3421 GCAGGAGGAG GAAAACGAAG GTGGCAATAT CTTTAGCGGC TTCACTCCAG AGTTTCTGGA
3481 ACAGGCATTC CAAGTAGATG ACAGACAGAT CGTCCAGAAC CTTAGGGGCG AGACTGAATC
3541 AGAAGAGGAA GGGGCAATCG TGACGGTGCG CGGAGGCTTG CGCATCCTGT CCCCTGACCG
3601 CAAACGCAGG GCCGACGAGG AAGAAGAGTA TGACGAGGAT GAATATGAAT ATGATGAGGA
3661 GGATCGAAGG CGCGGAAGGG GCAGTAGGGG ACGAGGGAAC GGCATAGAAG AAACTATTTG
3721 TACCGCGTCC GCCAAGAAGA ATATTGGGCG AAACCGCAGT CCCGACATAT ACAATCCTCA
3781 AGCCGGCAGC CTTAAAACCG CCAACGATCT GAACCTGCTG ATCCTCCGCT GGCTGGGGCC
3841 AAGCGCCGAA TATGGGAATC TGTACCGAAA TGCTCTGTTT GTGGCCCACT ACAATACAAA
3901 TGCCCACTCT ATTATCTACC GCCTCAGAGG GAGGGCTCAT GTGCAAGTGG TCGACAGCAA
3961 TGGGAATCGC GTGTACGATG AGGAGCTCCA AGAAGGGCAT GTCCTTGTTG TGCCTCAGAA
4021 TTTCGCAGTT GCGGGCAAAT CACAGAGTGA GAACTTCGAG TACGTTGCCT TTAAGACCGA
4081 TTCCAGACCC TCCATTGCAA ACCTGGCCGG AGAGAACAGT GTTATTGACA ATCTGCCGGA
4141 GGAAGTGGTT GCTAACAGTT ATGGGCTTCA GCGCGAACAG GCTCGGCAGC TGAAGAACAA
4201 CAATCCGTTC AAGTTTTTCG TCCCTCCATC CCAGCAGTCA CCCAGAGCTG TGGCCGCCAA
4261 ATCCACTATT CTTGTGGCCC TCTTGGCACT CGTGCTGGTC GCCCATGCTT CTGCTATGCG
4321 AAGGGAGAGA GGGCGCCAAG GTGACTCAAG CAGTTGCGAA CGACAAGTGG ACAGAGTGAA
4381 CCTCAAACCT TGCGAACAGC ACATTATGCA GAGAATTATG GGAGAGCAAG AGCAGTATGA
4441 TAGTTATGAT ATCAGATCAA CACGCTCTTC CGATCAGCAA CAGCGGTGTT GCGATGAACT
4501 CAACGAAATG GAGAATACGC AGCGGTGCAT GTGTGAGGCT CTTCAGCAAA TCATGGAAAA
4561 CCAATGCGAT CGGCTCCAAG ATCGACAGAT GGTGCAGCAG TTTAAGCGCG AGCTGATGAA
4621 TTTGCCACAA CAGTGCAACT TCGGGCTCC CCAGAGATGC GACCTCGATG TCAGCGGAGG
4681 GAGATGCTAA TTTTTATCCT GCAGG
```

FIGURE 3

*PHAVag Expression Cassette*

```
LOCUS       PHAVag expression cassette           4480 bp    DNA      linear    SYN 10-
MAR-2014
DEFINITION  PHAVag expression cassette
ORGANISM    Vaccinia virus
            Unclassified.
COMMENT     Textco/File created by Gene Construction Kit (TextcoBioSoftware)
FEATURES             Location/Qualifiers
misc_feature    9..52
                     /label="prPs"
                     /note="Vaccinia early/late promoter"
                     /note="Pox virus early transcriptional stop"
     CDS             53..1930
                     /label="ara h1"
                     /note="Protein coding sequence of ara h 1"
     CDS             1931..2443
                     /label="ara h2"
                     /note="Protein coding sequence of ara h 2"
     CDS             2444..4030
                     /label="ara h3"
                     /note="Protein coding sequence of ara h 3"
     CDS             4031..4465
                     /label="ara h6"
                     /note="Protein coding sequence of ara h 6"
     CDS             53..4465
                     /label="PHAVag"
                     /note="Protein coding sequence of the peanut hypoallergen
vaccine antigen"
misc_feature    4466..4472
                     /label="Transcription stop"
ORIGIN
        1 TTAattaaca AAAAATTGAA ATTTTATTTT TTTTTTTTGG AATATAAATA AtatgCGAGG
       61 CAGAGTCAGC CCTCTGATGC TGCTGTTGGG GATCTTGGTT CTTGCATCCG TTTCAGCCAC
      121 ACATGCCAAG TCCAGCCCAT ACCAGAAAAA GACCGAGAAC CCATGTGCTC AGCGGTGCCT
      181 CCAGTCATGT CAGCAGGAAC CCGATGACCT CAAGCAAAAG GCGTGTGAAA GCAGATGTAC
      241 GAAACTGGAA TACGACCCCA GATGCGTGTA CGATCCACGA GGCCATACTG GCACCACCAA
      301 TCAAAGATCA CCACCTGGCG AGCGAACCAG GGGACGACAG CCAGGGGATT ACGATGACGA
      361 TAGACGACAG CCTCGCCGGG AAGAGGGTGG GCGCTGGGGT CCAGCCGGTC CCAGAGAGCG
      421 AGAACGGGAA GAGGACTGGC GCCAACCCCG GGAGGACTGG CGCAGACCTT CACACCAGCA
      481 GCCCCGGAAA ATACGCCCGG AGGGCAGAGA GGGTGAACAG GAATGGGGAA CCCCTGGCAG
      541 TCACGTCAGG GAAGAAACCA GCCGGAACAA CCCCTTCTAT TTCCCCTCCC GGAGGTTTAG
      601 CACTCGGTAC GGGAACCAAA ACGGACGCAT TCGCGTACTT CAGAGATTTG ATCAACGCTC
      661 ACGGCAGTTC CAGAACCTTC AAAACCATCG GATTGTTCAG ATCGAGGCCA AACCAAACAC
      721 TTTGGTTCTG CCAAAACATG CTGATGCAGA CAACATACTG GTGATACAGC AGGGTCAAGC
      781 CACAGTGACA GTAGCCAATG GAACAATCG CAAATCATTC AATCTCGATG AGGGACACGC
      841 ACTGAGGATC CCTTCTGGCT TTATCTCCTA TATACTGAAT CGGCACGACA ATCAAAATCT
      901 CAGGGTTGCT AAGATCTCTA TGCCAGTCAA CACTCCGGGT CAGTTCGAGG ATTTCTTTCC
      961 CGCGTCCTCA CGGGACCAGT CTAGTTATCT TCAAGGATTC AGCAGAAACA CCTTGGAAGC
     1021 GGCCTTTAAC GCCGAGTTTA ACGAGATCAG GCGGGTGCTT CTCGAGGAGA ACGCTGGCGG
     1081 GGAACAGGAG GAGAGAGGCC AACGGCGGTG GTCTACCAGG TCCAGTGAGA ACAATGAGGG
     1141 CGTGATCGTC AAGGTATCTA AGGAGCATGT CGAGGAACTG ACCAAACATG CAAAGTCCGT
     1201 TTCCAAGAAA GGCTCCGAGG AGGAAGGGGA CATTACGAAT CCGATCAACC TTCGGGAGGG
     1261 CGAGCCGGAT CTGTCAAATA ACTTTGGAAA ACTCTTCGAA GTCAAGCCCG ACAAAAAGAA
     1321 TCCGCAGTTG CAAGATCTGG ACATGATGCT CACGTGTGTC GAGATTAAGG AAGGAGCACT
     1381 GATGTTGCCT CACTTTAACT CCAAAGCCAT GGTGATAGTC GTAGTAAACA AAGGAACCGG
     1441 CAATCTGGAG TTGGTGGCTG TCCGAAAGGA ACAACAGCAA AGAGGGCGGA GGGAAGAAGA
     1501 GGAAGATGAG GACGAGGAGG AGGAGGGATC AAACCGGGAG GTACGCCGAT ACACAGCGAG
```

FIGURE 3 (CONTINUED)

```
1561 GCTGAAAGAG GGAGACGTGT TTATCATGCC GGCAGCACAT CCTGTCGCTA TCAACGCCTC
1621 TAGCGAGCTC CATTTGCTGG GGTTCGGGAT CAATGCGGAG AACAATCATC GCATTTTCCT
1681 GGCAGGCGAC AAGGACAACG TTATTGACCA AATTGAGAAG CAAGCCAAGG ACCTGGCCTT
1741 CCCTGGATCA GGTGAACAGG TCGAGAAGCT CATCAAAAAC CAGAAGGAAT CCCACTTTGT
1801 ATCTGCCAGA CCACAGTCAC AGTCCCAGAG CCCCTCTAGT CCCGAGAAGG AGAGCCCCGA
1861 AAAGGAAGAT CAAGAGGAGG AGAACCAGGG TGGAAAGGGC CCACTGCTTT CCATTCTCAA
1921 AGCCTTCAAT GCTAAGCTGA CAATATTGGT GGCACTGGCA CTGTTCCTTC TTGCTGCACA
1981 CGCGTCAGCC CGGCAGCAGT GGGAATTGCA GGGCGATCGA AGGTGTCAGT CACAGCTGGA
2041 GAGGGCGAAC CTCCGGCCTT GTGAACAGCA CCTGATGCAG AAGATTCAGC GGGACGAGGA
2101 TTCTTACGGG CGAGATCCTT ACAGTCCCTC CCAAGATCCA TATAGCCCGT CTCAAGACCC
2161 AGATCGCAGG GACCCATATA GCCCCAGCCC CTATGATCGA AGAGGTGCCG GAAGCAGCCA
2221 GCATCAGGAA AGGTGCTGCA ATGAGCTGAA CGAGTTCGAG AACAACCAGA GATGTATGTG
2281 CGAGGCTCTG CAGCAGATTA TGGAAAATCA ATCTGACCGG CTGCAGGGAC GGCAGCAGGA
2341 GCAGCAGTTC AAAAGGGAGC TCCGCAACCT TCCACAGCAG TGCGGTTTGC GCGCACCTCA
2401 GCGCTGCGAC TTGGAGGTGG AAAGCGGAGG TAGAGACAGA TACGCGAAGC TGCTGGAACT
2461 CAGCTTCTGT TTCTGTTTCC TGGTACTCGG CGCTTCATCA ATATCTTTTA GGCAGCAGCC
2521 AGAGGAAAAT GCCTGCCAGT TCCAACGGCT GAACGCTCAG CGACCAGACA ATAGGATCGA
2581 ATCAGAAGGT GGATACATCG AGACTTGGAA CCCGAATAAC CAGGAGTTCG AATGTGCAGG
2641 CGTGGCACTG TCTCGCCTTG TTCTCCGACG CAATGCGCTC AGGCGCCCAT TCTATTCCAA
2701 TGCACCCCAA GAAATCTTTA TCCAACAGGG CAGAGGGTAC TTCGGGCTGA TCTTTCCCGG
2761 CTGTCCCCGG CACTATGAGG AACCCCACAC ACAGGGCAGA AGGAGCCAGA GCCAGCGGCC
2821 TCCCCGGAGA TTGCAAGGGG AGGATCAGAG CCAGCAGCAG AGAGATTCTC ATCAGAAAGT
2881 ACATAGGTTC GATGAGGGTG ACCTGATAGC TGTGCCAACC GGTGTTGCCT TTTGGTTGTA
2941 TAATGACCAC GACACAGACG TGGTGGCTGT GTCTCTGACC GATACAAACA ACAATGACAA
3001 TCAGCTTGAT CAGTTCCCTA GGCGCTTTAA CCTGGCTGGC AACACCGAAC AGGAGTTCTT
3061 GAGATATCAG CAGCAGTCTA GGCAGTCTAG GAGGAGGTCC CTGCCATACT CCCCTTACAG
3121 CCCTCAGAGT CAGCCTAGGC AGGAAGAGAG AGAATTCAGT CCCAGAGGCC AGCACTCTAG
3181 GCGGGAGCGG GCTGGCCAGG AGGAGGAAAA CGAAGGTGGC AATATCTTTA GCGGCTTCAC
3241 TCCAGAGTTT CTGGAACAGG CATTCCAAGT AGATGACAGA CAGATCGTCC AGAACCTTAG
3301 GGGCGAGACT GAATCAGAAG AGGAAGGGGC AATCGTGACG GTGCGCGGAG GCTTGCGCAT
3361 CCTGTCCCCT GACCGCAAAC GCAGGGCCGA CGAGGAAGAA GAGTATGACG AGGATGAATA
3421 TGAATATGAT GAGGAGGATC GAAGGCGCGG AAGGGGCAGT AGGGGACGAG GGAACGGCAT
3481 AGAAGAAACT ATTTGTACCG CGTCCGCCAA GAAGAATATT GGGCGAAACC GCAGTCCCGA
3541 CATATACAAT CCTCAAGCCG GCAGCCTTAA AACCGCCAAC GATCTGAACC TGCTGATCCT
3601 CCGCTGGCTG GGGCCAAGCG CCGAATATGG GAATCTGTAC CGAAATGCTC TGTTTGTGGC
3661 CCACTACAAT ACAAATGCCC ACTCTATTAT CTACCGCCTC AGAGGGAGGG CTCATGTGCA
3721 AGTGGTCGAC AGCAATGGGA ATCGCGTGTA CGATGAGGAG CTCCAAGAAG GGCATGTCCT
3781 TGTTGTGCCT CAGAATTTCG CAGTTGCGGG CAAATCACAG AGTGAGAACT TCGAGTACGT
3841 TGCCTTTAAG ACCGATTCCA GACCCTCCAT TGCAAACCTG GCCGGAGAGA ACAGTGTTAT
3901 TGACAATCTG CCGGAGGAAG TGGTTGCTAA CAGTTATGGG CTTCAGCGCG AACAGGCTCG
3961 GCAGCTGAAG AACAACAATC CGTTCAAGTT TTTCGTCCCT CCATCCCAGC AGTCACCCAG
4021 AGCTGTGGCC GCCAAATCCA CTATTCTTGT GGCCCTCTTG GCACTCGTGC TGGTCGCCCA
4081 TGCTTCTGCT ATGCGAAGGG AGAGAGGGCG CCAAGGTGAC TCAAGCAGTT GCGAACGACA
4141 AGTGGACAGA GTGAACCTCA AACCTTGCGA ACAGCACATT ATGCAGAGAA TTATGGGAGA
4201 GCAAGAGCAG TATGATAGTT ATGATATCAG ATCAACACGC TCTTCCGATC AGCAACAGCG
4261 GTGTTGCGAT GAACTCAACG AAATGGAGAA TACGCAGCGG TGCATGTGTG AGGCTCTTCA
4321 GCAAATCATG GAAAACCAAT GCGATCGGCT CCAAGATCGA CAGATGGTGC AGCAGTTTAA
4381 GCGCGAGCTG ATGAATTTGC CACAACAGTG CAACTTTCGG GCTCCCCAGA GATGCGACCT
4441 CGATGTCAGC GGAGGGAGAT GCTAATTTTT ATCCTGCAGG
```

FIGURE 5

Homologous recombination cassette feature table

| Element | Description | Size |
|---|---|---|
| Not 1 | RE site flanking homologous recombination cassette | 8 bp |
| A39R-F1 | Homologous recombination arm 1 | 501 bp |
| EGFP | Enhance Fluorescent Green Protein expression cassette consisting of a vaccinia early/late promoter followed by the protein coding sequence of EGFP and terminated with the poxvirus early transcriptional stop sequence (TTTTTNT) | 771 bp |
| Ecogpt | E. coli guanine phosphoribosyltransferase expression cassette consisting of a vaccinia early/late promoter followed by the protein coding sequence of Ecogpt and terminated with the poxvirus early transcriptional stop sequence (TTTTTNT) | 510 bp |
| prPs | Vaccinia strong synthetic early/late promoter | 44 bp |
| UbcPHAVag Or PHAV | Peanut hypoallergen vaccine antigen expression cassette UBc.PHAV PHAV | 4705bp 4480 bp |
| A39R-F2 | Homologous recombination arm 2 | 501 bp |
| Not I | RE site flanking homologous recombination cassette | 8 bp |

FIGURE 6

*Ubiquitinated Peanut HypoAllergen Vaccine (UBc.PHAV) antigen homologous recombination cassette*

```
LOCUS       UBcPHAV HR Cassette         7010 bp    DNA       linear    SYN 10-MAR-
2014
DEFINITION  UBcPHAV Homologous Recombination Cassette
COMMENT     Textco/File created by Gene Construction Kit (TextcoBioSoftware)
ORGANISM    Vaccinia virus Copenhagen strain
FEATURES             Location/Qualifiers
     CDS             1849..6486
                     /label="UBcPHAV"
                     /note="Ubiquitinated PHAV antigen protein coding sequence"
     misc_feature    9..509
                     /label="A39R-F1"
                     /note=" VACV-COP A39R homologous recombination arm F1"
     misc_feature    517..560
                     /label="prPS"
                     /note=" Vaccinia virus early/late promoter"
     CDS             561..1280
                     /label="EGFP"
                     /note="Enhanced Green Fluorescent Protein coding sequence"
     misc_feature    1281..1287
                     /label="T5NT"
                     /note=" Poxvirus early transcriptional stop sequence"
     misc_feature    1288..1331
                     /label="prPs"
                     /note="Vaccinia virus early/late promoter"
     CDS             1332..1790
                     /label="Ecogpt"
                     /note="Ecogpt protein coding sequence: E. coli guanine
phosphoribosyltransferase"
     misc_feature    1791..1797
                     /label="T5NT"
                     /note=" Poxvirus early transcriptional stop sequence"
     misc_feature    1805..1848
                     /label="prPs"
                     /note="Vaccinia virus early/late promoter"
     CDS             1849..2076
                     /label="UBc"
                     /note=" Human Ubiquitin C monomer.  Terminal amino acid
changed [A]"
     CDS             2077..3951
                     /label="arah1"
                     /note=" Peanut allergen ara h 1 protein coding sequence"
     CDS             3952..4464
                     /label="arah2"
                     /note=" Peanut allergen ara h 2 protein coding sequence"
     CDS             4465..6051
                     /label="arah3"
                     /note="Peanut allergen ara h 3 protein coding sequence"
     CDS             6052..6486
                     /label="arah6"
                     /note=" Peanut allergen ara h 6 protein coding sequence"
     misc_feature    6487..6493
                     /label="T5NT"
                     /note=" Pox virus early transcriptional stop"
     misc_feature    6502..7002
                     /label="A39R-F2"
                     /note=" VACV-COP A39R homologous recombination arm F2"
```

FIGURE 6 (CONTINUED)

```
ORIGIN
        1 GCGGCCGCaatgcccgtaaagataaacatcaacattgtttggtaatcattaaaccaatta
       61 gtatgaagttgaactaatttcacagtagattttattccagtgttatcctcgcatgtataa
      121 gtacctggtaagatatctttatattctataatcaatgagacatcactatccgataacgaa
      181 tgaagtctagcactagtatgccatttacttaatattgtcgtcttggaagttttattataa
      241 gttaaaatatcatggttatccaatttccatctaatatactttgtcggattatctatagta
      301 cacggaataatgatggtatcattacatgctgtatactctatggtctttgtagttgttata
      361 acaaccaacgtatagaggtatatcaacgatattctaactcttgacattttttatttattt
      421 aaaatgatacctttgttatttattttattctattttgctaacggtattgaatggcataag
      481 tttgaaacgagtgaagaaataatttctacGCGCGCCaAA AAATTGAAAT TTTATTTTTT
      541 TTTTTTGGAA TATAAATAAt ATGGTGAGCA AGGGCGAGGA GCTGTTCACC GGGGTGGTGC
      601 CCATCCTGGT CGAGCTGGAC GGCGACGTAA ACGGCCACAA GTTCAGCGTG TCCGGCGAGG
      661 GCGAGGGCGA TGCCACCTAC GGCAAGCTGA CCCTGAAGTT CATCTGCACC ACCGGCAAGC
      721 TGCCCGTGCC CTGGCCCACC CTCGTGACCA CCCTGACCTA CGGCGTGCAG TGCTTCAGCC
      781 GCTACCCCGA CCACATGAAG CAGCACGACT TCTTCAAGTC CGCCATGCCC GAAGGCTACG
      841 TCCAGGAGCG CACCATCTTC TTCAAGGACG ACGGCAACTA CAAGACCCGC GCCGAGGTGA
      901 AGTTCGAGGG CGACACCCTG GTGAACCGCA TCGAGCTGAA GGGCATCGAC TTCAAGGAGG
      961 ACGGCAACAT CCTGGGGCAC AAGCTGGAGT ACAACTACAA CAGCCACAAC GTCTATATCA
     1021 TGGCCGACAA GCAGAAGAAC GGCATCAAGG TGAACTTCAA GATCCGCCAC AACATCGAGG
     1081 ACGGCAGCGT GCAGCTCGCC GACCACTACC AGCAGAACAC CCCCATCGGC GACGGCCCCG
     1141 TGCTGCTGCC CGACAACCAC TACCTGAGCA CCCAGTCCGC CCTGAGCAAA GACCCCAACG
     1201 AGAAGCGCGA TCACATGGTC CTGCTGGAGT TCGTGACCGC CGCCGGGATC ACTCTCGGCA
     1261 TGGACGAGCT GTACAAGTAA tttttatcaA AAAAATTGAAA TTTTATTTTT TTTTTTTGGA
     1321 ATATAAATAA tATGAGCGAA AAATACATCG TCACCTGGGA CATGTTGCAG ATCCATGCAC
     1381 GTAAACTCGC AAGCCGACTG ATGCCTTCTG AACAATGGAA AGGCATTATT GCCGTAAGCC
     1441 GTGGCGGTCT GGTACCGGGT GCGTTACTGG CGCGTGAACT GGGTATTCGT CATGTCGATA
     1501 CCGTTTGTAT TTCCAGCTAC GATCACGACA ACCAGCGCGA GCTTAAAGTG CTGAAACGCG
     1561 CAGAAGGCGA TGGCGAAGGC TTCATCGTTA TTGATGACCT GGTGGATACC GGTGGTACTG
     1621 CGGTTGCGAT TCGTGAAATG TATCCAAAAG CGCACTTTGT CACCATCTTC GCAAAACCGG
     1681 CTGGTCGTCC GCTGGTTGAT GACTATGTTG TTGATATCCC GCAAGATACC TGGATTGAAC
     1741 AGCCGTGGGA TATGGGCGTC GTATTCGTCC CGCCAATCTC CGGTCGCTAA tttttatATT
     1801 TTAAcaAAAA ATTGAAATTT TATTTTTTTT TTTTGGAATA TAAATAAtAT GCAGATCTTT
     1861 GTGAAAACAC TCACGGGAAA AACTATAACT CTTGAGGTGG AGCCCTCTGA CACAATCGAA
     1921 AATGTGAAAG CCAAGATCCA AGATAAGGAA GGCATCCCTC CAGACCAGCA ACGGCTCATC
     1981 TTTGCGGGCA AACAACTGGA GGATGGGCGC ACTCTCAGTG ATTACAATAT TCAAAAGGAA
     2041 TCTACACTGC ACCTGGTTCT TAGGCTGCGG GGAGCCCGAG GCAGAGTCAG CCCTCTGATG
     2101 CTGCTGTTGG GGATCTTGGT TCTTGCATCC GTTTCAGCCA CACATGCCAA GTCCAGCCCA
     2161 TACCAGAAAA AGACCGAGAA CCCATGTGCT CAGCGGTGCC TCCAGTCATG TCAGCAGGAA
     2221 CCCGATGACC TCAAGCAAAA GGCGTGTGAA AGCAGATGTA CGAAACTGGA ATACGACCCC
     2281 AGATGCGTGT ACGATCCACG AGGCCATACT GGCACCACCA ATCAAAGATC ACCACCTGGC
     2341 GAGCGAACCA GGGGACGACA GCCAGGGGAT TACGATGACG ATAGACGACA GCCTCGCCGG
     2401 GAAGAGGGTG GGCGCTGGGG TCCAGCCGGT CCCAGAGAGC GAGAACGGGA AGAGGACTGG
     2461 CGCCAACCCC GGGAGGACTG GCGCAGACCT TCACACCAGC AGCCCCGGAA AATACGCCCG
     2521 GAGGGCAGAG AGGGTGAACA GGAATGGGGA ACCCCTGGCA GTCACGTCAG GGAAGAAACC
     2581 AGCCGGAACA ACCCCTTCTA TTTCCCCTCC CGGAGGTTTA GCACTCGGTA CGGGAACCAA
     2641 AACGGACGCA TTCGCGTACT TCAGAGATTT GATCAACGCT CACGGCAGTT CCAGAACCTT
     2701 CAAAACCATC GGATTGTTCA GATCGAGGCC AAACCAAACA CTTTGGTTCT GCCAAAACAT
     2761 GCTGATGCAG ACAACATACT GGTGATACAG CAGGGTCAAG CCACAGTGAC AGTAGCCAAT
     2821 GGGAACAATC GCAAATCATT CAATCTCGAT GAGGGACACG CACTGAGGAT CCCTTCTGGC
     2881 TTTATCTCCT ATATACTGAA TCGGCACGAC AATCAAAATC TCAGGGTTGC TAAGATCTCT
     2941 ATGCCAGTCA ACACTCCGGG TCAGTTCGAG GATTTCTTTC CCGCGTCCTC ACGGGACCAG
     3001 TCTAGTTATC TTCAAGGATT CAGCAGAAAC ACCTTGGAAG CGGCCTTTAA CGCCGAGTTT
     3061 AACGAGATCA GGCGGGTGCT TCTCGAGGAG AACGCTGGCG GGAACAGGA GGAGAGAGGC
     3121 CAACGGCGGT GGTCTACCAG GTCCAGTGAG AACAATGAGG GCGTGATCGT CAAGGTATCT
     3181 AAGGAGCATG TCGAGGAACT GACCAAACAT GCAAAGTCCG TTTCCAAGAA AGGCTCCGAG
     3241 GAGGAAGGGG ACATTACGAA TCCGATCAAC CTTCGGGAGG CGAGCCGGA TCTGTCAAAT
     3301 AACTTTGGAA AACTCTTCGA AGTCAAGCCC GACAAAAAGA ATCCGCAGTT GCAAGATCTG
     3361 GACATGATGC TCACGTGTGT CGAGATTAAG GAAGGAGCAC TGATGTTGCC TCACTTTAAC
     3421 TCCAAAGCCA TGGTGATAGT CGTAGTAAAC AAAGGAACCG GCAATCTGGA GTTGGTGGCT
     3481 GTCCGAAAGG AACAACAGCA AAGAGGGCGG AGGGAAGAAG AGGAAGATGA GGACGAGGAG
```

FIGURE 6 (CONTINUED)

```
3541 GAGGAGGGAT CAAACCGGGA GGTACGCCGA TACACAGCGA GGCTGAAAGA GGGAGACGTG

3601 TTTATCATGC CGGCAGCACA TCCTGTCGCT ATCAACGCCT CTAGCGAGCT CCATTTGCTG
3661 GGGTTCGGGA TCAATGCGGA GAACAATCAT CGCATTTTCC TGGCAGGCGA CAAGGACAAC
3721 GTTATTGACC AAATTGAGAA GCAAGCCAAG GACCTGGCCT TCCCTGGATC AGGTGAACAG
3781 GTCGAGAAGC TCATCAAAAA CCAGAAGGAA TCCCACTTTG TATCTGCCAG ACCACAGTCA
3841 CAGTCCCAGA GCCCCTCTAG TCCCGAGAAG GAGAGCCCCG AAAAGGAAGA TCAAGAGGAG
3901 GAGAACCAGG GTGGAAAGGG CCCACTGCTT TCCATTCTCA AAGCCTTCAA TGCTAAGCTG
3961 ACAATATTGG TGGCACTGGC ACTGTTCCTT CTTGCTGCAC ACGCGTCAGC CCGGCAGCAG
4021 TGGGAATTGC AGGGCGATCG AAGGTGTCAG TCACAGCTGG AGAGGGCGAA CCTCCGGCCT
4081 TGTGAACAGC ACCTGATGCA GAAGATTCAG CGGGACGAGG ATTCTTACGG GCGAGATCCT
4141 TACAGTCCCT CCCAAGATCC ATATAGCCCG TCTCAAGACC CAGATCGCAG GGACCCATAT
4201 AGCCCCAGCC CCTATGATCG AAGAGGTGCC GGAAGCAGCC AGCATCAGGA AAGGTGCTGC
4261 AATGAGCTGA ACGAGTTCGA GAACAACCAG AGATGTATGT GCGAGGCTCT GCAGCAGATT
4321 ATGGAAAATC AATCTGACCG GCTGCAGGGA CGGCAGCAGG AGCAGCAGTT CAAAAGGGAG
4381 CTCCGCAACC TTCCACAGCA GTGCGGTTTG CGCGCACCTC AGCGCTGCGA CTTGGAGGTG
4441 GAAAGCGGAG GTAGAGACAG ATACGCGAAG CTGCTGGAAC TCAGCTTCTG TTTCTGTTTC
4501 CTGGTACTCG GCGCTTCATC AATATCTTTT AGGCAGCAGC CAGAGGAAAA TGCCTGCCAG
4561 TTCCAACGGC TGAACGCTCA GCGACCAGAC AATAGGATCG AATCAGAAGG TGGATACATC
4621 GAGACTTGGA ACCCGAATAA CCAGGAGTTC GAATGTGCAG GCGTGGCACT GTCTCGCCTT
4681 GTTCTCCGAC GCAATGCGCT CAGGCGCCCA TTCTATTCCA ATGCACCCCA AGAAATCTTT
4741 ATCCAACAGG GCAGAGGGTA CTTCGGGCTG ATCTTTCCCG GCTGTCCCCG GCACTATGAG
4801 GAACCCCACA CACAGGGCAG AAGGAGCCAG AGCCAGCGGC CTCCCCGGAG ATTGCAAGGG
4861 GAGGATCAGA GCCAGCAGCA GAGAGATTCT CATCAGAAAG TACATAGGTT CGATGAGGGT
4921 GACCTGATAG CTGTGCCAAC CGGTGTTGCC TTTTGGTTGT ATAATGACCA CGACACAGAC
4981 GTGGTGGCTG TGTCTCTGAC CGATACAAAC AACAATGACA ATCAGCTTGA TCAGTTCCCT
5041 AGGCGCTTTA ACCTGGCTGG CAACACCGAA CAGGAGTTCT TGAGATATCA GCAGCAGTCT
5101 AGGCAGTCTA GGAGGAGGTC CCTGCCATAC TCCCCTTACA GCCCTCAGAG TCAGCCTAGG
5161 CAGGAAGAGA GAGAATTCAG TCCCAGAGGC CAGCACTCTA GGCGGGAGCG GGCTGGGCAG
5221 GAGGAGGAAA ACGAAGGTGG CAATATCTTT AGCGGCTTCA CTCCAGAGTT TCTGGAACAG
5281 GCATTCCAAG TAGATGACAG ACAGATCGTC CAGAACCTTA GGGGCGAGAC TGAATCAGAA
5341 GAGGAAGGGG CAATCGTGAC GGTGCGCGGA GGCTTGCGCA TCCTGTCCCC TGACCGCAAA
5401 CGCAGGGCCG ACGAGGAAGA AGAGTATGAC GAGGATGAAT ATGAATATGA TGAGGAGGAT
5461 CGAAGGCGCG GAAGGGGCAG TAGGGGACGA GGGAACGGCA TAGAAGAAAC TATTTGTACC
5521 GCGTCCGCCA AGAAGAATAT TGGGCGAAAC CGCAGTCCCG ACATATACAA TCCTCAAGCC
5581 GGCAGCCTTA AAACCGCCAA CGATCTGAAC CTGCTGATCC TCCGCTGGCT GGGGCCAAGC
5641 GCCGAATATG GAATCTGTA CCGAAATGCT CTGTTTGTGG CCCACTACAA TACAAATGCC
5701 CACTCTATTA TCTACCGCCT CAGAGGGAGG GCTCATGTGC AAGTGGTCGA CAGCAATGGG
5761 AATCGCGTGT ACGATGAGGA GCTCCAAGAA GGGCATGTCC TTGTTGTGCC TCAGAATTTC
5821 GCAGTTGCGG GCAAATCACA GAGTGAGAAC TTCGAGTACG TTGCCTTTAA GACCGATTCC
5881 AGACCCTCCA TTGCAAACCT GGCCGGAGAG AACAGTGTTA TTGACAATCT GCCGGAGGAA
5941 GTGGTTGCTA ACAGTTATGG GCTTCAGCGC GAACAGGCTC GGCAGCTGAA GACAACAAT
6001 CCGTTCAAGT TTTTCGTCCC TCCATCCCAG CAGTCACCCA GAGCTGTGGC CGCCAAATCC
6061 ACTATTCTTG TGGCCCTCTT GGCACTCGTG CTGGTCGCCC ATGCTTCTGC TATGCGAAGG
6121 GAGAGAGGGC GCCAAGGTGA CTCAAGCAGT TGCGAACGAC AAGTGGACAG AGTGAACCTC
6181 AAACCTTGCG AACAGCACAT TATGCAGAGA ATTATGGGAG AGCAAGAGCA GTATGATAGT
6241 TATGATATCA GATCAACACG CTCTTCCGAT CAGCAACAGC GGTGTTGCGA TGAACTCAAC
6301 GAAATGGAGA ATACGCAGCG GTGCATGTGT GAGGCTCTTC AGCAAATCAT GGAAAACCAA
6361 TGCGATCGGC TCCAAGATCG ACAGATGGTG CAGCAGTTTA AGCGCGAGCT GATGAATTTG
6421 CCACAACAGT GCAACTTTCG GGCTCCCCAG AGATGCGACC TCGATGTCAG CGGAGGGAGA
6481 TGCTAATTTT TATCCTGCAG Gacttcgaaaccgttatttatagcagatatagggatagga
6541 gtaggaatgccacaaatgaaaaaaatacttaaaatgtaatcttaatcgagtacaccacac
6601 gacaatgaacaaacctaagacagattatgctggttatgcttgctgcgtaatatgcggtct
6661 aattgtcggaattattttttacagcgacactattaaaagttgtagaacgtaaattagttca
6721 tacaccatcaatagataaaacgataaaagatgcatatattagagaagattgtcctactga
6781 ctggataagctataataataaatgtatccatttatctactgatcgaaaaacctgggagga
6841 aggacgtaatacatgcaaagctctaaatccaaattcggatctaattaagatagagactcc
6901 aaacgagttaagttttttaagaagccttagacgaggctattgggtaggagaatccgaaat
6961 attaaaccagacaaccccatataatttttatagctaaaaatgcGCGGCCGC
```

FIGURE 7

*Peanut HypoAllergen Vaccine (PHAV) antigen homologous recombination cassette*

```
LOCUS    PHAV HR cassette        6785 bp    DNA      linear   SYN 10-MAR-2014
DEFINITION  PHAV homologous recombination cassette
ORGANISM  Vaccinia virus Copenhagen strain
COMMENT     Textco/File created by Gene Construction Kit (TextcoBioSoftware)
FEATURES             Location/Qualifiers
     CDS             1849..6261
                     /label="PHAV"
                     /note=" PHAV antigen protein coding sequence"
misc_feature    9..509
                     /label="A39R-F1"
                     /note=" VACV-COP A39R homologous recombination arm 1"
misc_feature    517..560
                     /label="prPs"
                     /note="Vaccinia virus early/late promoter"
     CDS             561..1280
                     /label="EGFP"
                     /note=" Enhanced Green Fluorescent Protein coding sequence"
misc_feature    1281..1287
                     /label="T5NT"
                     /note=" Poxvirus early transcriptional stop sequence"
misc_feature    1288..1331
                     /label="prPs"
                     /note=" Vaccinia virus early/late promoter"
     CDS             1332..1790
                     /label="Ecogpt"
                     /note="Ecogpt protein coding sequence: E. coli guanine
phosphoribosyltransferase"
misc_feature    1791..1797
                     /label="T5NT"
                     /note="  Poxvirus early transcriptional stop sequence"
misc_feature    1805..1848
                     /label="prPs"
                     /note=" Vaccinia virus early/late promoter"
     CDS             1849..3726
                     /label="arah1"
                     /note="Peanut allergen ara h 1 protein coding sequence"
     CDS             3727..4239
                     /label="arah2"
                     /note=" Peanut  allergenara h 2 protein coding sequence"
     CDS             4240..5826
                     /label="arah3"
                     /note="Peanut allergen ara h 3 protein coding sequence"
     CDS             5827..6261
                     /label="arah6"
                     /note=" Peanut allergen ara h 6 protein coding sequence"
misc_feature    6262..6268
                     /label="T5NT"
                     /note=" Pox virus early transcriptional stop"
misc_feature    6277..6777
                     /label="A39R-F2"
                     /note=" VACV-COP A39R homologous recombination arm 2"
ORIGIN
       1 GCGGCCGCaatgcccgtaaagataaacatcaacattgtttggtaatcattaaaccaatta
      61 gtatgaagttgaactaatttcacagtagattttattccagtgttatcctcgcatgtataa
     121 gtacctggtaagatatctttatattctataatcaatgagacatcactatccgataacgaa
     181 tgaagtctagcactagtatgccatttacttaatattgtcgtcttggaagttttattataa
```

FIGURE 7 (CONTINUED)

```
 241 gttaaaatatcatggttatccaatttccatctaatatactttgtcggattatctatagta
 301 cacggaataatgatggtatcattacatgctgtatactctatggtctttgtagttgttata
 361 acaaccaacgtatagaggtatatcaacgatattctaactcttgacatttttttatttattt
 421 aaaatgatacctttgttatttattttattctattttgctaacggtattgaatggcataag
 481 tttgaaacgagtgaagaaataatttctacGCGCGCCcaAA AAATTGAAAT TTTATTTTTT
 541 TTTTTTGGAA TATAAATAAt ATGGTGAGCA AGGGCGAGGA GCTGTTCACC GGGGTGGTGC
 601 CCATCCTGGT CGAGCTGGAC GGCGACGTAA ACGGCCACAA GTTCAGCGTG TCCGGCGAGG
 661 GCGAGGGCGA TGCCACCTAC GGCAAGCTGA CCCTGAAGTT CATCTGCACC ACCGGCAAGC
 721 TGCCCGTGCC CTGGCCCACC CTCGTGACCA CCCTGACCTA CGGCGTGCAG TGCTTCAGCC
 781 GCTACCCCGA CCACATGAAG CAGCACGACT TCTTCAAGTC CGCCATGCCC GAAGGCTACG
 841 TCCAGGAGCG CACCATCTTC TTCAAGGACG ACGGCAACTA CAAGACCCGC GCCGAGGTGA
 901 AGTTCGAGGG CGACACCCTG GTGAACCGCA TCGAGCTGAA GGGCATCGAC TTCAAGGAGG
 961 ACGGCAACAT CCTGGGGCAC AAGCTGGAGT ACAACTACAA CAGCCACAAC GTCTATATCA
1021 TGGCCGACAA GCAGAAGAAC GGCATCAAGG TGAACTTCAA GATCCGCCAC AACATCGAGG
1081 ACGGCAGCGT GCAGCTCGCC GACCACTACC AGCAGAACAC CCCCATCGGC GACGGCCCCG
1141 TGCTGCTGCC CGACAACCAC TACCTGAGCA CCCAGTCCGC CCTGAGCAAA GACCCCAACG
1201 AGAAGCGCGA TCACATGGTC CTGCTGGAGT TCGTGACCGC CGCCGGGATC ACTCTCGGCA
1261 TGGACGAGCT GTACAAGTAA tttttatcaA AAAAATTGAAA TTTTATTTTT TTTTTTTGGA
1321 ATATAAATAA tATGAGCGAA AAATACATCG TCACCTGGGA CATGTTGCAG ATCCATGCAC
1381 GTAAACTCGC AAGCCGACTG ATGCCTTCTG AACAATGGAA AGGCATTATT GCCGTAAGCC
1441 GTGGCGGTCT GGTACCGGGT GCGTTACTGG CGCGTGAACT GGGTATTCGT CATGTCGATA
1501 CCGTTTGTAT TTCCAGCTAC GATCACGACA ACCAGCGCGA GCTTAAAGTG CTGAAACGCG
1561 CAGAAGGCGA TGGCGAAGGC TTCATCGTTA TTGATGACCT GGTGGATACC GGTGGTACTG
1621 CGGTTGCGAT TCGTGAAATG TATCCAAAAG CGCACTTTGT CACCATCTTC GCAAAACCGG
1681 CTGGTCGTCC GCTGGTTGAT GACTATGTTG TTGATATCCC GCAAGATACC TGGATTGAAC
1741 AGCCGTGGGA TATGGGCGTC GTATTCGTCC CGCCAATCTC CGGTCGCTAA tttttatATT
1801 TTAAcaAAAA ATTGAAATTT TATTTTTTTT TTTTGGAATA TAAATAAtatgCGAGGCAGA
1861 GTCAGCCCTC TGATGCTGCT GTTGGGGATC TTGGTTCTTG CATCCGTTTC AGCCACACAT
1921 GCCAAGTCCA GCCCATACCA GAAAAGACC GAGAACCCAT GTGCTCAGCG GTGCCTCCAG
1981 TCATGTCAGC AGGAACCCGA TGACCTCAAG CAAAAGGCGT GTGAAAGCAG ATGTACGAAA
2041 CTGGAATACG ACCCCAGATG CGTGTACGAT CCACGAGGCC ATACTGGCAC CACCAATCAA
2101 AGATCACCAC CTGGCGAGCG AACCAGGGGA CGACAGCCAG GGGATTACGA TGACGATAGA
2161 CGACAGCCTC GCCGGGAAGA GGGTGGGCGC TGGGGTCCAG CCGGTCCCAG AGAGCGAGAA
2221 CGGGAAGAGG ACTGGCGCCA ACCCCGGGAG GACTGGCGCA GACCTTCACA CCAGCAGCCC
2281 CGGAAAATAC GCCCGGAGGG CAGAGAGGGT GAACAGGAAT GGGGAACCCC TGGCAGTCAC
2341 GTCAGGGAAG AAACCAGCCG GAACAACCCC TTCTATTTCC CCTCCCGGAG GTTTAGCACT
2401 CGGTACGGGA ACCAAAACGG ACGCATTCGC GTACTTCAGA GATTTGATCA ACGCTCACGG
2461 CAGTTCCAGA ACCTTCAAAA CCATCGGATT GTTCAGATCG AGGCCAAACC AAACACTTTG
2521 GTTCTGCCAA AACATGCTGA TGCAGACAAC ATACTGGTGA TACAGCAGGG TCAAGCCACA
2581 GTGACAGTAG CCAATGGGAA CAATCGCAAA TCATTCAATC TCGATGAGGG ACACGCACTG
2641 AGGATCCCTT CTGGCTTTAT CTCCTATATA CTGAATCGGC ACGACAATCA AAATCTCAGG
2701 GTTGCTAAGA TCTCTATGCC AGTCAACACT CCGGGTCAGT TCGAGGATTT CTTTCCCGCG
2761 TCCTCACGGG ACCAGTCTAG TTATCTTCAA GGATTCAGCA GAAACACCTT GGAAGCGGCC
2821 TTTAACGCCG AGTTTAACGA GATCAGGCGG GTGCTTCTCG AGGAGAACGC TGGCGGGGAA
2881 CAGGAGGAGA GAGGCCAACG GCGGTGGTCT ACCAGGTCCA GTGAGAACAA TGAGGGCGTG
2941 ATCGTCAAGG TATCTAAGGA GCATGTCGAG GAACTGACCA AACATGCAAA GTCCGTTTCC
3001 AAGAAAGGCT CCGAGGAGGA AGGGGACATT ACGAATCCGA TCAACCTTCG GGAGGGCGAG
3061 CCGGATCTGT CAAATAACTT TGGAAAACTC TTCGAAGTCA AGCCCGACAA AAAGAATCCG
3121 CAGTTGCAAG ATCTGGACAT GATGCTCACG TGTGTCGAGA TTAAGGAAGG AGCACTGATG
3181 TTGCCTCACT TTAACTCCAA AGCCATGGTG ATAGTCGTAG TAAACAAAGG AACCGGCAAT
3241 CTGGAGTTGG TGGCTGTCCG AAAGGAACAA CAGCAAAGAG GGCGGAGGGA AGAAGAGGAA
3301 GATGAGGACG AGGAGGAGGA GGGATCAAAC CGGGAGGTAC GCCGATACAC AGCGAGGCTG
3361 AAAGAGGGAG ACGTGTTTAT CATGCCGGCA GCACATCCTG TCGCTATCAA CGCCTCTAGC
3421 GAGCTCCATT TGCTGGGGTT CGGGATCAAT GCGGAGAACA ATCATCGCAT TTTCCTGGCA
3481 GGCGACAAGG ACAACGTTAT TGACCAAATT GAGAAGCAAG CCAAGGACCT GGCCTTCCCT
3541 GGATCAGGTG AACAGGTCGA GAAGCTCATC AAAAACCAGA AGGAATCCCA CTTTGTATCT
3601 GCCAGACCAC AGTCACAGTC CCAGAGCCCC TCTAGTCCCG AGAAGGAGAG CCCCGAAAAG
3661 GAAGATCAAG AGGAGGAGAA CCAGGGTGGA AAGGGCCCAC TGCTTTCCAT TCTCAAAGCC
3721 TTCAATGCTA AGCTGACAAT ATTGGTGGCA CTGGCACTGT TCCTTCTTGC TGCACACGCG
3781 TCAGCCCGGC AGCAGTGGGA ATTGCAGGGC GATCGAAGGT GTCAGTCACA GCTGGAGAGG
```

FIGURE 7 (CONTINUED)

```
3841 GCGAACCTCC GGCCTTGTGA ACAGCACCTG ATGCAGAAGA TTCAGCGGGA CGAGGATTCT
3901 TACGGGCGAG ATCCTTACAG TCCCTCCCAA GATCCATATA GCCCGTCTCA AGACCCAGAT
3961 CGCAGGGACC CATATAGCCC CAGCCCCTAT GATCGAAGAG GTGCCGGAAG CAGCCAGCAT
4021 CAGGAAAGGT GCTGCAATGA GCTGAACGAG TTCGAGAACA ACCAGAGATG TATGTGCGAG
4081 GCTCTGCAGC AGATTATGGA AAATCAATCT GACCGGCTGC AGGGACGGCA GCAGGAGCAG
4141 CAGTTCAAAA GGGAGCTCCG CAACCTTCCA CAGCAGTGCG GTTTGCGCGC ACCTCAGCGC
4201 TGCGACTTGG AGGTGGAAAG CGGAGGTAGA GACAGATACG CGAAGCTGCT GGAACTCAGC
4261 TTCTGTTTCT GTTTCCTGGT ACTCGGCGCT TCATCAATAT CTTTTAGGCA GCAGCCAGAG
4321 GAAAATGCCT GCCAGTTCCA ACGGCTGAAC GCTCAGCGAC CAGACAATAG GATCGAATCA
4381 GAAGGTGGAT ACATCGAGAC TTGGAACCCG AATAACCAGG AGTTCGAATG TGCAGGCGTG
4441 GCACTGTCTC GCCTTGTTCT CCGACGCAAT GCGCTCAGGC GCCCATTCTA TTCCAATGCA
4501 CCCCAAGAAA TCTTTATCCA ACAGGGCAGA GGGTACTTCG GGCTGATCTT TCCCGGCTGT
4561 CCCCGGCACT ATGAGGAACC CCACACACAG GGCAGAAGGA GCCAGAGCCA GCGGCCTCCC
4621 CGGAGATTGC AAGGGGAGGA TCAGAGCCAG CAGCAGAGAG ATTCTCATCA GAAAGTACAT
4681 AGGTTCGATG AGGGTGACCT GATAGCTGTG CCAACCGGTG TTGCCTTTTG GTTGTATAAT
4741 GACCACGACA CAGACGTGGT GGCTGTGTCT CTGACCGATA CAAACAACAA TGACAATCAG
4801 CTTGATCAGT TCCCTAGGCG CTTTAACCTG GCTGGCAACA CCGAACAGGA GTTCTTGAGA
4861 TATCAGCAGC AGTCTAGGCA GTCTAGGAGG AGGTCCCTGC CATACTCCCC TTACAGCCCT
4921 CAGAGTCAGC CTAGGCAGGA AGAGAGAGAA TTCAGTCCCA GAGGCCAGCA CTCTAGGCGG
4981 GAGCGGGCTG GGCAGGAGGA GGAAAACGAA GGTGGCAATA TCTTTAGCGG CTTCACTCCA
5041 GAGTTTCTGG AACAGGCATT CCAAGTAGAT GACAGACAGA TCGTCCAGAA CCTTAGGGGC
5101 GAGACTGAAT CAGAAGAGGA AGGGGCAATC GTGACGGTGC GCGGAGGCTT GCGCATCCTG
5161 TCCCCTGACC GCAAACGCAG GGCCGACGAG GAAGAAGAGT ATGACGAGGA TGAATATGAA
5221 TATGATGAGG AGGATCGAAG GCGCGGAAGG GGCAGTAGGG GACGAGGGAA CGGCATAGAA
5281 GAAACTATTT GTACCGCGTC CGCCAAGAAG AATATTGGGC GAAACCGCAG TCCCGACATA
5341 TACAATCCTC AAGCCGGCAG CCTTAAAACC GCCAACGATC TGAACCTGCT GATCCTCCGC
5401 TGGCTGGGCC CAAGCGCCGA ATATGGGAAT CTGTACCGAA ATGCCTGTGT TGTGCCCCAC
5461 TACAATACAA ATGCCCACTC TATTATCTAC CGCCTCGAGG GGAGGGCTCA TGTGCAAGTG
5521 GTCGACAGCA ATGGGAATCG CGTGTACGAT GAGGAGCTCC AAGAAGGGCA TGTCCTTGTT
5581 GTGCCTCAGA ATTTCGCAGT TGCGGGCAAA TCACAGAGTG AGAACTTCGA GTACGTTGCC
5641 TTTAAGACCG ATTCCAGACC CTCCATTGCA AACCTGGCCG GAGAGAACAG TGTTATTGAC
5701 AATCTGCCGG AGGAAGTGGT TGCTAACAGT TATGGGCTTC AGCGCGAACA GGCTCGGCAG
5761 CTGAAGAACA ACAATCCGTT CAAGTTTTTC GTCCCTCCAT CCCAGCAGTC ACCCAGAGCT
5821 GTGGCCGCCA AATCCACTAT TCTTGTGGCC CTCTTGGCAC TCGTGCTGGT CGCCCATGCT
5881 TCTGCTATGC GAAGGGAGAG AGGGCGCCAA GGTGACTCAA GCAGTTGCGA ACGACAAGTG
5941 GACAGAGTGA ACCTCAAACC TTGCGAACAG CACATTATGC AGAGAATTAT GGGAGAGCAA
6001 GAGCAGTATG ATAGTTATGA TATCAGATCA ACACGCTCTT CCGATCAGCA ACAGCGGTGT
6061 TGCGATGAAC TCAACGAAAT GGAGAATACG CAGCGGTGCA TGTGTGAGGC TCTTCAGCAA
6121 ATCATGGAAA ACCAATGCGA TCGGCTCCAA GATCGACAGA TGGTGCAGCA GTTTAAGCGC
6181 GAGCTGATGA ATTTGCCACA ACAGTGCAAC TTTCGGGCTC CCCAGAGATG CGACCTCGAT
6241 GTCAGCGGAG GGAGATGCTA ATTTTTATCC TGCAGGacttcgaaaccgttatttatagca
6301 gatatagggataggagtaggaatgccacaaatgaaaaaaatacttaaaatgtaatcttaa
6361 tcgagtacaccacacgacaatgaacaaacctaagacagattatgctggttatgcttgctg
6421 cgtaatatgcggtctaattgtcggaattattttacagcgacactattaaaagttgtaga
6481 acgtaaattagttcatacaccatcaatagataaaacgataaaagatgcatatattagaga
6541 agattgtcctactgactggataagctataataataaaatgtatccatttatctactgatcg
6601 aaaaacctgggaggaaggacgtaatacatgcaaagctctaaatccaaattcggatctaat
6661 taagatagagactccaaacgagttaagttttttaagaagccttagacgaggctattgggt
6721 aggagaatccgaaatattaaaccagacaaccccatataatttttatagctaaaaatgcGCG
6781 GCCGC
```

Group B is significantly greater than group A (p < 0.005)

SEQUENCE LISTING

<160> NUMBER OF SEQ ID NOS: 28

<210> SEQ ID NO 1
<211> LENGTH: 228
<212> TYPE: DNA
<213> ORGANISM: Artificial Sequence
<220> FEATURE:
<223> OTHER INFORMATION: Modified Ubiquitin C monomer

<400> SEQUENCE: 1

```
atgcagatct ttgtgaaaac actcacggga aaaactataa ctcttgaggt ggagccctct      60
gacacaatcg aaaatgtgaa agccaagatc caagataagg aaggcatccc tccagaccag     120
caacggctca tctttgcggg caaacaactg gaggatgggc gcactctcag tgattacaat     180
attcaaaagg aatctacact gcacctggtt cttaggctgc ggggagcc                  228
```

<210> SEQ ID NO 2
<211> LENGTH: 76
<212> TYPE: PRT
<213> ORGANISM: Artificial Sequence
<220> FEATURE:
<223> OTHER INFORMATION: Modified Ubiquitin C monomer

<400> SEQUENCE: 2

```
Met Gln Ile Phe Val Lys Thr Leu Thr Gly Lys Thr Ile Thr Leu Glu
1               5                   10                  15

Val Glu Pro Ser Asp Thr Ile Glu Asn Val Lys Ala Lys Ile Gln Asp
            20                  25                  30
Lys Glu Gly Ile Pro Pro Asp Gln Gln Arg Leu Ile Phe Ala Gly Lys
        35                  40                  45
Gln Leu Glu Asp Gly Arg Thr Leu Ser Asp Tyr Asn Ile Gln Lys Glu
    50                  55                  60
Ser Thr Leu His Leu Val Leu Arg Leu Arg Gly Ala
65                  70                  75
```

<210> SEQ ID NO 3
<211> LENGTH: 1875
<212> TYPE: DNA
<213> ORGANISM: Artificial Sequence
<220> FEATURE:
<223> OTHER INFORMATION: Modified Ara h1

<400> SEQUENCE: 3

```
cgaggcagag tcagccctct gatgctgctg ttggggatct tggttcttgc atccgtttca      60
gccacacatg ccaagtccag cccataccag aaaaagaccg agaacccatg tgctcagcgg     120
tgcctccagt catgtcagca ggaacccgat gacctcaagc aaaaggcgtg tgaaagcaga     180
tgtacgaaac tggaatacga ccccagatgc gtgtacgatc cacgaggcca tactggcacc     240
accaatcaaa gatcaccacc tggcgagcga accaggggac gacagccagg ggattacgat     300
gacgatagac gacagcctcg ccgggaagag ggtgggcgct ggggtccagc cggtcccaga     360
gagcgagaac gggaagagga ctggcgccaa ccccgggagg actggcgcag accttcacac     420
cagcagcccc ggaaaatacg cccggagggc agagagggtg aacaggaatg gggaacccct     480
ggcagtcacg tcagggaaga aaccagccgg aacaacccct tctatttccc ctcccggagg     540
tttagcactc ggtacgggaa ccaaaacgga cgcattcgcg tacttcagag atttgatcaa     600
cgctcacggc agttccagaa ccttcaaaac catcggattg ttcagatcga ggccaaacca     660
aacactttgg ttctgccaaa acatgctgat gcagacaaca tactggtgat acagcagggt     720
```

-continued

```
caagccacag tgacagtagc caatgggaac aatcgcaaat cattcaatct cgatgaggga    780
cacgcactga ggatcccttc tggctttatc tcctatatac tgaatcggca cgacaatcaa    840
aatctcaggg ttgctaagat ctctatgcca gtcaacactc cgggtcagtt cgaggatttc    900
tttcccgcgt cctcacggga ccagtctagt tatcttcaag gattcagcag aaacaccttg    960
gaagcggcct ttaacgccga gtttaacgag atcaggcggg tgcttctcga ggagaacgct   1020
ggcggggaac aggaggagag aggccaacgg cggtggtcta ccaggtccag tgagaacaat   1080
gagggcgtga tcgtcaaggt atctaaggag catgtcgagg aactgaccaa acatgcaaag   1140
tccgtttcca agaaaggctc cgaggaggaa ggggacatta cgaatccgat caaccttcgg   1200
gagggcgagc cggatctgtc aaataacttt ggaaaactct tcgaagtcaa gcccgacaaa   1260
aagaatccgc agttgcaaga tctggacatg atgctcacgt gtgtcgagat taaggaagga   1320
gcactgatgt tgcctcactt taactccaaa gccatggtga tagtcgtagt aaacaaagga   1380
accggcaatc tggagttggt ggctgtccga aaggaacaac agcaaagagg gcggagggaa   1440
gaagaggaag atgaggacga ggaggaggag ggatcaaacc gggaggtacg ccgatacaca   1500
gcgaggctga agagggaga cgtgtttatc atgccggcag cacatcctgt cgctatcaac   1560
gcctctagcg agctccattt gctggggttc gggatcaatg cggagaacaa tcatcgcatt   1620
ttcctggcag cgacaagga caacgttatt gaccaaattg agaagcaagc caaggacctg   1680
gccttccctg gatcaggtga acaggtcgag aagctcatca aaaaccagaa ggaatcccac   1740
tttgtatctg ccagaccaca gtcacagtcc cagagcccct ctagtcccga aggagagagc   1800
cccgaaaagg aagatcaaga ggaggagaac cagggtggaa agggcccact gctttccatt   1860
ctcaaagcct tcaat                                                   1875
```

<210> SEQ ID NO 4
<211> LENGTH: 625
<212> TYPE: PRT
<213> ORGANISM: Artificial Sequence
<220> FEATURE:
<223> OTHER INFORMATION: Modified Ara h1

<400> SEQUENCE: 4

```
Arg Gly Arg Val Ser Pro Leu Met Leu Leu Gly Ile Leu Val Leu
1               5                   10                  15

Ala Ser Val Ser Ala Thr His Ala Lys Ser Ser Pro Tyr Gln Lys Lys
            20                  25                  30

Thr Glu Asn Pro Cys Ala Gln Arg Cys Leu Gln Ser Cys Gln Gln Glu
        35                  40                  45

Pro Asp Asp Leu Lys Gln Lys Ala Cys Glu Ser Arg Cys Thr Lys Leu
    50                  55                  60

Glu Tyr Asp Pro Arg Cys Val Tyr Asp Pro Gly His Thr Gly Thr
65                  70                  75                  80

Thr Asn Gln Arg Ser Pro Pro Gly Glu Arg Thr Arg Gly Arg Gln Pro
                85                  90                  95

Gly Asp Tyr Asp Asp Asp Arg Arg Gln Pro Arg Arg Glu Glu Gly Gly
            100                 105                 110

Arg Trp Gly Pro Ala Gly Pro Arg Glu Arg Glu Arg Glu Glu Asp Trp
        115                 120                 125

Arg Gln Pro Arg Glu Asp Trp Arg Arg Pro Ser His Gln Gln Pro Arg
    130                 135                 140

Lys Ile Arg Pro Glu Gly Arg Glu Gly Glu Gln Glu Trp Gly Thr Pro
145                 150                 155                 160
```

```
Gly Ser His Val Arg Glu Glu Thr Ser Arg Asn Asn Pro Phe Tyr Phe
                165                 170                 175

Pro Ser Arg Arg Phe Ser Thr Arg Tyr Gly Asn Gln Asn Gly Arg Ile
            180                 185                 190

Arg Val Leu Gln Arg Phe Asp Gln Arg Ser Arg Gln Phe Gln Asn Leu
        195                 200                 205

Gln Asn His Arg Ile Val Gln Ile Glu Ala Lys Pro Asn Thr Leu Val
    210                 215                 220

Leu Pro Lys His Ala Asp Ala Asp Asn Ile Leu Val Ile Gln Gln Gly
225                 230                 235                 240

Gln Ala Thr Val Thr Val Ala Asn Gly Asn Asn Arg Lys Ser Phe Asn
                245                 250                 255

Leu Asp Glu Gly His Ala Leu Arg Ile Pro Ser Gly Phe Ile Ser Tyr
            260                 265                 270

Ile Leu Asn Arg His Asp Asn Gln Asn Leu Arg Val Ala Lys Ile Ser
        275                 280                 285

Met Pro Val Asn Thr Pro Gly Gln Phe Glu Asp Phe Phe Pro Ala Ser
    290                 295                 300

Ser Arg Asp Gln Ser Ser Tyr Leu Gln Gly Phe Ser Arg Asn Thr Leu
305                 310                 315                 320

Glu Ala Ala Phe Asn Ala Glu Phe Asn Glu Ile Arg Arg Val Leu Leu
                325                 330                 335

Glu Glu Asn Ala Gly Gly Glu Gln Glu Glu Arg Gly Gln Arg Arg Trp
            340                 345                 350

Ser Thr Arg Ser Ser Glu Asn Asn Glu Gly Val Ile Val Lys Val Ser
        355                 360                 365

Lys Glu His Val Glu Glu Leu Thr Lys His Ala Lys Ser Val Ser Lys
    370                 375                 380

Lys Gly Ser Glu Glu Glu Gly Asp Ile Thr Asn Pro Ile Asn Leu Arg
385                 390                 395                 400

Glu Gly Glu Pro Asp Leu Ser Asn Asn Phe Gly Lys Leu Phe Glu Val
                405                 410                 415

Lys Pro Asp Lys Lys Asn Pro Gln Leu Gln Asp Leu Asp Met Met Leu
            420                 425                 430

Thr Cys Val Glu Ile Lys Glu Gly Ala Leu Met Leu Pro His Phe Asn
        435                 440                 445

Ser Lys Ala Met Val Ile Val Val Asn Lys Gly Thr Gly Asn Leu
    450                 455                 460

Glu Leu Val Ala Val Arg Lys Glu Gln Gln Arg Gly Arg Arg Glu
465                 470                 475                 480

Glu Glu Glu Asp Glu Asp Glu Glu Glu Gly Ser Asn Arg Glu Val
                485                 490                 495

Arg Arg Tyr Thr Ala Arg Leu Lys Glu Gly Asp Val Phe Ile Met Pro
            500                 505                 510

Ala Ala His Pro Val Ala Ile Asn Ala Ser Ser Glu Leu His Leu Leu
        515                 520                 525

Gly Phe Gly Ile Asn Ala Glu Asn Asn His Arg Ile Phe Leu Ala Gly
    530                 535                 540

Asp Lys Asp Asn Val Ile Asp Gln Ile Glu Lys Gln Ala Lys Asp Leu
545                 550                 555                 560

Ala Phe Pro Gly Ser Gly Glu Gln Val Glu Lys Leu Ile Lys Asn Gln
                565                 570                 575
```

-continued

```
Lys Glu Ser His Phe Val Ser Ala Arg Pro Gln Ser Gln Ser Gln Ser
            580                 585                 590
Pro Ser Ser Pro Glu Lys Glu Ser Pro Glu Lys Glu Asp Gln Glu Glu
        595                 600                 605
Glu Asn Gln Gly Gly Lys Gly Pro Leu Leu Ser Ile Leu Lys Ala Phe
    610                 615                 620
Asn
625

<210> SEQ ID NO 5
<211> LENGTH: 513
<212> TYPE: DNA
<213> ORGANISM: Artificial Sequence
<220> FEATURE:
<223> OTHER INFORMATION: Modified Ara h2

<400> SEQUENCE: 5
gctaagctga caatattggt ggcactggca ctgttccttc ttgctgcaca cgcgtcagcc     60
cggcagcagt gggaattgca gggcgatcga aggtgtcagt cacagctgga gagggcgaac    120
ctccggcctt gtgaacagca cctgatgcag aagattcagc gggacgagga ttcttacggg    180
cgagatcctt acagtccctc ccaagatcca tatagcccgt ctcaagaccc agatcgcagg    240
gacccatata gccccagccc ctatgatcga agaggtgccg gaagcagcca gcatcaggaa    300
aggtgctgca atgagctgaa cgagttcgag aacaaccaga gatgtatgtg cgaggctctg    360
cagcagatta tggaaaatca atctgaccgg ctgcagggac ggcagcagga gcagcagttc    420
aaaagggagc tccgcaacct tccacagcag tgcggtttgc gcgcacctca gcgctgcgac    480
ttggaggtgg aaagcggagg tagagacaga tac                                 513

<210> SEQ ID NO 6
<211> LENGTH: 171
<212> TYPE: PRT
<213> ORGANISM: Artificial Sequence
<220> FEATURE:
<223> OTHER INFORMATION: Modified Ara h2

<400> SEQUENCE: 6

Ala Lys Leu Thr Ile Leu Val Ala Leu Ala Leu Phe Leu Leu Ala Ala
1               5                   10                  15
His Ala Ser Ala Arg Gln Gln Trp Glu Leu Gln Gly Asp Arg Arg Cys
            20                  25                  30

Gln Ser Gln Leu Glu Arg Ala Asn Leu Arg Pro Cys Glu Gln His Leu
        35                  40                  45

Met Gln Lys Ile Gln Arg Asp Glu Asp Ser Tyr Gly Arg Asp Pro Tyr
    50                  55                  60

Ser Pro Ser Gln Asp Pro Tyr Ser Pro Ser Gln Asp Pro Asp Arg Arg
65                  70                  75                  80

Asp Pro Tyr Ser Pro Ser Pro Tyr Asp Arg Arg Gly Ala Gly Ser Ser
                85                  90                  95

Gln His Gln Glu Arg Cys Cys Asn Glu Leu Asn Glu Phe Glu Asn Asn
            100                 105                 110

Gln Arg Cys Met Cys Glu Ala Leu Gln Gln Ile Met Glu Asn Gln Ser
        115                 120                 125

Asp Arg Leu Gln Gly Arg Gln Gln Glu Gln Gln Phe Lys Arg Glu Leu
    130                 135                 140

Arg Asn Leu Pro Gln Gln Cys Gly Leu Arg Ala Pro Gln Arg Cys Asp
145                 150                 155                 160
```

Leu Glu Val Glu Ser Gly Gly Arg Asp Arg Tyr
            165                 170

<210> SEQ ID NO 7
<211> LENGTH: 1587
<212> TYPE: DNA
<213> ORGANISM: Artificial Sequence
<220> FEATURE:
<223> OTHER INFORMATION: Modified Ara h3

<400> SEQUENCE: 7

| | | | | |
|---|---|---|---|---|
| gcgaagctgc | tggaactcag | cttctgtttc | tgtttcctgg | tactcggcgc | ttcatcaata | 60 |
| tcttttaggc | agcagccaga | ggaaaatgcc | tgccagttcc | aacggctgaa | cgctcagcga | 120 |
| ccagacaata | ggatcgaatc | agaaggtgga | tacatcgaga | cttggaaccc | gaataaccag | 180 |
| gagttcgaat | gtgcaggcgt | ggcactgtct | cgccttgttc | tccgacgcaa | tgcgctcagg | 240 |
| cgcccattct | attccaatgc | accccaagaa | atctttatcc | aacagggcag | agggtacttc | 300 |
| gggctgatct | ttcccggctg | tccccggcac | tatgaggaac | ccacacaca | gggcagaagg | 360 |
| agccagagcc | agcggcctcc | ccggagattg | caaggggagg | atcagagcca | gcagcagaga | 420 |
| gattctcatc | agaaagtaca | taggttcgat | gagggtgacc | tgatagctgt | gccaaccggt | 480 |
| gttgcctttt | ggttgtataa | tgaccacgac | acagacgtgg | tggctgtgtc | tctgaccgat | 540 |
| acaaacaaca | atgacaatca | gcttgatcag | ttccctaggc | gctttaacct | ggctggcaac | 600 |
| accgaacagg | agttcttgag | atatcagcag | cagtctaggc | agtctaggag | gaggtccctg | 660 |
| ccatactccc | cttacagccc | tcagagtcag | cctaggcagg | aagagagaga | attcagtccc | 720 |
| agaggccagc | actctaggcg | ggagcgggct | gggcaggagg | aggaaaacga | aggtggcaat | 780 |
| atctttagcg | gcttcactcc | agagtttctg | gaacaggcat | tccaagtaga | tgacagacag | 840 |
| atcgtccaga | accttagggg | cgagactgaa | tcagaagagg | aaggggcaat | cgtgacggtg | 900 |
| cgcggaggct | tgcgcatcct | gtcccctgac | cgcaaacgca | gggccgacga | ggaagaagag | 960 |
| tatgacgagg | atgaatatga | atatgatgag | gaggatcgaa | ggcgcggaag | gggcagtagg | 1020 |
| ggacgaggga | acggcataga | agaaactatt | tgtaccgcgt | ccgccaagaa | gaatattggg | 1080 |
| cgaaaccgca | gtcccgacat | atacaatcct | caagccggca | gccttaaaac | cgccaacgat | 1140 |
| ctgaacctgc | tgatcctccg | ctggctgggg | ccaagcgccg | aatatgggaa | tctgtaccga | 1200 |
| aatgctctgt | tgtggcccca | ctacaataca | aatgcccact | ctattatcta | ccgcctcaga | 1260 |
| gggagggctc | atgtgcaagt | ggtcgacagc | aatgggaatc | gcgtgtacga | tgaggagctc | 1320 |
| caagaagggc | atgtccttgt | tgtgcctcag | aatttcgcag | ttgcgggcaa | atcacagagt | 1380 |
| gagaacttcg | agtacgttgc | ctttaagacc | gattccagac | cctccattgc | aaacctggcc | 1440 |
| ggagagaaca | gtgttattga | caatctgccg | gaggaagtgg | ttgctaacag | ttatgggctt | 1500 |
| cagcgcgaac | aggctcggca | gctgaagaac | aacaatccgt | tcaagttttt | cgtccctcca | 1560 |
| tcccagcagt | cacccagagc | tgtggcc | | | | 1587 |

<210> SEQ ID NO 8
<211> LENGTH: 529
<212> TYPE: PRT
<213> ORGANISM: Artificial Sequence
<220> FEATURE:
<223> OTHER INFORMATION: Modified Ara h3

<400> SEQUENCE: 8

Ala Lys Leu Leu Glu Leu Ser Phe Cys Phe Cys Phe Leu Val Leu Gly

```
1               5                   10                  15
Ala Ser Ser Ile Ser Phe Arg Gln Gln Pro Glu Glu Asn Ala Cys Gln
                20                  25                  30

Phe Gln Arg Leu Asn Ala Gln Arg Pro Asp Asn Arg Ile Glu Ser Glu
                35                  40                  45

Gly Gly Tyr Ile Glu Thr Trp Asn Pro Asn Asn Gln Glu Phe Glu Cys
                50                  55                  60

Ala Gly Val Ala Leu Ser Arg Leu Val Leu Arg Arg Asn Ala Leu Arg
65                  70                  75                  80

Arg Pro Phe Tyr Ser Asn Ala Pro Gln Glu Ile Phe Ile Gln Gln Gly
                85                  90                  95

Arg Gly Tyr Phe Gly Leu Ile Phe Pro Gly Cys Pro Arg His Tyr Glu
                100                 105                 110

Glu Pro His Thr Gln Gly Arg Arg Ser Gln Ser Gln Arg Pro Pro Arg
                115                 120                 125

Arg Leu Gln Gly Glu Asp Gln Ser Gln Gln Arg Asp Ser His Gln
                130                 135                 140

Lys Val His Arg Phe Asp Glu Gly Asp Leu Ile Ala Val Pro Thr Gly
145                 150                 155                 160

Val Ala Phe Trp Leu Tyr Asn Asp His Asp Thr Asp Val Val Ala Val
                165                 170                 175

Ser Leu Thr Asp Thr Asn Asn Asn Asp Asn Gln Leu Asp Gln Phe Pro
                180                 185                 190

Arg Arg Phe Asn Leu Ala Gly Asn Thr Glu Gln Glu Phe Leu Arg Tyr
                195                 200                 205

Gln Gln Gln Ser Arg Gln Ser Arg Arg Ser Leu Pro Tyr Ser Pro
                210                 215                 220

Tyr Ser Pro Gln Ser Gln Pro Arg Gln Glu Arg Glu Phe Ser Pro
225                 230                 235                 240

Arg Gly Gln His Ser Arg Arg Glu Arg Ala Gly Gln Glu Glu Glu Asn
                245                 250                 255

Glu Gly Gly Asn Ile Phe Ser Gly Phe Thr Pro Glu Phe Leu Glu Gln
                260                 265                 270

Ala Phe Gln Val Asp Asp Arg Gln Ile Val Gln Asn Leu Arg Gly Glu
                275                 280                 285

Thr Glu Ser Glu Glu Gly Ala Ile Val Thr Val Arg Gly Gly Leu
                290                 295                 300

Arg Ile Leu Ser Pro Asp Arg Lys Arg Arg Ala Asp Glu Glu Glu Glu
305                 310                 315                 320

Tyr Asp Glu Asp Glu Tyr Glu Tyr Asp Glu Asp Arg Arg Gly
                325                 330                 335

Arg Gly Ser Arg Gly Arg Gly Asn Gly Ile Glu Glu Thr Ile Cys Thr
                340                 345                 350

Ala Ser Ala Lys Lys Asn Ile Gly Arg Asn Arg Ser Pro Asp Ile Tyr
                355                 360                 365

Asn Pro Gln Ala Gly Ser Leu Lys Thr Ala Asn Asp Leu Asn Leu Leu
                370                 375                 380

Ile Leu Arg Trp Leu Gly Pro Ser Ala Glu Tyr Gly Asn Leu Tyr Arg
385                 390                 395                 400

Asn Ala Leu Phe Val Ala His Tyr Asn Thr Asn Ala His Ser Ile Ile
                405                 410                 415

Tyr Arg Leu Arg Gly Arg Ala His Val Gln Val Val Asp Ser Asn Gly
                420                 425                 430
```

```
Asn Arg Val Tyr Asp Glu Glu Leu Gln Glu Gly His Val Leu Val Val
        435                 440                 445

Pro Gln Asn Phe Ala Val Ala Gly Lys Ser Gln Ser Glu Asn Phe Glu
    450                 455                 460

Tyr Val Ala Phe Lys Thr Asp Ser Arg Pro Ser Ile Ala Asn Leu Ala
465                 470                 475                 480

Gly Glu Asn Ser Val Ile Asp Asn Leu Pro Glu Glu Val Val Ala Asn
                485                 490                 495

Ser Tyr Gly Leu Gln Arg Glu Gln Ala Arg Gln Leu Lys Asn Asn Asn
                500                 505                 510

Pro Phe Lys Phe Val Pro Pro Ser Gln Gln Ser Pro Arg Ala Val
        515                 520                 525

Ala

<210> SEQ ID NO 9
<211> LENGTH: 435
<212> TYPE: DNA
<213> ORGANISM: Artificial Sequence
<220> FEATURE:
<223> OTHER INFORMATION: Modified Ara h6

<400> SEQUENCE: 9
gccaaatcca ctattcttgt ggccctcttg gcactcgtgc tggtcgccca tgcttctgct     60
atgcgaaggg agagagggcg ccaaggtgac tcaagcagtt gcgaacgaca agtggacaga   120
gtgaacctca aaccttgcga acagcacatt atgcagagaa ttatgggaga gcaagagcag   180
tatgatagtt atgatatcag atcaacacgc tcttccgatc agcaacagcg tgttgcgat    240
gaactcaacg aaatggagaa tacgcagcgg tgcatgtgtg aggctcttca gcaaatcatg   300
gaaaaccaat gcgatcggct ccaagatcga cagatggtgc agcagtttaa gcgcgagctg   360
atgaatttgc cacaacagtg caactttcgg gctccccaga gatgcgacct cgatgtcagc   420
ggagggagat gctaa                                                    435

<210> SEQ ID NO 10
<211> LENGTH: 144
<212> TYPE: PRT
<213> ORGANISM: Artificial Sequence
<220> FEATURE:
<223> OTHER INFORMATION: Modified Ara h6

<400> SEQUENCE: 10

Ala Lys Ser Thr Ile Leu Val Ala Leu Leu Ala Leu Val Leu Val Ala
1               5                   10                  15

His Ala Ser Ala Met Arg Arg Glu Arg Gly Arg Gln Gly Asp Ser Ser
            20                  25                  30

Ser Cys Glu Arg Gln Val Asp Arg Val Asn Leu Lys Pro Cys Glu Gln
        35                  40                  45

His Ile Met Gln Arg Ile Met Gly Glu Gln Glu Gln Tyr Asp Ser Tyr
    50                  55                  60

Asp Ile Arg Ser Thr Arg Ser Ser Asp Gln Gln Gln Arg Cys Cys Asp
65                  70                  75                  80

Glu Leu Asn Glu Met Glu Asn Thr Gln Arg Cys Met Cys Glu Ala Leu
                85                  90                  95

Gln Gln Ile Met Glu Asn Gln Cys Asp Arg Leu Gln Asp Arg Gln Met
            100                 105                 110

Val Gln Gln Phe Lys Arg Glu Leu Met Asn Leu Pro Gln Gln Cys Asn
```

```
            115                 120                 125
Phe Arg Ala Pro Gln Arg Cys Asp Leu Asp Val Ser Gly Gly Arg Cys
    130                 135                 140
```

<210> SEQ ID NO 11
<211> LENGTH: 4638
<212> TYPE: DNA
<213> ORGANISM: Artificial Sequence
<220> FEATURE:
<223> OTHER INFORMATION: PHAVag sequence

<400> SEQUENCE: 11

| | | | | |
|---|---|---|---|---|
| atgcagatct | tgtgaaaaac | actcacggga | aaaactataa | ctcttgaggt ggagccctct | 60 |
| gacacaatcg | aaaatgtgaa | agccaagatc | aagataagg | aaggcatccc tccagaccag | 120 |
| caacggctca | tctttgcggg | caaac -continued

```
tcaggtgaac aggtcgagaa gctcatcaaa aaccagaagg aatcccactt tgtatctgcc    1980
agaccacagt cacagtccca gagcccctct agtcccgaga aggagagccc cgaaaaggaa    2040
gatcaagagg aggagaacca gggtggaaag ggcccactgc tttccattct caaagccttc    2100
aatgctaagc tgacaatatt ggtggcactg gcactgttcc ttcttgctgc acacgcgtca    2160
gcccggcagc agtgggaatt gcagggcgat cgaaggtgtc agtcacagct ggagagggcg    2220
aacctccggc cttgtgaaca gcacctgatg cagaagattc agcgggacga ggattcttac    2280
gggcgagatc cttacagtcc ctcccaagat ccatatagcc cgtctcaaga cccagatcgc    2340
agggacccat atagccccag cccctatgat cgaagaggtg ccggaagcag ccagcatcag    2400
gaaaggtgct gcaatgagct gaacgagttc gagaacaacc agagatgtat gtgcgaggct    2460
ctgcagcaga ttatggaaaa tcaatctgac cggctgcagg gacggcagca ggagcagcag    2520
ttcaaaaggg agctccgcaa ccttccacag cagtgcggtt gcgcgcacc tcagcgctgc    2580
gacttggagg tggaaagcgg aggtagagac agatacgcga agctgctgga actcagcttc    2640
tgtttctgtt tcctggtact cggcgcttca tcaatatctt ttaggcagca gccagaggaa    2700
aatgcctgcc agttccaacg gctgaacgct cagcgaccag acaataggat cgaatcagaa    2760
ggtggataca tcgagacttg gaacccgaat aaccaggagt tcgaatgtgc aggcgtggca    2820
ctgtctcgcc ttgttctccg acgcaatgcg ctcaggcgcc cattctattc caatgcaccc    2880
caagaaatct ttatccaaca gggcagaggg tacttcgggc tgatcttttcc cggctgtccc    2940
cggcactatg aggaacccca cacagggc agaaggagcc agagccagcg gcctccccgg    3000
agattgcaag gggaggatca gagccagcag cagagagatt ctcatcagaa agtacatagg    3060
ttcgatgagg gtgacctgat agctgtgcca accggtgttg cctttttggtt gtataatgac    3120
cacgacacag acgtggtggc tgtgtctctg accgatacaa acaacaatga caatcagctt    3180
gatcagttcc ctaggcgctt taacctggct ggcaacaccg aacaggagtt cttgagatat    3240
cagcagcagt ctaggcagtc taggaggagg tccctgccat actcccctta cagccctcag    3300
agtcagccta ggcaggaaga gagagaattc agtcccagag ccagcactc taggcgggag    3360
cgggctgggc aggaggagga aaacgaaggt ggcaatatct ttagcggctt cactccagag    3420
tttctggaac aggcattcca agtagatgac agacagatcg tccagaacct taggggcgag    3480
actgaatcag aagaggaagg ggcaatcgtg acggtgcgcg gaggcttgcg catcctgtcc    3540
cctgaccgca aacgcagggc cgacgaggaa gaagagtatg acgaggatga atatgaatat    3600
gatgaggagg atcgaaggcg cggaaggggc agtaggggac gagggaacgg catagaagaa    3660
actatttgta ccgcgtccgc caagaagaat attgggcgaa accgcagtcc cgacatatac    3720
aatcctcaag ccggcagcct taaaaccgcc aacgatctga acctgctgat cctccgctgg    3780
ctggggccaa gcgccgaata tgggaatctg taccgaaatg ctctgtttgt ggcccactac    3840
aatacaaatg cccactctat tatctaccgc ctcagaggga gggctcatgt gcaagtggtc    3900
gacagcaatg ggaatcgcgt gtacgatgag gagctccaag aagggcatgt ccttgttgtg    3960
cctcagaatt tcgcagttgc gggcaaatca cagagtgaga acttcgagta cgttgccttt    4020
aagaccgatt ccagaccctc cattgcaaac ctggccggag agaacagtgt tattgacaat    4080
ctgccggagg aagtggttgc taacagttat gggcttcagc gcgaacaggc tcggcagctg    4140
aagaacaaca atccgttcaa gttttttcgtc cctccatccc agcagtcacc cagagctgtg    4200
gccgccaaat ccactattct tgtggccctc ttggcactcg tgctggtcgc ccatgcttct    4260
gctatgcgaa gggagagagg gcgccaaggt gactcaagca gttgcgaacg acaagtggac    4320
```

```
agagtgaacc tcaaaccttg cgaacagcac attatgcaga gaattatggg agagcaagag   4380
cagtatgata gttatgatat cagatcaaca cgctcttccg atcagcaaca gcggtgttgc   4440
gatgaactca acgaaatgga gaatacgcag cggtgcatgt gtgaggctct tcagcaaatc   4500
atggaaaacc aatgcgatcg gctccaagat cgacagatgg tgcagcagtt taagcgcgag   4560
ctgatgaatt tgccacaaca gtgcaacttt cgggctcccc agagatgcga cctcgatgtc   4620
agcggaggga gatgctaa                                                 4638

<210> SEQ ID NO 12
<211> LENGTH: 1545
<212> TYPE: PRT
<213> ORGANISM: Artificial Sequence
<220> FEATURE:
<223> OTHER INFORMATION: PHAVag sequence
<400> SEQUENCE: 12

Met Gln Ile Phe Val Lys Thr Leu Thr Gly Lys Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Phe Ala Gly Lys
        35                  40                  45

Gln Leu Glu Asp Gly Arg Thr Leu Ser Asp Tyr Asn Ile Gln Lys Glu
    50                  55                  60

Ser Thr Leu His Leu Val Leu Arg Leu Arg Gly Ala Arg Gly Arg Val
65                  70                  75                  80

Ser Pro Leu Met Leu Leu Leu Gly Ile Leu Val Leu Ala Ser Val Ser
                85                  90                  95

Ala Thr His Ala Lys Ser Ser Pro Tyr Gln Lys Lys Thr Glu Asn Pro
            100                 105                 110

Cys Ala Gln Arg Cys Leu Gln Ser Cys Gln Gln Glu Pro Asp Asp Leu
        115                 120                 125

Lys Gln Lys Ala Cys Glu Ser Arg Cys Thr Lys Leu Glu Tyr Asp Pro
    130                 135                 140

Arg Cys Val Tyr Asp Pro Arg Gly His Thr Gly Thr Thr Asn Gln Arg
145                 150                 155                 160

Ser Pro Pro Gly Glu Arg Thr Arg Gly Arg Gln Pro Gly Asp Tyr Asp
                165                 170                 175

Asp Asp Arg Arg Gln Pro Arg Arg Glu Glu Gly Gly Arg Trp Gly Pro
            180                 185                 190

Ala Gly Pro Arg Glu Arg Glu Arg Glu Glu Asp Trp Arg Gln Pro Arg
        195                 200                 205

Glu Asp Trp Arg Arg Pro Ser His Gln Gln Pro Arg Lys Ile Arg Pro
    210                 215                 220

Glu Gly Arg Glu Gly Glu Gln Glu Trp Gly Thr Pro Gly Ser His Val
225                 230                 235                 240

Arg Glu Glu Thr Ser Arg Asn Asn Pro Phe Tyr Phe Pro Ser Arg Arg
                245                 250                 255

Phe Ser Thr Arg Tyr Gly Asn Gln Asn Gly Arg Ile Arg Val Leu Gln
            260                 265                 270

Arg Phe Asp Gln Arg Ser Arg Gln Phe Gln Asn Leu Gln Asn His Arg
        275                 280                 285

Ile Val Gln Ile Glu Ala Lys Pro Asn Thr Leu Val Leu Pro Lys His
    290                 295                 300
```

```
Ala Asp Ala Asp Asn Ile Leu Val Ile Gln Gln Gly Gln Ala Thr Val
305                 310                 315                 320

Thr Val Ala Asn Gly Asn Asn Arg Lys Ser Phe Asn Leu Asp Glu Gly
            325                 330                 335

His Ala Leu Arg Ile Pro Ser Gly Phe Ile Ser Tyr Ile Leu Asn Arg
            340                 345                 350

His Asp Asn Gln Asn Leu Arg Val Ala Lys Ile Ser Met Pro Val Asn
            355                 360                 365

Thr Pro Gly Gln Phe Glu Asp Phe Pro Ala Ser Ser Arg Asp Gln
370                 375                 380

Ser Ser Tyr Leu Gln Gly Phe Ser Arg Asn Thr Leu Glu Ala Ala Phe
385                 390                 395                 400

Asn Ala Glu Phe Asn Glu Ile Arg Arg Val Leu Leu Glu Glu Asn Ala
            405                 410                 415

Gly Gly Glu Gln Glu Glu Arg Gly Gln Arg Arg Trp Ser Thr Arg Ser
            420                 425                 430

Ser Glu Asn Asn Glu Gly Val Ile Val Lys Val Ser Lys Glu His Val
            435                 440                 445

Glu Glu Leu Thr Lys His Ala Lys Ser Val Ser Lys Lys Gly Ser Glu
450                 455                 460

Glu Glu Gly Asp Ile Thr Asn Pro Ile Asn Leu Arg Glu Gly Glu Pro
465                 470                 475                 480

Asp Leu Ser Asn Asn Phe Gly Lys Leu Phe Glu Val Lys Pro Asp Lys
            485                 490                 495

Lys Asn Pro Gln Leu Gln Asp Leu Asp Met Met Leu Thr Cys Val Glu
            500                 505                 510

Ile Lys Glu Gly Ala Leu Met Leu Pro His Phe Asn Ser Lys Ala Met
            515                 520                 525

Val Ile Val Val Asn Lys Gly Thr Gly Asn Leu Glu Leu Val Ala
530                 535                 540

Val Arg Lys Glu Gln Gln Gln Arg Gly Arg Arg Glu Glu Glu Glu Asp
545                 550                 555                 560

Glu Asp Glu Glu Glu Gly Ser Asn Arg Glu Val Arg Arg Tyr Thr
            565                 570                 575

Ala Arg Leu Lys Glu Gly Asp Val Phe Ile Met Pro Ala Ala His Pro
            580                 585                 590

Val Ala Ile Asn Ala Ser Ser Glu Leu His Leu Leu Gly Phe Gly Ile
            595                 600                 605

Asn Ala Glu Asn Asn His Arg Ile Phe Leu Ala Gly Asp Lys Asp Asn
            610                 615                 620

Val Ile Asp Gln Ile Glu Lys Gln Ala Lys Asp Leu Ala Phe Pro Gly
625                 630                 635                 640

Ser Gly Glu Gln Val Glu Lys Leu Ile Lys Asn Gln Lys Glu Ser His
            645                 650                 655

Phe Val Ser Ala Arg Pro Gln Ser Gln Ser Gln Ser Pro Ser Ser Pro
            660                 665                 670

Glu Lys Glu Ser Pro Glu Lys Glu Asp Gln Glu Glu Glu Asn Gln Gly
            675                 680                 685

Gly Lys Gly Pro Leu Leu Ser Ile Leu Lys Ala Phe Asn Ala Lys Leu
            690                 695                 700

Thr Ile Leu Val Ala Leu Ala Leu Phe Leu Leu Ala Ala His Ala Ser
705                 710                 715                 720
```

Ala Arg Gln Gln Trp Glu Leu Gln Gly Asp Arg Cys Gln Ser Gln
            725                 730                 735

Leu Glu Arg Ala Asn Leu Arg Pro Cys Glu Gln His Leu Met Gln Lys
            740                 745                 750

Ile Gln Arg Asp Glu Asp Ser Tyr Gly Arg Asp Pro Tyr Ser Pro Ser
            755                 760                 765

Gln Asp Pro Tyr Ser Pro Ser Gln Asp Pro Arg Arg Asp Pro Tyr
            770                 775                 780

Ser Pro Ser Pro Tyr Asp Arg Arg Gly Ala Gly Ser Ser Gln His Gln
785                 790                 795                 800

Glu Arg Cys Cys Asn Glu Leu Asn Glu Phe Glu Asn Asn Gln Arg Cys
                805                 810                 815

Met Cys Glu Ala Leu Gln Gln Ile Met Glu Asn Gln Ser Asp Arg Leu
                820                 825                 830

Gln Gly Arg Gln Gln Glu Gln Phe Lys Arg Glu Leu Arg Asn Leu
            835                 840                 845

Pro Gln Gln Cys Gly Leu Arg Ala Pro Gln Arg Cys Asp Leu Glu Val
            850                 855                 860

Glu Ser Gly Gly Arg Asp Arg Tyr Ala Lys Leu Leu Glu Leu Ser Phe
865                 870                 875                 880

Cys Phe Cys Phe Leu Val Leu Gly Ala Ser Ser Ile Ser Phe Arg Gln
                885                 890                 895

Gln Pro Glu Glu Asn Ala Cys Gln Phe Gln Arg Leu Asn Ala Gln Arg
            900                 905                 910

Pro Asp Asn Arg Ile Glu Ser Glu Gly Gly Tyr Ile Glu Thr Trp Asn
            915                 920                 925

Pro Asn Asn Gln Glu Phe Glu Cys Ala Gly Val Ala Leu Ser Arg Leu
            930                 935                 940

Val Leu Arg Arg Asn Ala Leu Arg Arg Pro Phe Tyr Ser Asn Ala Pro
945                 950                 955                 960

Gln Glu Ile Phe Ile Gln Gln Gly Arg Gly Tyr Phe Gly Leu Ile Phe
            965                 970                 975

Pro Gly Cys Pro Arg His Tyr Glu Glu Pro His Thr Gln Gly Arg Arg
            980                 985                 990

Ser Gln Ser Gln Arg Pro Pro Arg Arg Leu Gln Gly Glu Asp Gln Ser
            995                 1000                1005

Gln Gln Gln Arg Asp Ser His Gln Lys Val His Arg Phe Asp Glu Gly
            1010                1015                1020

Asp Leu Ile Ala Val Pro Thr Gly Val Ala Phe Trp Leu Tyr Asn Asp
1025                1030                1035                1040

His Asp Thr Asp Val Val Ala Val Ser Leu Thr Asp Thr Asn Asn
                1045                1050                1055

Asp Asn Gln Leu Asp Gln Phe Pro Arg Arg Phe Asn Leu Ala Gly Asn
            1060                1065                1070

Thr Glu Gln Glu Phe Leu Arg Tyr Gln Gln Ser Arg Gln Ser Arg
            1075                1080                1085

Arg Arg Ser Leu Pro Tyr Ser Pro Tyr Ser Pro Gln Ser Gln Pro Arg
1090                1095                1100

Gln Glu Glu Arg Glu Phe Ser Pro Arg Gly His Ser Arg Arg Glu
            1105                1110                1115                1120

Arg Ala Gly Gln Glu Glu Glu Asn Glu Gly Gly Asn Ile Phe Ser Gly
            1125                1130                1135

Phe Thr Pro Glu Phe Leu Glu Gln Ala Phe Gln Val Asp Asp Arg Gln

Ile Val Gln Asn Leu Arg Gly Glu Thr Glu Ser Glu Glu Glu Gly Ala
            1155                1160                1165

Ile Val Thr Val Arg Gly Gly Leu Arg Ile Leu Ser Pro Asp Arg Lys
        1170                1175                1180

Arg Arg Ala Asp Glu Glu Glu Tyr Asp Glu Asp Glu Tyr Glu Tyr
1185                1190                1195                1200

Asp Glu Glu Asp Arg Arg Gly Arg Gly Ser Arg Gly Arg Gly Asn
                1205                1210                1215

Gly Ile Glu Glu Thr Ile Cys Thr Ala Ser Ala Lys Lys Asn Ile Gly
            1220                1225                1230

Arg Asn Arg Ser Pro Asp Ile Tyr Asn Pro Gln Ala Gly Ser Leu Lys
        1235                1240                1245

Thr Ala Asn Asp Leu Asn Leu Leu Ile Leu Arg Trp Leu Gly Pro Ser
    1250                1255                1260

Ala Glu Tyr Gly Asn Leu Tyr Arg Asn Ala Leu Phe Val Ala His Tyr
1265                1270                1275                1280

Asn Thr Asn Ala His Ser Ile Ile Tyr Arg Leu Arg Gly Arg Ala His
                1285                1290                1295

Val Gln Val Val Asp Ser Asn Gly Asn Arg Val Tyr Asp Glu Glu Leu
            1300                1305                1310

Gln Glu Gly His Val Leu Val Val Pro Gln Asn Phe Ala Val Ala Gly
        1315                1320                1325

Lys Ser Gln Ser Glu Asn Phe Glu Tyr Val Ala Phe Lys Thr Asp Ser
    1330                1335                1340

Arg Pro Ser Ile Ala Asn Leu Ala Gly Glu Asn Ser Val Ile Asp Asn
1345                1350                1355                1360

Leu Pro Glu Glu Val Val Ala Asn Ser Tyr Gly Leu Gln Arg Glu Gln
                1365                1370                1375

Ala Arg Gln Leu Lys Asn Asn Asn Pro Phe Lys Phe Phe Val Pro Pro
            1380                1385                1390

Ser Gln Gln Ser Pro Arg Ala Val Ala Ala Lys Ser Thr Ile Leu Val
        1395                1400                1405

Ala Leu Leu Ala Leu Val Leu Val Ala His Ala Ser Ala Met Arg Arg
    1410                1415                1420

Glu Arg Gly Arg Gln Gly Asp Ser Ser Ser Cys Glu Arg Gln Val Asp
1425                1430                1435                1440

Arg Val Asn Leu Lys Pro Cys Glu Gln His Ile Met Gln Arg Ile Met
                1445                1450                1455

Gly Glu Gln Glu Gln Tyr Asp Ser Tyr Asp Ile Arg Ser Thr Arg Ser
            1460                1465                1470

Ser Asp Gln Gln Gln Arg Cys Cys Asp Glu Leu Asn Glu Met Glu Asn
        1475                1480                1485

Thr Gln Arg Cys Met Cys Glu Ala Leu Gln Gln Ile Met Glu Asn Gln
    1490                1495                1500

Cys Asp Arg Leu Gln Asp Arg Gln Met Val Gln Gln Phe Lys Arg Glu
1505                1510                1515                1520

Leu Met Asn Leu Pro Gln Gln Cys Asn Phe Arg Ala Pro Gln Arg Cys
                1525                1530                1535

Asp Leu Asp Val Ser Gly Gly Arg Cys
            1540                1545

<210> SEQ ID NO 13

-continued

<211> LENGTH: 614
<212> TYPE: PRT
<213> ORGANISM: Artificial Sequence
<220> FEATURE:
<223> OTHER INFORMATION: Modified Ara h1

<400> SEQUENCE: 13

```
Met Arg Gly Arg Val Ser Pro Leu Met Leu Leu Leu Gly Ile Leu Val
1               5                   10                  15

Leu Ala Ser Val Ser Ala Thr Gln Ala Lys Ser Pro Tyr Arg Lys Thr
            20                  25                  30

Glu Asn Pro Cys Ala Gln Arg Cys Leu Gln Ser Cys Gln Gln Glu Pro
        35                  40                  45

Asp Asp Leu Lys Gln Lys Ala Cys Glu Ser Arg Cys Thr Lys Leu Glu
    50                  55                  60

Tyr Asp Pro Arg Cys Val Tyr Asp Thr Gly Ala Thr Asn Gln Arg His
65                  70                  75                  80

Pro Pro Gly Glu Arg Thr Arg Gly Arg Gln Pro Gly Asp Tyr Asp Asp
                85                  90                  95

Asp Arg Arg Gln Pro Arg Arg Glu Glu Gly Gly Arg Trp Gly Pro Ala
            100                 105                 110

Glu Pro Arg Glu Arg Glu Arg Glu Glu Asp Trp Arg Gln Pro Arg Glu
        115                 120                 125

Asp Trp Arg Arg Pro Ser His Gln Gln Pro Arg Lys Ile Arg Pro Glu
    130                 135                 140

Gly Arg Glu Gly Glu Gln Glu Trp Gly Thr Pro Gly Ser Glu Val Arg
145                 150                 155                 160

Glu Glu Thr Ser Arg Asn Asn Pro Phe Tyr Phe Pro Ser Arg Arg Phe
                165                 170                 175

Ser Thr Arg Tyr Gly Asn Gln Asn Gly Arg Ile Arg Val Leu Gln Arg
            180                 185                 190

Phe Asp Gln Arg Ser Lys Gln Phe Gln Asn Leu Gln Asn His Arg Ile
        195                 200                 205

Val Gln Ile Glu Ala Arg Pro Asn Thr Leu Val Leu Pro Lys His Ala
    210                 215                 220

Asp Ala Asp Asn Ile Leu Val Ile Gln Gln Gly Gln Ala Thr Val Thr
225                 230                 235                 240

Val Ala Asn Gly Asn Asn Arg Lys Ser Phe Asn Leu Asp Glu Gly His
                245                 250                 255

Ala Leu Arg Ile Pro Ser Gly Phe Ile Ser Tyr Ile Leu Asn Arg His
            260                 265                 270

Asp Asn Gln Asn Leu Arg Val Ala Lys Ile Ser Met Pro Val Asn Thr
        275                 280                 285

Pro Gly Gln Phe Glu Asp Phe Phe Pro Ala Ser Ser Arg Asp Gln Ser
    290                 295                 300

Ser Tyr Leu Gln Gly Phe Ser Arg Asn Thr Leu Glu Ala Ala Phe Asn
305                 310                 315                 320

Ala Glu Phe Asn Glu Ile Arg Arg Val Leu Leu Glu Glu Asn Ala Gly
                325                 330                 335

Gly Glu Gln Glu Glu Arg Gly Gln Arg Arg Arg Ser Thr Arg Ser Ser
            340                 345                 350

Asp Asn Glu Gly Val Ile Val Lys Val Ser Lys Glu His Val Gln Glu
        355                 360                 365

Leu Thr Lys His Ala Lys Ser Val Ser Lys Lys Gly Ser Glu Glu Glu
    370                 375                 380
```

```
Asp Ile Thr Asn Pro Ile Asn Leu Arg Asp Gly Glu Pro Asp Leu Ser
385                 390                 395                 400

Asn Asn Phe Gly Arg Leu Phe Glu Val Lys Pro Asp Lys Lys Asn Pro
                405                 410                 415

Gln Leu Gln Asp Leu Asp Met Met Leu Thr Cys Val Glu Ile Lys Glu
            420                 425                 430

Gly Ala Leu Met Leu Pro His Phe Asn Ser Lys Ala Met Val Ile Val
        435                 440                 445

Val Val Asn Lys Gly Thr Gly Asn Leu Glu Leu Val Ala Val Arg Lys
    450                 455                 460

Glu Gln Gln Gln Arg Gly Arg Arg Glu Gln Trp Glu Glu Glu Glu Glu
465                 470                 475                 480

Glu Asp Glu Glu Glu Glu Gly Ser Asn Arg Glu Val Arg Arg Tyr Thr
                485                 490                 495

Ala Arg Leu Lys Glu Gly Asp Val Phe Ile Met Pro Ala Ala His Pro
            500                 505                 510

Val Ala Ile Asn Ala Ser Ser Glu Leu His Leu Leu Gly Phe Gly Ile
        515                 520                 525

Asn Ala Glu Asn Asn His Arg Ile Phe Leu Ala Gly Asp Lys Asp Asn
    530                 535                 540

Val Ile Asp Gln Ile Glu Lys Gln Ala Lys Asp Leu Ala Phe Pro Gly
545                 550                 555                 560

Ser Gly Glu Gln Val Glu Lys Leu Ile Lys Asn Gln Arg Glu Ser His
                565                 570                 575

Phe Val Ser Ala Arg Pro Gln Ser Gln Ser Pro Ser Ser Pro Glu Lys
            580                 585                 590

Glu Asp Gln Glu Glu Glu Asn Gln Gly Gly Lys Gly Pro Leu Leu Ser
        595                 600                 605

Ile Leu Lys Ala Phe Asn
    610

<210> SEQ ID NO 14
<211> LENGTH: 507
<212> TYPE: PRT
<213> ORGANISM: Artificial Sequence
<220> FEATURE:
<223> OTHER INFORMATION: Modified Ara h3

<400> SEQUENCE: 14

Arg Gln Gln Pro Glu Glu Asn Ala Cys Gln Phe Gln Arg Leu Asn Ala
1               5                   10                  15

Gln Arg Pro Asp Asn Arg Ile Glu Ser Glu Gly Gly Tyr Ile Glu Thr
            20                  25                  30

Trp Asn Pro Asn Asn Gln Glu Phe Glu Cys Ala Gly Val Ala Leu Ser
        35                  40                  45

Arg Leu Val Leu Arg Arg Asn Ala Leu Arg Arg Pro Phe Tyr Ser Asn
    50                  55                  60

Ala Pro Gln Glu Ile Phe Ile Gln Gln Gly Arg Gly Tyr Phe Gly Leu
65                  70                  75                  80

Ile Phe Pro Gly Cys Pro Arg His Tyr Glu Glu Pro His Thr Gln Gly
                85                  90                  95

Arg Arg Ser Gln Ser Gln Arg Pro Pro Arg Arg Leu Gln Gly Glu Asp
            100                 105                 110

Gln Ser Gln Gln Gln Arg Asp Ser His Gln Lys Val His Arg Phe Asp
        115                 120                 125
```

Glu Gly Asp Leu Ile Ala Val Pro Thr Gly Val Ala Phe Trp Leu Tyr
130                 135                 140

Asn Asp His Asp Thr Asp Val Val Ala Val Ser Leu Thr Asp Thr Asn
145                 150                 155                 160

Asn Asn Asp Asn Gln Leu Asp Gln Phe Pro Arg Arg Phe Asn Leu Ala
            165                 170                 175

Gly Asn Thr Glu Gln Glu Phe Leu Arg Tyr Gln Gln Gln Ser Arg Gln
            180                 185                 190

Ser Arg Arg Arg Ser Leu Pro Tyr Ser Pro Tyr Ser Pro Gln Ser Gln
        195                 200                 205

Pro Arg Gln Glu Glu Arg Glu Phe Ser Pro Arg Gly His Ser Arg
210                 215                 220

Arg Glu Arg Ala Gly Gln Glu Glu Asn Glu Gly Gly Asn Ile Phe
225                 230                 235                 240

Ser Gly Phe Thr Pro Glu Phe Leu Glu Gln Ala Phe Gln Val Asp Asp
            245                 250                 255

Arg Gln Ile Val Gln Asn Leu Arg Gly Glu Thr Glu Ser Glu Glu Glu
            260                 265                 270

Gly Ala Ile Val Thr Val Arg Gly Gly Leu Arg Ile Leu Ser Pro Asp
            275                 280                 285

Arg Lys Arg Arg Ala Asp Glu Glu Glu Tyr Asp Glu Asp Glu Tyr
290                 295                 300

Glu Tyr Asp Glu Glu Asp Arg Arg Arg Gly Arg Gly Ser Arg Gly Arg
305                 310                 315                 320

Gly Asn Gly Ile Glu Glu Thr Ile Cys Thr Ala Ser Ala Lys Lys Asn
            325                 330                 335

Ile Gly Arg Asn Arg Ser Pro Asp Ile Tyr Asn Pro Gln Ala Gly Ser
            340                 345                 350

Leu Lys Thr Ala Asn Asp Leu Asn Leu Ile Leu Arg Trp Leu Gly
        355                 360                 365

Pro Ser Ala Glu Tyr Gly Asn Leu Tyr Arg Asn Ala Leu Phe Val Ala
            370                 375                 380

His Tyr Asn Thr Asn Ala His Ser Ile Ile Tyr Arg Leu Arg Gly Arg
385                 390                 395                 400

Ala His Val Gln Val Asp Ser Asn Gly Asn Arg Val Tyr Asp Glu
            405                 410                 415

Glu Leu Gln Glu Gly His Val Leu Val Val Pro Gln Asn Phe Ala Val
            420                 425                 430

Ala Gly Lys Ser Gln Ser Glu Asn Phe Glu Tyr Val Ala Phe Lys Thr
            435                 440                 445

Asp Ser Arg Pro Ser Ile Ala Asn Leu Ala Gly Glu Asn Ser Val Ile
450                 455                 460

Asp Asn Leu Pro Glu Glu Val Val Ala Asn Ser Tyr Gly Leu Gln Arg
465                 470                 475                 480

Glu Gln Ala Arg Gln Leu Lys Asn Asn Asn Pro Phe Lys Phe Phe Val
            485                 490                 495

Pro Pro Ser Gln Gln Ser Pro Arg Ala Val Ala
            500                 505

<210> SEQ ID NO 15
<211> LENGTH: 530
<212> TYPE: PRT
<213> ORGANISM: Artificial Sequence
<220> FEATURE:

<223> OTHER INFORMATION: Modified Ara h3

<400> SEQUENCE: 15

```
Met Ala Lys Leu Leu Glu Leu Ser Phe Cys Phe Cys Phe Leu Val Leu
1               5                   10                  15

Gly Ala Ser Ser Ile Ser Phe Arg Gln Gln Pro Glu Glu Asn Ala Cys
            20                  25                  30

Gln Phe Gln Arg Leu Asn Ala Gln Arg Pro Asp Asn Arg Ile Glu Ser
        35                  40                  45

Glu Gly Gly Tyr Ile Glu Thr Trp Asn Pro Asn Asn Gln Glu Phe Glu
    50                  55                  60

Cys Ala Gly Val Ala Leu Ser Arg Leu Val Leu Arg Arg Asn Ala Leu
65                  70                  75                  80

Arg Arg Pro Phe Tyr Ser Asn Ala Pro Gln Glu Ile Phe Ile Gln Gln
                85                  90                  95

Gly Arg Gly Tyr Phe Gly Leu Ile Phe Pro Gly Cys Pro Ser Thr Tyr
            100                 105                 110

Glu Glu Pro Ala Gln Gln Gly Arg Arg Tyr Gln Ser Gln Arg Pro Pro
        115                 120                 125

Arg Arg Leu Gln Glu Glu Asp Gln Ser Gln Gln Gln Asp Ser His
    130                 135                 140

Gln Lys Val His Arg Phe Asn Glu Gly Asp Leu Ile Ala Val Pro Thr
145                 150                 155                 160

Gly Val Ala Phe Trp Leu Tyr Asn Asp His Asp Thr Asp Val Val Ala
                165                 170                 175

Val Ser Leu Thr Asp Thr Asn Asn Asn Asp Asn Gln Leu Asp Gln Phe
            180                 185                 190

Pro Arg Arg Phe Asn Leu Ala Gly Asn His Glu Gln Glu Phe Leu Arg
        195                 200                 205

Tyr Gln Gln Gln Ser Arg Gln Ser Arg Arg Ser Leu Pro Tyr Ser
    210                 215                 220

Pro Tyr Ser Pro Gln Ser Gln Pro Arg Gln Glu Glu Arg Glu Phe Ser
225                 230                 235                 240

Pro Arg Gly Gln His Ser Arg Arg Glu Arg Ala Gly Gln Glu Glu Glu
                245                 250                 255

Asn Glu Gly Gly Asn Ile Phe Ser Gly Phe Thr Pro Glu Phe Leu Ala
            260                 265                 270

Gln Ala Phe Gln Val Asp Asp Arg Gln Ile Val Gln Asn Leu Arg Gly
        275                 280                 285

Glu Asn Glu Ser Glu Glu Gln Gly Ala Ile Val Thr Val Arg Gly Gly
    290                 295                 300

Leu Arg Ile Leu Ser Pro Asp Arg Lys Arg Gly Ala Asp Glu Glu Glu
305                 310                 315                 320

Glu Tyr Asp Glu Asp Glu Tyr Tyr Asp Glu Glu Asp Arg Arg Arg
                325                 330                 335

Gly Arg Gly Ser Arg Gly Ser Gly Asn Gly Ile Glu Glu Thr Ile Cys
            340                 345                 350

Thr Ala Thr Val Lys Lys Asn Ile Gly Arg Asn Arg Ser Pro Asp Ile
        355                 360                 365

Tyr Asn Pro Gln Ala Gly Ser Leu Lys Thr Ala Asn Glu Leu Asn Leu
    370                 375                 380

Leu Ile Leu Arg Trp Leu Gly Leu Ser Ala Glu Tyr Gly Asn Leu Tyr
385                 390                 395                 400
```

```
Arg Asn Ala Leu Phe Val Pro His Tyr Asn Thr Asn Ala His Ser Ile
                405                 410                 415

Ile Tyr Ala Leu Arg Gly Arg Ala His Val Gln Val Val Asp Ser Asn
            420                 425                 430

Gly Asn Arg Val Tyr Asp Glu Glu Leu Gln Glu Gly His Val Leu Val
        435                 440                 445

Val Pro Gln Asn Phe Ala Val Ala Gly Lys Ser Gln Ser Asp Asn Phe
    450                 455                 460

Glu Tyr Val Ala Phe Lys Thr Asp Ser Arg Pro Ser Ile Ala Asn Leu
465                 470                 475                 480

Ala Gly Glu Asn Ser Val Ile Asp Asn Leu Pro Glu Glu Val Val Ala
                485                 490                 495

Asn Ser Tyr Gly Leu Pro Arg Glu Gln Ala Arg Gln Leu Lys Asn Asn
            500                 505                 510

Asn Pro Phe Lys Phe Val Pro Pro Ser Gln Gln Ser Pro Arg Ala
        515                 520                 525

Val Ala
    530

<210> SEQ ID NO 16
<211> LENGTH: 129
<212> TYPE: PRT
<213> ORGANISM: Artificial Sequence
<220> FEATURE:
<223> OTHER INFORMATION: Modified Ara h6

<400> SEQUENCE: 16

Ala His Ala Ser Ala Met Arg Arg Glu Arg Gly Arg Gln Gly Asp Ser
1               5                   10                  15

Ser Ser Cys Glu Arg Gln Val Asp Gly Val Asn Leu Lys Pro Cys Glu
            20                  25                  30

Gln His Ile Met Gln Arg Ile Met Gly Glu Gln Glu Gln Tyr Asp Ser
        35                  40                  45

Tyr Asn Phe Gly Ser Thr Arg Ser Ser Asp Gln Gln Gln Arg Cys Cys
    50                  55                  60

Asp Glu Leu Asn Glu Met Glu Asn Thr Gln Arg Cys Met Cys Glu Ala
65                  70                  75                  80

Leu Gln Gln Ile Met Glu Asn Gln Cys Asp Gly Leu Gln Asp Arg Gln
                85                  90                  95

Met Val Gln His Phe Lys Arg Glu Leu Met Asn Leu Pro Gln Gln Cys
            100                 105                 110

Asn Phe Gly Ala Pro Gln Arg Cys Asp Leu Asp Val Ser Gly Gly Arg
        115                 120                 125

Cys

<210> SEQ ID NO 17
<211> LENGTH: 530
<212> TYPE: PRT
<213> ORGANISM: Artificial Sequence
<220> FEATURE:
<223> OTHER INFORMATION: Modified Ara h4

<400> SEQUENCE: 17

Met Ala Lys Leu Leu Glu Leu Ser Phe Cys Phe Cys Phe Leu Val Leu
1               5                   10                  15

Gly Ala Ser Ser Ile Ser Phe Arg Gln Gln Pro Glu Glu Asn Ala Cys
            20                  25                  30
```

```
Gln Phe Gln Arg Leu Asn Ala Gln Arg Pro Asp Asn Arg Ile Glu Ser
         35                  40                  45
Glu Gly Gly Tyr Ile Glu Thr Trp Asn Pro Asn Gln Glu Phe Glu
 50                  55                  60
Cys Ala Gly Val Ala Leu Ser Arg Leu Val Leu Arg Arg Asn Ala Leu
 65                  70                  75                  80
Arg Arg Pro Phe Tyr Ser Asn Ala Pro Gln Glu Ile Phe Ile Gln Gln
                 85                  90                  95
Gly Arg Gly Tyr Phe Gly Leu Ile Phe Pro Gly Cys Pro Ser Thr Tyr
                100                 105                 110
Glu Glu Pro Ala Gln Gln Gly Arg Arg Tyr Gln Ser Gln Arg Pro Pro
            115                 120                 125
Arg Arg Leu Gln Glu Glu Asp Gln Ser Gln Gln Gln Gln Asp Ser His
    130                 135                 140
Gln Lys Val His Arg Phe Asn Glu Gly Asp Leu Ile Ala Val Pro Thr
145                 150                 155                 160
Gly Val Ala Phe Trp Leu Tyr Asn Asp His Asp Thr Asp Val Val Ala
                165                 170                 175
Val Ser Leu Thr Asp Thr Asn Asn Asn Asp Asn Gln Leu Asp Gln Phe
                180                 185                 190
Pro Arg Arg Phe Asn Leu Ala Gly Asn His Glu Gln Glu Phe Leu Arg
            195                 200                 205
Tyr Gln Gln Gln Ser Arg Gln Ser Arg Arg Arg Ser Leu Pro Tyr Ser
    210                 215                 220
Pro Tyr Ser Pro His Ser Arg Pro Arg Glu Glu Arg Glu Phe Arg
225                 230                 235                 240
Pro Arg Gly Gln His Ser Arg Arg Glu Arg Ala Gly Gln Glu Glu Glu
                245                 250                 255
Asp Glu Gly Gly Asn Ile Phe Ser Gly Phe Thr Pro Glu Phe Leu Glu
            260                 265                 270
Gln Ala Phe Gln Val Asp Asp Arg Gln Ile Val Gln Asn Leu Trp Gly
    275                 280                 285
Glu Asn Glu Ser Glu Glu Glu Gly Ala Ile Val Thr Val Arg Gly Gly
290                 295                 300
Leu Arg Ile Leu Ser Pro Asp Gly Thr Arg Gly Ala Asp Glu Glu Glu
305                 310                 315                 320
Glu Tyr Asp Glu Asp Gln Tyr Glu Tyr His Glu Gln Asp Gly Arg Arg
                325                 330                 335
Gly Arg Gly Ser Arg Gly Gly Asn Gly Ile Glu Glu Thr Ile Cys
            340                 345                 350
Thr Ala Cys Val Lys Lys Asn Ile Gly Gly Asn Arg Ser Pro His Ile
    355                 360                 365
Tyr Asp Pro Gln Arg Trp Phe Thr Gln Asn Cys His Asp Leu Asn Leu
370                 375                 380
Leu Ile Leu Arg Trp Leu Gly Leu Ser Ala Glu Tyr Gly Asn Leu Tyr
385                 390                 395                 400
Arg Asn Ala Leu Phe Val Pro His Tyr Asn Thr Asn Ala His Ser Ile
                405                 410                 415
Ile Tyr Ala Leu Arg Gly Arg Ala His Val Gln Val Val Asp Ser Asn
            420                 425                 430
Gly Asn Arg Val Tyr Asp Glu Glu Leu Gln Glu Gly His Val Leu Val
    435                 440                 445
Val Pro Gln Asn Phe Ala Val Ala Gly Lys Ser Gln Ser Glu Asn Phe
```

```
    450                 455                 460

Glu Tyr Val Ala Phe Lys Thr Asp Ser Arg Pro Ser Ile Ala Asn Phe
465                 470                 475                 480

Ala Gly Glu Asn Ser Phe Ile Asp Asn Leu Pro Glu Glu Val Val Ala
                485                 490                 495

Asn Ser Tyr Gly Leu Pro Arg Glu Gln Ala Arg Gln Leu Lys Asn Asn
            500                 505                 510

Asn Pro Phe Lys Phe Phe Val Pro Pro Phe Gln Gln Ser Pro Arg Ala
        515                 520                 525

Val Ala
    530

<210> SEQ ID NO 18
<211> LENGTH: 131
<212> TYPE: PRT
<213> ORGANISM: Artificial Sequence
<220> FEATURE:
<223> OTHER INFORMATION: Modified Ara h5

<400> SEQUENCE: 18

Met Ser Trp Gln Thr Tyr Val Asp Asn His Leu Leu Cys Glu Ile Glu
1               5                   10                  15

Gly Asp His Leu Ser Ser Ala Ala Ile Leu Gly Gln Asp Gly Gly Val
            20                  25                  30

Trp Ala Gln Ser Ser His Phe Pro Gln Phe Lys Pro Glu Glu Ile Thr
        35                  40                  45

Ala Ile Met Asn Asp Phe Ala Glu Pro Gly Ser Leu Ala Pro Thr Gly
    50                  55                  60

Leu Tyr Leu Gly Gly Thr Lys Tyr Met Val Ile Gln Gly Glu Pro Gly
65                  70                  75                  80

Ala Ile Ile Pro Gly Lys Lys Gly Pro Gly Gly Val Thr Ile Glu Lys
                85                  90                  95

Thr Asn Gln Ala Leu Ile Ile Gly Ile Tyr Asp Lys Pro Met Thr Pro
            100                 105                 110

Gly Gln Cys Asn Met Ile Val Glu Arg Leu Gly Asp Tyr Leu Ile Asp
        115                 120                 125

Thr Gly Leu
    130

<210> SEQ ID NO 19
<211> LENGTH: 160
<212> TYPE: PRT
<213> ORGANISM: Artificial Sequence
<220> FEATURE:
<223> OTHER INFORMATION: Modified Ara h7

<400> SEQUENCE: 19

Met Met Val Lys Leu Ser Ile Leu Val Ala Leu Leu Gly Ala Leu Leu
1               5                   10                  15

Val Val Ala Ser Ala Thr Arg Trp Asp Pro Asp Arg Gly Ser Arg Gly
            20                  25                  30

Ser Arg Trp Asp Ala Pro Ser Arg Gly Asp Asp Gln Cys Gln Arg Gln
        35                  40                  45

Leu Gln Arg Ala Asn Leu Arg Pro Cys Glu Glu His Met Arg Arg Arg
    50                  55                  60

Val Glu Gln Glu Gln Glu Gln Glu Gln Asp Glu Tyr Pro Tyr Ser Arg
65                  70                  75                  80
```

```
Arg Gly Ser Arg Gly Arg Gln Pro Gly Glu Ser Asp Glu Asn Gln Glu
                85                  90                  95

Gln Arg Cys Cys Asn Glu Leu Asn Arg Phe Gln Asn Asn Gln Arg Cys
            100                 105                 110

Met Cys Gln Ala Leu Gln Gln Ile Leu Gln Asn Gln Ser Phe Trp Val
        115                 120                 125

Pro Ala Gly Gln Glu Pro Val Ala Ser Asp Gly Gly Ala Gln Glu
    130                 135                 140

Leu Ala Pro Glu Leu Arg Val Gln Val Thr Lys Pro Leu Arg Pro Leu
145                 150                 155                 160

<210> SEQ ID NO 20
<211> LENGTH: 137
<212> TYPE: PRT
<213> ORGANISM: Artificial Sequence
<220> FEATURE:
<223> OTHER INFORMATION: Modified Ara h11

<400> SEQUENCE: 20

Met Ala Glu Ala Leu Tyr Tyr Gly Gly Arg Gln Arg Gln Glu Gln Pro
1               5                   10                  15

Arg Ser Thr Gln Leu Val Lys Ala Thr Thr Ala Val Val Ala Gly Gly
            20                  25                  30

Ser Leu Leu Ile Leu Ala Gly Leu Val Leu Ala Gly Thr Val Ile Gly
        35                  40                  45

Leu Thr Thr Ile Thr Pro Leu Phe Val Ile Phe Ser Pro Val Leu Val
    50                  55                  60

Pro Ala Val Ile Thr Val Ala Leu Leu Gly Leu Gly Phe Leu Ala Ser
65                  70                  75                  80

Gly Gly Phe Gly Val Ala Ala Ile Thr Val Leu Thr Trp Ile Tyr Arg
                85                  90                  95

Tyr Val Thr Gly Lys His Pro Pro Gly Ala Asn Gln Leu Asp Thr Ala
            100                 105                 110

Arg His Lys Leu Met Gly Lys Ala Arg Glu Ile Lys Asp Phe Gly Gln
        115                 120                 125

Gln Gln Thr Ser Gly Ala Gln Ala Ser
    130                 135

<210> SEQ ID NO 21
<211> LENGTH: 157
<212> TYPE: PRT
<213> ORGANISM: Artificial Sequence
<220> FEATURE:
<223> OTHER INFORMATION: Modified Ara h8

<400> SEQUENCE: 21

Met Gly Val Phe Thr Phe Glu Asp Glu Ile Thr Ser Thr Val Pro Pro
1               5                   10                  15

Ala Lys Leu Tyr Asn Ala Met Lys Asp Ala Asp Ser Ile Thr Pro Lys
            20                  25                  30

Ile Ile Asp Asp Val Lys Ser Val Glu Ile Val Glu Gly Asn Gly Gly
        35                  40                  45

Pro Gly Thr Ile Lys Lys Leu Thr Ile Val Glu Asp Gly Glu Thr Lys
    50                  55                  60

Phe Ile Leu His Lys Val Glu Ser Ile Asp Glu Ala Asn Tyr Ala Tyr
65                  70                  75                  80

Asn Tyr Ser Val Val Gly Gly Val Ala Leu Pro Pro Thr Ala Glu Lys
                85                  90                  95
```

```
Ile Thr Phe Glu Thr Lys Leu Val Glu Gly Pro Asn Gly Gly Ser Ile
                100                 105                 110

Gly Lys Leu Thr Leu Lys Tyr His Thr Lys Gly Asp Ala Lys Pro Asp
            115                 120                 125

Glu Glu Glu Leu Lys Lys Gly Lys Ala Lys Gly Glu Gly Leu Phe Arg
130                 135                 140

Ala Ile Glu Gly Tyr Val Leu Ala Asn Pro Thr Gln Tyr
145                 150                 155

<210> SEQ ID NO 22
<211> LENGTH: 153
<212> TYPE: PRT
<213> ORGANISM: Artificial Sequence
<220> FEATURE:
<223> OTHER INFORMATION: Modified Ara h8

<400> SEQUENCE: 22

Met Gly Val His Thr Phe Glu Glu Ser Thr Ser Pro Val Pro Pro
1               5                   10                  15

Ala Lys Leu Phe Lys Ala Thr Val Val Asp Gly Asp Glu Leu Thr Pro
            20                  25                  30

Lys Leu Ile Pro Ala Ile Gln Ser Ile Glu Ile Val Glu Gly Asn Gly
        35                  40                  45

Gly Pro Gly Thr Val Lys Lys Val Thr Ala Val Glu Asp Gly Lys Thr
    50                  55                  60

Ser Tyr Val Leu His Lys Ile Asp Ala Ile Asp Glu Ala Thr Tyr Thr
65                  70                  75                  80

Tyr Asp Tyr Thr Ile Ser Gly Thr Gly Phe Gln Glu Ile Leu Glu
                85                  90                  95

Lys Val Ser Phe Lys Thr Lys Leu Glu Ala Ala Asp Gly Gly Ser Lys
            100                 105                 110

Ile Lys Val Ser Val Thr Phe His Thr Lys Gly Asp Ala Pro Leu Pro
        115                 120                 125

Asp Glu Val His Gln Asp Val Lys Gln Lys Ser Gln Gly Ile Phe Lys
    130                 135                 140

Ala Ile Glu Gly Tyr Val Leu Ser Asn
145                 150

<210> SEQ ID NO 23
<211> LENGTH: 116
<212> TYPE: PRT
<213> ORGANISM: Artificial Sequence
<220> FEATURE:
<223> OTHER INFORMATION: Modified Ara h9

<400> SEQUENCE: 23

Met Ala Ser Leu Lys Phe Ala Phe Val Met Leu Val Cys Met Ala Met
1               5                   10                  15

Val Gly Ala Pro Met Val Asn Ala Ile Ser Cys Gly Gln Val Asn Ser
            20                  25                  30

Ala Leu Ala Pro Cys Ile Pro Phe Leu Thr Lys Gly Gly Ala Pro Pro
        35                  40                  45

Pro Ala Cys Cys Ser Gly Val Arg Gly Leu Leu Gly Ala Leu Arg Thr
    50                  55                  60

Thr Ala Asp Arg Gln Ala Ala Cys Asn Cys Leu Lys Ala Ala Ala Gly
65                  70                  75                  80

Ser Leu Arg Gly Leu Asn Gln Gly Asn Ala Ala Ala Leu Pro Gly Arg
```

```
                    85                  90                  95
Cys Gly Val Ser Ile Pro Tyr Lys Ile Ser Thr Ser Thr Asn Cys Ala
                100                 105                 110
Thr Ile Lys Phe
            115
```

<210> SEQ ID NO 24
<211> LENGTH: 92
<212> TYPE: PRT
<213> ORGANISM: Artificial Sequence
<220> FEATURE:
<223> OTHER INFORMATION: Modified Ara h9

<400> SEQUENCE: 24

```
Leu Ser Cys Gly Gln Val Asn Ser Ala Leu Ala Pro Cys Ile Thr Phe
1               5                   10                  15
Leu Thr Lys Gly Gly Val Pro Ser Gly Pro Cys Cys Ser Gly Val Arg
                20                  25                  30
Gly Leu Leu Gly Ala Ala Lys Thr Thr Ala Asp Arg Gln Ala Ala Cys
            35                  40                  45
Asn Cys Leu Lys Ala Ala Ala Gly Ser Leu His Gly Leu Asn Gln Gly
        50                  55                  60
Asn Ala Ala Leu Pro Gly Arg Cys Gly Val Ser Ile Pro Tyr Lys
65                  70                  75                  80
Ile Ser Thr Ser Thr Asn Cys Ala Thr Ile Lys Phe
                85                  90
```

<210> SEQ ID NO 25
<211> LENGTH: 169
<212> TYPE: PRT
<213> ORGANISM: Artificial Sequence
<220> FEATURE:
<223> OTHER INFORMATION: Modified Ara h10

<400> SEQUENCE: 25

```
Met Thr Asp Arg Thr Gln Pro His Thr Val Gln Val His Thr Thr Ala
1               5                   10                  15
Gly Arg Phe Gly Asp Thr Ala Ala Gly Thr Asn Arg Tyr Pro Asp Arg
                20                  25                  30
Gly Pro Ser Thr Ser Lys Val Ile Ala Val Ile Thr Gly Leu Pro Ile
            35                  40                  45
Gly Gly Thr Leu Leu Leu Phe Ala Gly Leu Ala Leu Ala Gly Thr Leu
        50                  55                  60
Leu Gly Leu Ala Val Thr Thr Pro Leu Phe Ile Leu Phe Ser Pro Val
65                  70                  75                  80
Ile Val Pro Ala Ile Ile Val Val Gly Leu Ser Val Ala Gly Phe Leu
                85                  90                  95
Thr Ser Gly Ala Cys Gly Leu Thr Gly Leu Ser Ser Phe Ser Trp Val
                100                 105                 110
Met Asn Tyr Ile Arg Gln Thr His Gly Ser Val Pro Glu Gln Leu Glu
            115                 120                 125
Met Ala Lys His Arg Met Ala Asp Val Ala Gly Tyr Val Gly Gln Lys
        130                 135                 140
Thr Lys Asp Val Gly Gln Lys Thr Lys Glu Val Gly Gln Glu Ile Gln
145                 150                 155                 160
Thr Lys Ala Gln Asp Ser Lys Arg Asn
                165
```

```
<210> SEQ ID NO 26
<211> LENGTH: 150
<212> TYPE: PRT
<213> ORGANISM: Artificial Sequence
<220> FEATURE:
<223> OTHER INFORMATION: Modified Ara h10

<400> SEQUENCE: 26

Met Thr Asp Arg Thr Gln Pro His Ala Val Gln Val His Thr Thr Ala
1               5                   10                  15

Gly Arg Phe Gly Asp Thr Ala Ala Gly Thr Asn Arg Tyr Ala Asp Arg
            20                  25                  30

Gly Pro Ser Thr Ser Lys Val Ile Ala Val Ile Th

-continued

```
<210> SEQ ID NO 28
<211> LENGTH: 169
<212> TYPE: PRT
<213> ORGANISM: Artificial Sequence
<220> FEATURE:
<223> OTHER INFORMATION: Modified Ara h10

<400> SEQUENCE: 28

Met Thr Asp Arg Thr Gln Pro His Thr Val Gln Val His Thr Thr Ala
1               5                   10                  15

Gly Arg Phe Gly Asp Thr Ala Ala Gly Thr Asn Arg Tyr Pro Asp Arg
            20                  25                  30

Gly Pro Ser Thr Ser Lys Val Ile Ala Val Ile Thr Gly Leu Pro Ile
        35                  40                  45

Gly Gly Thr Leu Leu Leu Phe Ala Gly Leu Ala Leu Ala Gly Thr Leu
    50                  55                  60

Leu Gly Leu Ala Val Thr Thr Pro Leu Phe Ile Leu Phe Ser Pro Val
65                  70                  75                  80

Ile Val Pro Ala Ile Ile Val Val Gly Leu Ser Val Ala Gly Phe Leu
                85                  90                  95

Thr Ser Gly Ala Cys Gly Leu Thr Gly Leu Ser Ser Phe Ser Trp Val
            100                 105                 110

Met Asn Tyr Ile Arg Gln Thr His Gly Ser Val Pro Glu Gln Leu Glu
        115                 120                 125

Met Ala Lys His Arg Met Ala Asp Val Ala Gly Tyr Val Gly Gln Lys
    130                 135                 140

Thr Lys Asp Val Gly Gln Lys Thr Lys Glu Val Gly Gln Glu Ile Gln
145                 150                 155                 160

Thr Lys Ala Gln Asp Ser Lys Arg Thr
                165
```

IMMUNE MODULATION

RELATED APPLICATIONS

This application is the National Stage of International Application. No. PCT/AU2014/000286, filed 17 Mar. 2014, which claims benefit of priority to U.S. Provisional Patent Application Ser. No. 61/852,239, filed 15 Mar. 2013, the specification of which is incorporated by reference herein.

INCORPORATION BY REFERENCE OF SEQUENCE LISTING PROVIDED ELECTRONICALLY

An electronic version of the Sequence Listing is filed herewith, the contents of which are incorporated by reference in their entirety. The electronic file was created on Sep. 15, 2015, is 38 kilobytes in size, and titled 755USSEQUS1.txt. A substitute Sequence Listing has been filed electronically, on Dec. 26, 2018, the contents of which are incorporated by reference in their entirety. The electronic file was created on Dec. 26, 2018, is 69 kilobytes in size, and is titled 755USSEQUS2.txt. A second substitute Sequence Listing has been filed electronically, on Nov. 7, 2019, the contents of which are incorporated by reference in their entirety. The electronic file was created on Nov. 5, 2019, is 69 kilobytes in size, and is titled 755SEQUS3.txt. A third substitute Sequence Listing has been filed electronically, on Jun. 29, 2020, the contents of which are incorporated by reference in their entirety. The electronic file was created on Jun. 28, 2020, is 71 kilobytes in size, and is titled 755SEQUS4.txt.

TECHNICAL FIELD

The present specification relates generally to the field of prophylactic or therapeutic vaccines. In particular, the specification relates to a vaccine for the treatment of peanut allergies by suppressing the allergic response thereto.

BACKGROUND

In principle, allergic diseases are disorders of the immune system associated with a dysregulation of the $T_H1$ and $T_H2$ lymphocyte subsets [de Vries et al. 1999, Parronchi et al. 1999, Singh et al. 1999]. It has been postulated that with a declining incidence of infectious diseases due to vaccination, the use of antibiotics and other public health practices, a major source of $T_H1$ immune provocation has been lost, with a consequent increase in the $T_H2$ bias of immune responses towards environmental allergens [Holgate 1999, Shaheen et al. 1996].

Of the various allergic diseases that affect the general population, peanut-induced anaphylaxis is particularly severe and represents the most common contributor of emergency department admissions for treatment of anaphylactic reactions.

Allergies to peanut result from an aberrant immune response directed against an otherwise harmless environmental antigen. Peanut allergy and anaphylaxis are centred around a type 2 immune response, characterised by the generation of $T_H2$ T cells and IgE antibody secreting B cells. By contrast, a types 1 immune response can be characterised by antibodies predominately of IgG (IgG2a isotype in mice), activation of NK cells and phagocytic cells, and the development of cytotoxic T lymphocytes (CTL). Both type 1 and 2 responses are coordinated by helper T cells, which differentiate into several functionally different subsets including $T_H1$ and $T_H2$ lymphocytes. Theses subsets are characterised by their cytokine secretion profile [Mosmann et al. 1989], where $T_H1$ cells produce IFN-gamma and $T_H2$ cells typically secrete IL-4, IL-5 and IL-13.

Orally ingested peanut allergens first encounter the gut mucosal immune system. Microfold (M) cells are specialised follicle-associated cells that line the epithelium of the gastrointestinal tract and lie in close proximity to Peyer's patches. They are responsible for the induction of tolerising and/or protective gut-associated immune responses. Sensitization to food allergens occurs when exogenous food antigens are taken up by M cells, and then presented to macrophages and dendritic cells (DCs) [DeLong et al. 2011]. Once internalised by macrophages and DCs, the antigens are endocytosed, then denatured and degraded into peptides of around 12-20 amino acids in length. A small fraction of these small peptide fragments are then transported intracellularly and presented on the cell-surface MHC class II molecules for specific interaction with $CD4^+$ T cells. These activated $CD4^+$ T cells subsequently expand in number and release $T_H2$ cytokines. The $T_H2$ cells, IL-4 and IL-5 promote the differentiation of B cells, which bear allergens bound to surface immunoglobulin (Ig) receptors, into cells that secrete allergen-specific IgE antibodies [Turcanu et al. 2010]. These IgE-producing B cells then expand in number and become plasma cells that continuously secrete allergen-specific IgE antibodies. Environmental exposure to peanuts results in binding of peanut allergens to specific IgE-coating on mast cells and basophils. Subsequently, Fc receptor cross-linking provides a potent activation stimulus that results in the degranulation of basophils and mast cells, which rapidly release a variety of preformed proinflammatory and vasoactive compounds such as prostaglandins, leukotrienes, serine proteases, histamine and cytokines into the extracellular fluid to produce an inflammatory response [Sicherer et al. 2010], all of which culminate in the clinical manifestation of an acute allergic reaction [Long 2002].

Local symptoms of peanut allergy include abdominal pain, vomiting, cramping and diarrhea, and are common even in cases of mild peanut allergy. This acute non-life threatening reaction causes a transient increase in intestinal permeability, which subsequently allows systemic distribution of macromolecules, such as whole peanut allergens, exacerbating the allergic response to subsequent exposure to peanut allergens, which can cause life-threatening anaphylactic reactions [Sanderson et al. 1993].

Unlike traditional immunotherapy for allergic reactions to grass pollens, dust mite and bee sting venom, subcutaneous desensitization injections of peanut extracts have unacceptable risk-benefits [Oppenheimer et al. 1992]. Therefore, at present, avoiding peanuts is the only available method for prevent further reactions. However, strict avoidance is often an unrealistic strategy for many individuals, particularly in light of accidental exposure to peanuts that often occurs through ingestion of processed foods or foods prepared in the same vicinity of those containing peanuts, e.g., restaurants, schools, food courts and work canteens. Therefore, there remains a need for an effective therapeutic strategy for the treatment and prevention of the peanut allergy.

SUMMARY OF THE INVENTION

In an aspect of the present invention, there is provided a poxvirus vector comprising a nucleic acid sequence encoding a fusion protein comprising (i) at least two peanut allergens selected from list consisting of ara h 1, ara h 2, ara h 3, ara h 4, ara h 5, ara h 6 and ara h 7 and a derivative or part thereof having at least 70% sequence identity thereto, and (ii) a proteasome degradation tag to enhance intracellular degradation of the fusion protein.

In an aspect of the present invention, there is provided a poxvirus vector comprising a nucleic acid sequence encoding a fusion protein comprising (i) at least two peanut allergens selected from list consisting of ara h 1, ara h 2, ara h 3, ara h 4, ara h 5, ara h 6, ara h 7, ara h 8, ara h 9, ara h10 and ara h 11 and a derivative or part thereof having at least 70% sequence identity thereto, and (ii) a proteasome degradation tag to enhance intracellular degradation of the fusion protein.

In another aspect of the present invention, there is provided a poxvirus vector comprising a nucleic acid sequence encoding a fusion protein comprising: (i) at least three peanut allergens selected from list consisting of ara h 1, ara h 2, ara h 3, ara h 4, ara h 5, ara h 6 and ara h 7 and a derivative or part thereof having at least 70% sequence identity thereto, and (ii) a proteasome degradation tag to enhance intracellular degradation of the fusion protein.

In another aspect of the present invention, there is provided a poxvirus vector comprising a nucleic acid sequence encoding a fusion protein comprising: (i) at least three peanut allergens selected from list consisting of ara h 1, ara h 2, ara h 3, ara h 4, ara h 5, ara h 6, ara h 7, ara h 8, ara h 9, ara h10 and ara h 11 and a derivative or part thereof having at least 70% sequence identity thereto, and (ii) a proteasome degradation tag to enhance intracellular degradation of the fusion protein.

In another aspect of the present invention, there is provided use of a poxvirus vector disclosed herein in, or in the manufacture of a medicament for, the treatment of peanut allergy.

In another aspect of the present invention, there is provided a method of inducing tolerance to or suppressing an allergic response in a subject or patient, the method comprising administering to the subject or patient an effective amount of the poxvirus vector disclosed herein for a time and under conditions sufficient to elicit suppression/tolerance.

In another aspect of the present invention, there is provided a method of vaccinating a subject to induce tolerance to a peanut allergen comprising administering the poxvirus vector disclosed herein.

In another aspect of the present invention, there is provided a kit comprising the poxvirus vector disclosed herein.

The above summary is not and should not be seen in any way as an exhaustive of all embodiments of the present invention.

BRIEF DESCRIPTION OF THE FIGURES

FIG. 2 shows the nucleic acid sequence of the UBc.PHAV expression cassette.

FIG. 3 shows the nucleic acid sequence of the PHAVag construct expression cassette, without the ubiquitin sequence.

FIG. 5 lists the features of the homologous recombination cassette diagrammatically represented in FIG. 4.

FIG. 6 shows the nucleic acid sequence of the UBc.PHAV homologous recombination cassette.

FIG. 7 shows the nucleic acid sequence of the PHAV homologous recombination cassette.

FIG. 11 shows the levels of IFN-gamma (IFN-g; a $T_H1$ cytokine.

DETAILED DESCRIPTION

Figure 1A:
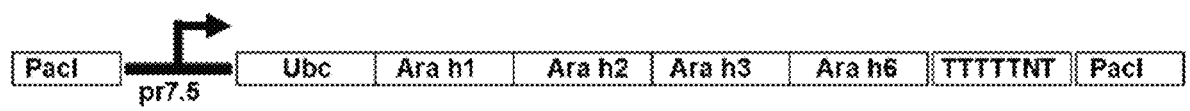
FIGS. 1A, 1B and 1C show an arrangement of the PHAV Antigen according to an embodiment of the present invention including a proteasome degradation tag and multiple peanut allergens (FIGS. 1A and 1B) and the PHAV Antigen according to an embodiment of the present invention without a proteasome degradation tag (FIG. 1C).

Reference to any prior art in this specification is not, and should not be taken as, an acknowledgment or any form of suggestion that this prior art forms part of the common general knowledge in any country.

Throughout this specification, unless the context requires otherwise, the words "comprise," "comprises" and "comprising" will be understood to imply the inclusion of a stated step or element or group of steps or elements but not the exclusion of any other step or element or group of steps or elements. Thus, use of the term "comprising" and the like indicates that the listed elements are required or mandatory, but that other elements are optional and may or may not be present. By "consisting of" is meant including, and limited to, whatever follows the phrase "consisting of". Thus, the phrase "consisting of" indicates that the listed elements are required or mandatory, and that no other elements may be present. By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that other elements are optional and may or may not be present depending upon whether or not they affect the activity or action of the listed elements.

As used herein the singular forms "a", "an" and "the" include plural aspects unless the context clearly dictates otherwise. Thus, for example, reference to "a composition" includes a single composition, as well as two or more compositions; reference to "an agent" includes one agent, as well as two or more agents; reference to "the invention" includes single and multiple aspects of the invention; and so forth.

Unless defined otherwise, all technical and scientific terms used herein have the same meanings as commonly understood by one of ordinary skill in the art to which this invention belongs. Any materials and methods similar or equivalent to those described herein can be used to practice or test the present invention.

The present specification enables a vaccine approach to the development of a therapeutic agent for treating or preventing peanut allergy. In particular, the specification enables an agent capable of providing therapy in the context of the major peanut allergens, e.g., at least one, at least two, at least three, etc, of the most widespread or troublesome peanut allergens.

The present invention is predicated on the inventors' surprising finding that a DNA vaccine comprising a nucleic acid construct operatively encoding a fusion protein, the fusion protein comprising a peanut allergen (such as ara h 1) linked to a proteasome degradation tag (such as ubiquitin), is capable of inducing an immune response in a subject that is biased towards a $T_H1$ phenotype, thus resulting in the secretion of peanut allergen-specific IgG antibodies, as opposed to peanut allergen-specific IgE antibodies that would otherwise facilitate an allergic reaction upon exposure to the peanut allergen.

Accordingly, In an aspect of the present invention, there is provided a poxvirus vector comprising a nucleic acid sequence encoding a fusion protein comprising (i) at least two peanut allergens selected from list consisting of ara h 1, ara h 2, ara h 3, ara h 4, ara h 5, ara h 6 and ara h 7 and a derivative or part thereof having at least 70% sequence identity thereto, and (ii) a proteasome degradation tag to enhance intracellular degradation of the fusion protein.

In another aspect of the present invention, there is provided a poxvirus vector comprising a nucleic acid sequence encoding a fusion protein comprising (i) at least two peanut allergens selected from list consisting of ara h 1, ara h 2, ara h 3, ara h 4, ara h 5, ara h 6, ara h 7, ara h 8, ara h 9, ara h10 and ara h 11 and a derivative or part thereof having at least 70% sequence identity thereto, and (ii) a proteasome degradation tag to enhance intracellular degradation of the fusion protein.

In another aspect of the present invention, there is provided a poxvirus vector comprising a nucleic acid sequence encoding a fusion protein comprising: (i) at least three peanut allergens selected from list consisting of ara h 1, ara h 2, ara h 3, ara h 4, ara h 5, ara h 6 and ara h 7 and a derivative or part thereof having at least 70% sequence identity thereto, and (ii) a proteasome degradation tag to enhance intracellular degradation of the fusion protein.

In another aspect of the present invention, there is provided a poxvirus vector comprising a nucleic acid sequence encoding a fusion protein comprising: (i) at least three peanut allergens selected from list consisting of ara h 1, ara h 2, ara h 3, ara h 4, ara h 5, ara h 6, ara h 7, ara h 8, ara h 9, ara h10 and ara h 11 and a derivative or part thereof having at least 70% sequence identity thereto, and (ii) a proteasome degradation tag to enhance intracellular degradation of the fusion protein.

In another aspect of the present invention, there is provided a poxvirus vector which expresses in the cell of a subject a fusion protein comprising: (i) a peanut allergen selected from list consisting of (a) at least two peanut allergens from ara h 1, ara h 2, ara h 3, ara h 4, ara h 5, ara h 6 and ara h 7 or a derivative or part thereof having at least 70% sequence identity thereto, or (b) at least three peanut allergens from ara h 1, ara h 2, ara h 3, ara h 4, ara h 5, ara h 6 and ara h 7, or a derivative or part thereof having at least 70% sequence identity thereto, and (ii) a proteasome degradation tag to enhance intracellular degradation of the fusion protein.

In another aspect of the present invention, there is provided a poxvirus vector which expresses in the cell of a subject a fusion protein comprising: (i) a peanut allergen selected from list consisting of (a) at least two peanut allergens from ara h 1, ara h 2, ara h 3, ara h 4, ara h 5, ara h 6 and ara h 7, ara h 8, ara h 9, ara h10 and ara h 11 or a derivative or part thereof having at least 70% sequence identity thereto, or (b) at least three peanut allergens from ara h 1, ara h 2, ara h 3, ara h 4, ara h 5, ara h 6, ara h 7, ara h 8, ara h 9, ara h10 and ara h 11 or a derivative or part thereof having at least 70% sequence identity thereto, and (ii) a proteasome degradation tag to enhance intracellular degradation of the fusion protein.

Peanut Allergens

Peanut allergens would be known to persons skilled in the art and include any peptide of the *Arachis hypogaea* species to which a subject may be exposed to through, for example, contact, inhalation, ingestion, injection, or the like. In an embodiment, the at least two peanut allergens are selected from the group consisting of ara h 1, ara h 2, ara h 3, ara h 4, ara h 5, ara h 6 and ara h 7. In another embodiment, the at least two peanut allergens are selected from the group consisting of ara h 1, ara h 2, ara h 3, ara h 4, ara h 5, ara h 6, ara h 7, ara h 8, ara h 9, ara h 10 and ara h 11.

The fusion protein can comprise any two or more peanut allergens ara h 1 to ara h 11. For example, the fusion protein may comprise the following peanut allergens:

(i) ara h 1, ara h 2, ara h 3, ara h 4, ara h 5, ara h 6, ara h 7, ara h 8, ara h 9, ara h 10 and ara h 11;
(ii) ara h 1, ara h 2, ara h 3, ara h 4, ara h 5, ara h 6, ara h 7, ara h 8, ara h 9 and ara h 10;
(iii) ara h 1, ara h 2, ara h 3, ara h 4, ara h 5, ara h 6, ara h 7, ara h 8 and ara h 9;
(iv) ara h 1, ara h 2, ara h 3, ara h 4, ara h 5, ara h 6, ara h 7 and ara h 8;
(v) ara h 1, ara h 2, ara h 3, ara h 4, ara h 5, ara h 6 and ara h 7;
(vi) ara h 1, ara h 2, ara h 3, ara h 4, ara h 5 and ara h 6;
(vii) ara h 1, ara h 2, ara h 3, ara h 4 and ara h 5;
(viii) ara h 1, ara h 2, ara h 3 and ara h 4;
(ix) ara h 1, ara h 2, ara h 3 and ara h 6;
(x) ara h 1, ara h 2 and ara h 3;
(xi) ara h 1 and ara h 2;
(xii) ara h 1 and ara h 3;
(xiii) ara h 1 and ara h 4;
(xiv) ara h 1 and ara h 5;
(xv) ara h 1 and ara h 6;
(xvi) ara h 1 and ara h 7;
(xvii) ara h 1 and ara h 8;
(xviii) ara h 1 and ara h 9;
(xix) ara h 1 and ara h 10;
(xx) ara h 1 and ara h 11;
(xxi) ara h 2 and ara h 3;
(xxii) ara h 2 and ara h 4; and so on.

By employing a proteasome degradation tag (e.g., ubiquitin) as a component of the fusion protein, the synthesized fusion protein is targeted to proteasomal degradation, resulting in the generation of small peptide fragments, which enter the endoplasmic reticulum (ER) where they are complexed with MHC class I proteins and then transported to the cell surface to be presented to T lymphocytes. As a consequence, there is enhanced presentation of the protein fragments with MHC class I. Thus, it would be understood by persons skilled in the art that, where the nucleic acid sequence encodes a fusion protein comprising two or more peanut allergens, the two or more peanut allergens can appear in the fusion protein in any particular order, as the expressed fusion protein will be subjected to proteasomal degradation.

It would be understood by persons skilled in the art that the choice of peanut allergen or allergens is likely to depend on the particular therapeutic and/or prophylactic application. For example, where the vaccine is to be used to induce tolerance in a subject who is allergic to peanut allergen Ara h1, then the fusion protein would desirably comprise ara h 1; where the vaccine is to be used to induce tolerance in a subject who is allergic to peanut allergen ara h 2, then the fusion protein would desirably comprise ara h 2; where the vaccine is to be used to induce tolerance in a subject who is allergic to peanut allergens ara h 1 and ara h 2, then the fusion protein would desirably comprise ara h 1 and ara h 2; and so on.

In an embodiment, the peanut allergen is selected from the group including: arah 1, Clone P41B (GenBank Accession number L34402 or Swiss-Prot: P43238.1); ara h 1 Clone P17 (GenBank Accession number L38853); ara h 2 cDNA (GenBank Accession number L7797 L77197 or UniProtKB/TrEMBL: Q8GV20); ara h 3 cDNA (GenBank Accession number AF093541 or ACH91862); ara h 4 cDNA (GenBank Accession number AF086821); ara h 5 cDNA (GenBank Accession number AF059616); ara h 6 cDNA (GenBank Accession number AF092846 or UniProtKB/TrEMBL: Q647G9), ara h 7 cDNA (GenBank Accession number AF091737), ara h 8 (GenBank Accession number AY328088, EF436550), ara h 9 (GenBank Accession number EU159429, EU161278), ara h 10 (AY722694, AY722695) and ara h 11 (DQ097716).

In an embodiment, the fusion protein comprises at least four peanut allergens, more preferably at least four of the most common peanut allergens affecting individuals who are allergic to peanuts. In an embodiment, the fusion protein comprises peanut allergens ara h 1, ara h 2, ara h 3 and ara h 6.

As used herein, the term "peanut allergen", including specific examples such ara h 1, ara h 2, etc, is to be understood as also including a homologue or variant thereof. The term "homologue", as used herein with reference to homologs of nucleic acid sequences or polypeptides described herein (including, for example, any one of SEQ ID NOs: 1-12), should be understood to include, for example, orthologs, paralogs, mutants and variants of nucleic acids or polypeptides described herein. In some embodiments, the homologue comprises a nucleic acid or an amino acid sequence which comprises at least 70% sequence identity, at least 75% sequence identity, at least 80% sequence identity, at least 85% sequence identity, at least 90% sequence identity, at least 95% sequence identity, at least 96% sequence identity, at least 97% sequence identity, at least 98% sequence identity, or at least 99% sequence identity to the nucleic acid or amino acid sequence described herein.

Thus, in an embodiment, ara h 1 has an amino acid sequence of SEQ ID NO: 4 or an amino acid sequence having at least 70% identity thereto, ara h 2 comprises the amino acid sequence of SEQ ID NO:6 or an amino acid sequence having at least 70% identity thereto, ara h 3 comprises the amino acid sequence of SEQ ID NO:8 or an amino acid sequence having at least 70% identity thereto, and ara h 6 comprises the amino acid sequence of SEQ ID NO:10 or an amino acid sequence having at least 70% identity thereto.

In another embodiment, ara h 1 is encoded by the nucleic acid sequence of SEQ ID NO:3 or a nucleic acid sequence having at least 70% identity thereto, ara h 2 is encoded by the nucleic acid sequence of SEQ ID NO:5 or a nucleic acid sequence having at least 70% identity thereto, ara h 3 is encoded by the nucleic acid sequence of SEQ ID NO:7 or a nucleic acid sequence having at least 70% identity thereto and ara h 6 is encoded by the nucleic acid sequence of SEQ ID NO:9 or a nucleic acid sequence having at least 70% identity thereto.

The term "sequence identity" as used herein refers to the extent that sequences are identical on a nucleotide-by-nucleotide basis or an amino acid-by-amino acid basis over a window of comparison. Thus, a "percentage of sequence identity" is calculated by comparing two optimally aligned sequences over the window of comparison, determining the number of positions at which the identical nucleic acid base (e.g., A, T, C, G, I) or the identical amino acid residue (e.g., Ala, Pro, Ser, Thr, Gly, Val, Leu, Ile, Phe, Tyr, Trp, Lys, Arg, His, Asp, Glu, Asn, Gln, Cys and Met) occurs in both sequences to yield the number of matched positions, dividing the number of matched positions by the total number of positions in the window of comparison (i.e., the window size), and multiplying the result by 100 to yield the percentage of sequence identity. For the purposes of the present invention, "sequence identity" will be understood to mean the "match percentage" calculated by an appropriate method. For example, sequence identity analysis may be carried out using the DNASIS computer program (Version 2.5 for windows; available from Hitachi Software engineering Co., Ltd., South San Francisco, Calif., USA) using standard defaults as used in the reference manual accompanying the software. The sequence identity of the encompassed peanut allergen amino acid or nucleotide sequence is, in some embodiments, increased to at least 75%, or at least 80%, or at least 85%, or at least 90% or at least 95% or at least 98% sequence identity.

In some embodiments, the term "allergen" may also include a fragment of any one of the foregoing peptides. As such, the nucleic acid may comprise a nucleotide that encodes a fragment of one of the aforementioned peanut allergens.

In some embodiments, the peanut allergen includes a modified peanut allergen whereby repeat sequences of 8 or more bases are removed from a native peanut allergen sequence. In some embodiments, the fusion protein includes 2 or more peanut allergens. In some embodiments the fusion protein includes two or more peanut allergens, at least one of which is selected from the group consisting of ara h 1, ara h 2, ara h 3, ara h 4, ara h 5, ara h 6, ara h 7, ara h 8, ara h 9, ara h 10 and ara h 11. In some embodiments, the fusion protein includes ara h 1, ara h 2, ara h 3 and ara h 6, or homologues thereof.

In some embodiments, to facilitate expression of a single fusion protein, the nucleic acid is devoid of stop codons between two sequences encoding peanut allergens.

Proteasome Degradation Tag

The present inventors have surprisingly found that employing a proteasome degradation tag (such as ubiquitin) as a component of the fusion protein is able to overcome the apparent toxic and/or inhibitory effect that a non-ubiquitinated peanut allergen peptide construct has on recombinant expression. The use of a proteasome degradation tag targets the expressed fusion peptide to proteasomal degradation. As a result of ubiquitin-targeted proteasomal degradation, small peptide fragments of the fusion peptide (e.g. peptides of about 8-12 amino acids in length) enter the endoplasmic reticulum (ER) where they are complexed with MHC class I proteins and subsequently transported to the cell surface to be presented to T lymphocytes. As a result, there is enhanced presentation of the fusion peptide fragments with MHC class I, resulting in a greater $T_H1$ immune response to peanut allergens. Thus, the proteasome degradation tag unexpectedly prevents the intact peanut allergen peptide construct from inhibiting recombinant expression in a host cell and biases the immune response towards a $T_H1$ phenotype.

The proteasome degradation tag may be any tag that targets the fusion protein for proteasomal degradation. In some embodiments, the proteasome degradation tag may include a ubiquitin molecule or a ubiquitin binding domain. In an embodiment, the proteasome degradation tag is a ubiquitin monomer, an illustrative example of which is ubiquitin C. In some embodiments, the ubiquitin monomer comprises the amino acid sequence of SEQ ID NO:2 or an amino acid sequence having at least 70% nucleotide sequence identity thereto.

In some embodiments, the C-terminal of the ubiquitin monomer is an alanine residue.

In another embodiment, the ubiquitin monomer is encoded by the nucleotide sequence of SEQ ID NO: 1 or a nucleotide sequence having at least 70% nucleotide sequence identity thereto.

The sequence encoding the proteasome degradation tag may be placed before or after the sequence encoding the at least one peanut allergen (i.e. the protein degradation tag may be C-terminal or N-terminal fusion protein).

Ubiquitin molecules may be derived from any suitable species. For a vaccine intended for human treatment, the ubiquitin molecule may be a human ubiquitin molecule or a ubiquitin molecule from another animal species that may have been codon optimised for expression in human cells. In some embodiments, the ubiquitin molecule may be a ubiquitin C monomer. Once expressed, the ubiquitin molecule may attract and bind to other ubiquitin molecules to form a polyubiquitin chain on the fusion protein. The ubiquitin molecule and/or the polyubiquitin chain may direct the fusion protein for proteasomal degradation.

In some embodiments, the nucleic acid construct operably encodes multiple ubiquitin molecules or one or more sequences encoding a truncated or modified ubiquitin molecule. If multiple ubiquitin molecules are encoded, one or more start and stop codons may be removed to allow translation of the entire fusion protein.

In some embodiments, a truncated ubiquitin molecule may involve exclusion of the lysine closest to the C-terminal of the native ubiquitin molecule. In some embodiments, a modified ubiquitin molecule may have one or more lysines of the native sequence removed or replaced (e.g. with arginine) from the sequence. In some embodiments, the ubiquitin molecule may only have a single lysine.

In some embodiments, the C-terminal of the ubiquitin molecule may be modified. For example, the C-terminal glycine of the native molecule may be replaced with alanine. Replacing the glycine with alanine or another amino acid, may prevent protease cleavage of the proteasome degradation tag from the allergen. Replacement of the glycine with alanine may also allow for the formation of a covalent bond between the proteasome degradation tag and the allergen. This covalent bond may be resistant to protease cleavage.

In some embodiments the proteasome degradation tag may include a ubiquitin binding domain. The protein degradation tag may be a member of the UbL (ubiquitin-like)-UBA (ubiquitin-associated) domain-containing protein family. In this regard, the expressed fusion protein may attract binding of ubiquitin molecules to the binding domain, leading to proteasomal degradation of the fusion protein.

Fusion Protein

In some embodiments, the nucleic acid sequence encodes a fusion protein that has been optimized for expression in a subject. For example, the sequence for a peanut allergen fusion protein can be is optimized for expression in a human cell. Similarly, in some embodiments, the proteasome degradation tag is optimized for expression in a subject and/or may be a proteasome degradation tag cloned from the same species as the desired subject. In some embodiments, codon optimization involves replacing a codon with a different codon that encodes the same amino acid but is more efficiently or accurately translated in a target species (e.g. in humans).

In some embodiments, optimisation of a sequence for expression in a subject also includes the removal of repeat sequences. For example, in some embodiments, repeat sequences of 8 or more bases are removed from the peanut allergen sequence. This may be particularly important if the sequence is constructed synthetically by back translation. Synthetic sequences generally lack the benefit of codon optimization through evolution. Therefore, disrupting randomly occurring destabilizing repeat sequences within the sequence by changing nucleotide bases without changing the amino acid sequence may improve expression of the sequence.

In some embodiments, the proteasome degradation tag is encoded by a nucleic acid sequence according to SEQ ID NO: 1 or a homologue thereof. In some embodiments, the peanut allergens of the fusion protein are encoded by a nucleic acid sequence according to SEQ ID NO: 3, SEQ ID NO: 5, SEQ ID NO: 7, and/or SEQ ID NO: 9, or a homologue of any one of the foregoing.

In some embodiments, the proteasome degradation tag comprises an amino acid sequence according to SEQ ID NO: 2. In some embodiments, the peanut allergens of the fusion protein comprise an amino acid sequence according to SEQ ID NO: 4, SEQ ID NO: 6, SEQ ID NO: 8, and/or SEQ ID NO: 10.

As conformational epitopes are not required for MHC-1 presentation and in some respects unwanted in order to prevent allergen-specific IgE antibody binding, the allergens expressed as part of the fusion protein are not required to be in their native structural form. This can allow for fusion proteins including multiple peanut allergens to be used and provides flexibility in the design of the fusion protein.

Accordingly, in some embodiments, the nucleic acid construct operably encodes 2 or more peanut allergens. For example, the fusion protein may encode 2, 3, 4, 5, 6, 7, 8, 9, 10 or more peanut allergens. For some nucleic acids, at least one of the allergens may be selected from the following peanut allergens or homologues thereof: ara h 1, ara h 2, ara h 3, ara h 4, ara h 5, ara h 6, ara h 7, ara h 8, ara h 9, ara h 10 or ara h 11. In an illustrative example, the nucleic acid construct operably encodes ara h 1, ara h 2, ara h 3 and ara h 6, or homologues thereof. For example, the nucleic acid construct may include a nucleic acid sequence according to SEQ ID NO: 11 or may encode a protein with an amino acid sequence according to SEQ ID NO: 12.

Each allergen may be fused to its own proteasome degradation tag and may be operably connected to its own promoter (e.g. multiple fusion proteins may be expressed). Alternatively, the sequences for the proteasome degradation tag and the allergens may be arranged to allow for expression of a fusion protein including a proteasome degradation tag and the multiple allergens. This latter approach can prevent differential expression of the different allergens and/or prevent intramolecular recombination if multiple expression cassettes are used with identical promoters.

To allow translation of a fusion protein with 2 or more allergens, the nucleic acid may be devoid of stop codons between two sequences encoding peanut allergens. In some embodiments, the nucleic acid sequence may be devoid of stop codons between any of the sequences encoding peanut allergens and/or may be devoid of stop codons between the sequence encoding the proteasome degradation tag and a sequence encoding an allergen.

To drive translation, the sequence encoding the first part of the fusion protein may include a start codon at the 5' end of the sequence. Start codons may be absent from the sequence encoding the rest of the fusion protein. In this regard, expression of allergens that are not fused to the proteasome degradation tag may be minimized or prevented. This can minimize or prevent intact peanut allergens from being secreted from the cell or presented on the surface of the cell, which could otherwise stimulate a $T_H2$ immune response against the allergen.

In an embodiment, the fusion protein comprises the amino acid sequence of SEQ ID NO: 12 or an amino acid sequence having at least 70% identity thereto.

In another embodiment, the fusion protein is encoded by the nucleic acid sequence of SEQ ID NO: 11 or a nucleic acid sequence having at least 70% identity thereto.

In some embodiments, and in order to facilitate expression of the fusion protein as an intact protein and reduce differential expression of each allergen, the vector comprises a transcription control sequence (such as a promoter) and single start codon to facilitate expression of the intact fusion protein.

In some aspects, the present invention provides a nucleic acid cassette for desensitizing or inducing tolerance in a subject to a peanut allergen, the cassette including: i) the vaccine as described herein and ii) a terminal restriction enzyme linker at each end of the sequence of the cassette. In some embodiments, at least one terminal restriction enzyme linker includes a Pac1 restriction enzyme recognition/cleavage sequence. In some embodiments the cassette is a viral vector cassette.

The nucleic acid construct may advantageously include a transcriptional control sequence operably connected to the nucleic acid sequence encoding the fusion protein.

The term "transcriptional control sequence" is to be understood to include any nucleic acid sequence which effects the transcription of an operably connected nucleic acid. Suitable transcriptional control sequences would be known to persons skilled in the art. Illustrative examples include a leader, polyadenylation sequence, promoter, enhancer or upstream activating sequence, and transcription terminator. Typically, a transcriptional control sequence at least includes a promoter. The term "promoter" as used herein, describes any nucleic acid which confers, activates or enhances expression of a nucleic acid molecule in a cell.

In some embodiments, at least one transcriptional control sequence is operably connected to the nucleic acid encoding the fusion protein. For the purposes of the present invention, a transcriptional control sequence is regarded as "operably connected" to a given gene or nucleotide sequence when the transcriptional control sequence is able to promote, inhibit or otherwise modulate the transcription of the gene or other nucleotide sequence.

A promoter may regulate the expression of an operably connected nucleotide sequence constitutively, or differentially, with respect to the cell, tissue, organ or developmental stage at which expression occurs, in response to external stimuli such as physiological stresses, pathogens, or metal ions, amongst others, or in response to one or more transcriptional activators. As such, the promoter used in accordance with the vaccine and/or methods of the present invention may include, for example, a constitutive promoter, an inducible promoter, a tissue-specific promoter or an activatable promoter. The present invention contemplates the use of any promoter which would be active in a cell of interest.

"Tissue specific promoters" include promoters which are preferentially or specifically expressed in one or more specific cells, tissues or organs in an organism and/or one or more developmental stages of the organism. It should be understood that a tissue specific promoter also be constitutive or inducible.

The promoter may also be a promoter that is activatable by one or more transcriptional activators, referred to herein as an "activatable promoter". For example, the activatable promoter may comprise a minimal promoter operably connected to an Upstream Activating Sequence (UAS), which comprises, inter alia, a DNA binding site for one or more transcriptional activators.

As referred to herein the term "minimal promoter" should be understood to include any promoter that incorporates at least a RNA polymerase binding site and, optionally a TATA box and transcription initiation site and/or one or more CAAT boxes.

As set out above, the activatable promoter may comprise a minimal promoter fused to an Upstream Activating Sequence (UAS). The UAS may be any sequence that can bind a transcriptional activator to activate the minimal promoter. Exemplary transcriptional activators include, for example: yeast derived transcription activators such as Ga14, Pdr1, Gcn4 and Ace 1; the viral derived transcription activator, VP16; Hap 1 (Hach et al., *J Biol Chem* 278: 248-254, 2000); Gaf1 (Hoe et al., *Gene* 215(2): 319-328, 1998); E2F (Albani et al., *J Biol Chem* 275: 19258-19267, 2000); HAND2 (Dai and Cserjesi, *J Biol Chem* 277: 12604-12612, 2002); NRF-1 and EWG (Herzig et al., *J Cell Sci* 113: 4263-4273, 2000); P/CAF (Itoh et al., *Nucl Acids Res* 28: 4291-4298, 2000); MafA (Kataoka et al., *J Biol Chem* 277: 49903-49910, 2002); human activating transcription factor 4 (Liang and Hai, *J Biol Chem* 272: 24088-24095, 1997); Bc110 (Liu et al., *Biochem Biophys Res Comm* 320(1): 1-6, 2004); CREB-H (Omori et al., *Nucl Acids Res* 29: 2154-2162, 2001); ARR1 and ARR2 (Sakai et al., *Plant J* 24(6): 703-711, 2000); Fos (Szuts and Bienz, *Proc Natl Acad Sci USA* 97: 5351-5356, 2000); HSF4 (Tanabe et al., *J Biol Chem* 274: 27845-27856, 1999); MAML1 (Wu et al., *Nat Genet* 26: 484-489, 2000).

The transcriptional control sequence may also include a terminator. The term "terminator" refers to a DNA sequence at the end of a transcriptional unit which signals termination of transcription. Terminators are 3'-non-translated DNA sequences generally containing a polyadenylation signal, which facilitate the addition of polyadenylate sequences to the 3'-end of a primary transcript. As with promoter sequences, the terminator may be any terminator sequence which is operable in the cells, tissues or organs in which it is intended to be used. In some embodiments, the nucleic acid sequence may include a viral early transcriptional stop sequence 3' of the sequence encoding the fusion protein.

Vectors

In an embodiment, the nucleic acid construct is operably incorporated in a vector.

In some embodiments, the vector may be an expression vector adapted for expression in a eukaryotic cell. As used herein, a "vector" may be any of a number of nucleic acids into which a desired sequence may be inserted. Vectors include, but are not limited to, plasmids, phagemids and virus genomes. In some embodiments, the expression vector is also able to be replicated in a host cell (e.g. a bacterial cell), and may also further comprise one or more endonuclease restriction sites at which the vector may be cut in a determinable fashion and into which a desired DNA sequence may be ligated such that the recombinant vector retains its ability to replicate in the host cell. In the case of plasmids, replication of the desired sequence may occur many times as the plasmid increases in copy number within the host bacterium or just a single time per host before the host reproduces by mitosis. In the case of phage, replication may occur actively during a lytic phase or passively during a lysogenic phase.

Expression vectors may contain transcriptional control sequences to drive expression of inserted nucleic acids in target cells (e.g. in a human cell). Transcriptional control sequences include those described above and include, for example, promoters.

Vectors may further contain one or more selectable marker sequences suitable for use in the identification of cells which have or have not been transformed or transfected with the vector. Markers include, for example, genes encoding proteins which increase or decrease either resistance or sensitivity to antibiotics or other compounds, genes which encode enzymes whose activities are detectable by standard assays known in the art (e.g., fl-galactosidase, luciferase), and genes which visibly affect the phenotype of transformed or transfected cells, hosts, colonies or plaques (e.g., various fluorescent proteins such as green fluorescent protein, GFP). Some vectors may be capable of autonomous replication, also referred to as episomal vectors. Alternatively vectors may be adapted to insert into a chromosome, so called integrating vectors. The vector may be provided with transcription control sequences (promoter sequences) which mediate cell/tissue specific expression. These promoter sequences may be cell/tissue specific, inducible or constitutive.

In some embodiments, the vector may be a viral vector. Suitable viral vectors would be known to persons skilled in the art. Illustrative examples of viral vectors include a retroviral vector, a lentiviral vector, an adenoviral vector, an adeno-associated viral vector, or a poxvirus viral vector. Poxviral vectors may include, for example, an avipox viral vector (e.g. fowlpox or canary pox). In some embodiments, the poxvirus viral vector may be a replication restricted viral vector including, for example, Modified Vaccinia Ankara (MVA) virus, an avipox virus or a crippled vaccinia virus. Use of viral vectors may be beneficial in further biasing a $T_H1$ response against cells expressing the degraded peanut allergen peptide fragments on MHC Class I molecules as the viral vector itself may promote IL-12 receptor expression on the cells. Furthermore, the activation of immune cells by viral vectors may initiate a complex network of cell-cell interactions and cytokine production cascades that result in the overall enhancement of $T_H1$ immune functions in an antigen-dependant manner.

In an embodiment, the viral vector is a poxvirus viral vector.

In some embodiments, the nucleic acid sequence includes a viral early transcriptional stop sequence 3' of the sequence encoding the fusion protein.

To facilitate cloning, the nucleic acid construct may be included in a nucleic acid cassette (i.e., an expression cassette). Accordingly, in some embodiments, the present invention provides a nucleic acid cassette for desensitizing a subject to a peanut allergen, the cassette including: the nucleic acid construct operably encoding the fusion protein as described herein and a terminal restriction enzyme linker at each end of the sequence of the cassette.

The term "nucleic acid cassette" as used herein is intended to mean a nucleic acid sequence designed to introduce a nucleic acid molecule (e.g., the nucleic acid construct as described herein) into a vector or genome.

The cassette will typically include a terminal restriction enzyme linker at each end of the sequence of the cassette. The terminal restriction enzyme linkers at each end may be the same or different terminal restriction enzyme linkers. In some embodiments, having the same terminal restriction enzyme linkers at each end can be advantageous if replication of the cassette in bacterial cells is desired (and the cassette includes an origin of replication) as the cassette may be circularized by digesting the cassette with the appropriate restriction enzyme and ligating the ends together. Similarly, a circular cassette may be linearised by digesting the cassette with a single restriction enzyme.

In some embodiments, the terminal restriction enzyme linkers may include rare restriction enzyme recognition/cleavage sequences, such that unintended digestion of the nucleic acid or the vector or genome into which the cassette is to be introduced does not occur. In some embodiments, the terminal restriction enzyme linkers include a Pac1 restriction enzyme recognition/cleavage sequence.

The cassette may be cloned into a mammalian expression vector, a bacterial expression or cloning vector, an insect expression vector, a plant expression vector or a viral vector. Accordingly, the cassette may be a mammalian vector cassette, a bacterial vector cassette, an insect vector cassette, a plant vector cassette or a viral vector cassette.

Treatment and Prevention of Peanut Allergy

The present inventors have surprisingly found that the vaccine of the present invention produces a biased anti-peanut protein $T_H1$ immune response, which will dominate over an existing allergen-specific $T_H2$ immune response and, in doing so, will desensitize an individual to subsequent exposure to the peanut allergen. Furthermore, expression of $T_H1$ cytokines (e.g. IFNγ, IL-12, TGF-β, IL2, etc.) can reduce the expression of $T_H2$ cytokines (e.g. IL-3, IL-4, IL-5, IL6, IL10, etc.), biasing the immune response against the allergen towards a $T_H1$ immune response, the result of which is the inhibition or amelioration of the activation and/or recruitment of IgE antibody producing B cells, mast cells and eosinophils, thereby reducing or preventing an allergic reaction to subsequent allergen exposure (e.g., anaphylactic reactions). Accordingly, the vaccine of the present invention is suitable for use in the treatment of a peanut allergy in a subject.

The present inventors have also surprisingly found that the vaccine of the present invention produces a biased $T_H1$ immune response to peanut allergen that is independent of a pre-existing peanut allergy. Accordingly, the vaccine of the present invention is suitable for use in the prevention of a peanut allergy in a subject who may be at risk thereof.

Thus, in another aspect, there is provided use of the poxvirus vector disclosed herein in, or in the manufacture of a medicament for, inducing tolerance in a subject to a peanut allergen.

In an embodiment, the poxvirus vector disclosed herein is used as a prophylactic to prevent or ameliorate peanut allergy in a subject at risk of developing a peanut allergy (i.e. tolerance may be induced in a subject at risk of developing allergy to a peanut allergen). Subjects at risk of developing a peanut allergy may include people already suffering from an allergy such as hayfever, asthma or other food allergies or people that have a family history of allergies.

In another aspect, there is provided a method of inducing tolerance in a subject to a peanut allergen, the method comprising administering to a subject in need thereof an effective amount of the poxvirus vector disclosed herein for a time and under conditions sufficient to elicit suppression and/or tolerance, for example, by inducing a peanut allergen-specific $T_H1$ response in the subject.

The terms "allergic reaction", "allergy", "allergic disorder" and the like, as used herein, are to be understood as meaning an immune disorder in which the immune system is hypersensitive to otherwise harmless environmental substances. These environmental substances that cause allergies are called "allergens." Common allergies include seasonal rhinoconjuctivitis (e.g., allergies to grasses and pollen such as ragweed, timothy grass), allergies to pet dander such as cat dander or dog dander, food allergies such as peanut, dairy and wheat allergies, venom anaphylaxis, and asthma. An allergic disorder is typically characterised by the production of IgE.

Allergic diseases result from immune responses against otherwise harmless environmental antigens, characterised by the generation of $T_H2$ T cells, which produce IL-4 and IL-5 and promote the differentiation of B cells into IgE antibody secreting cells. IgE antibodies bind to high affinity receptors on basophils and mast cells. Allergen exposure leads to binding of allergen molecules by surface IgE and cross linking of the receptors thus causing activation and degranulation of basophils and mast cells. The latter release a variety of preformed proinflammatory and vasoactive compounds such as histamine, prostaglandins, leukotriens and cytokines, leading to inflammatory response. Binding of peanut allergen to the IgE antibodies that are bound to the surface of mast cells and basophils is the initiating event that eventually culminates in an allergic reaction. Preventing allergen binding to mast cell- and/or basophil-bound IgE will prevent the onset of an allergic reaction. The prevention of allergen specific IgE production upon exposure to peanut allergen will induce tolerance to peanut.

The term "tolerance", as used herein, is taken to mean an inhibition (partial or complete) of an allergic reaction to peanut allergen exposure. Inhibition may be prevention, retardation, reduction, abrogation or otherwise hindrance of an allergic reaction. Such inhibition may be in magnitude and/or be temporal in nature. In particular contexts, the terms "inhibit" and "prevent", and variations thereof may be used interchangeably. Tolerance can be assessed by any means known to persons skilled in the art. As an illustrative example, a skin-prick test can be used to measure the subject's response to an allergen or multiple allergens, before and/or after treatment with the poxvirus vector disclosed herein. For example, in a subject who is allergic to peanuts, a skin-prick test using one or more peanut allergens will typically produce an observable localised allergic response characterised by a localised rash, urticaria and/or swelling. Tolerance in the same individual following treatment with the poxvirus vector disclosed herein will typically manifest itself as a reduced localised allergic reaction to the skin-prick test. This reduction can be measured, for example, by the difference in size (e.g., diameter) of the localised allergic reaction before and after treatment.

In another illustrative example, tolerance is assessed by the prevention, retardation, inhibition, reduction, abrogation or hindrance of the severity of allergic response following accidental exposure to a peanut allergen. For example, where a subject has a history of anaphylactic responses to peanut allergen exposure, tolerance as a result of treatment with the poxvirus vector in accordance with the present invention may be determined by the absence of an anaphylactic reaction following subsequent peanut allergen exposure, even though the subject may show other signs of an allergic reaction, such as a rash.

In another illustrative example, tolerance is assessed by determining the level of circulating peanut allergen-specific IgE antibodies in a subject. For instance, a subject who has a history of allergic reactions (including anaphylactic responses) to peanut allergen exposure will typically have a higher level of peanut allergen-specific IgE antibodies as compared, for example, to a subject who does not have a peanut allergy. In such individuals, tolerance may be determined by a reduction in the level of circulating peanut allergen-specific IgE antibodies following treatment with the vaccine of the present invention. Alternatively, or in addition, tolerance may be determined by a higher level of circulating peanut allergen-specific IgG antibodies following treatment with the poxvirus vector of the present invention, which is characteristic of a $T_H1$ immune response and typically indicative of a tolerant state.

Alternatively, or in addition, tolerance may be determined by assessing the cytokine profile in a sample obtained from the subject (e.g., a blood sample, including a plasma or serum sample). For example, a higher level of IFN-gamma is indicative of a bias towards an allergen-specific $T_H1$ response, whereas a higher level of IL-4 and/or IL-5 is indicative of a bias towards an allergen-specific $T_H2$ response.

Alternatively, or in addition, tolerance may be determined by obtaining a sample of T lymphocytes from a subject who has been treated with the poxvirus vector in accordance with the present invention, as disclosed herein, and measuring the cytokine profile of the lymphocytes ex vivo. For example, a higher level of IFN-gamma production by the T lymphocytes is indicative of a bias towards an allergen-specific $T_H1$ response, whereas a higher level of IL-4 and/or IL-5 production by the T lymphocytes is indicative of a bias towards an allergen-specific $T_H2$ response. Methods of measuring the level of peanut allergen-specific IgE and/or IgG antibodies and cytokines that are capable of differentiating between a $T_H1$ and $T_H2$ response would be know to persons skilled in the art. Illustrative examples include radioimmunoassays (RIA) and enzyme linked immunosorbant assays (ELISA).

It would be understood by persons skilled in the art that the poxvirus vector disclosed herein is to be administered in either in a single dose or as part of a series of doses that provides the desired therapeutic or prophylactic effect in a subject in need thereof; namely, the induction of tolerance to a peanut allergen. Undesirable effects, e.g. side effects, may sometimes manifest along with the desired therapeutic and/or prophylactic effect; hence, a practitioner will generally balance the potential benefits against the potential risks in determining an appropriate effective amount. The exact amount of vaccine required will vary from subject to subject, depending on the species, age and general condition of the subject, mode of administration and the like. Thus, it may not be possible to specify an exact effective amount. However, an appropriate effective amount in any individual case may be determined by one of ordinary skill in the art using routine skills or experimentation. One of ordinary skill in the art would be able to determine the required amounts based on such factors as the subject's size and weight, the severity of a subject's symptoms, and the proposed route of administration.

The term "treatment" refers to any measurable or statistically significant inhibition or amelioration in at least some subjects in one or more symptoms of peanut allergy.

In some embodiments, the poxvirus vector disclosed herein is exploited to desensitise a subject with a peanut allergy (i.e. a subject who is hypersensitive to one or more peanut allergens) to one or more peanut allergens. The term "desensitizing a subject" as used herein with reference to a peanut allergen is intended to mean that the sensitivity of the subject to the peanut allergen is reduced, ameliorated or eliminated. In this regard, symptoms of a peanut allergy in a subject are partially or completely reduced upon re-exposure to one or more peanut allergens.

In some embodiments, alternatively, or in addition, the nucleic acid sequence is exploited to induce tolerance in a subject to one or more peanut allergens. Induction of tolerance to the one or more peanut allergens is performed in a subject with a peanut allergy or in a subject who may be at risk of developing a peanut allergy (i.e. the nucleic acid may be exploited as part of a prophylactic treatment of peanut allergy).

While the poxvirus vector disclosed herein is exploited in different ways to desensitize or induce tolerance in a subject to a peanut allergen (as described herein), the general principle by which the poxvirus vector operates is the same. When the fusion peptide is expressed in a cell, it is targeted to proteasomal degradation by virtue of the proteasome degradation tag, which prevents the intact fusion protein from being secreted from the cell.

In an embodiment, there is provided a method of vaccinating a subject to induce tolerance to a peanut allergen comprising administering the poxvirus vector as disclosed herein. In a particular embodiment, the method is for inducing tolerance against at least two or at least three major peanut allergens.

The present invention extends to kits comprising the poxvirus vector, as disclosed herein.

The poxvirus vector of the present invention may be delivered to a cell in vivo or ex vivo (e.g. as naked DNA or in a vector) by methods known in the art. Illustrative examples include viral delivery, microinjection, gene gun, impalefection, hydrostatic pressure, electroporation, sonication, and/or lipofection. The poxvirus vector may also be delivered to a cell as a pharmaceutical composition.

Liposomes may serve as a carrier for the poxvirus vector. Liposomes are lipid-based vesicles which encapsulate a selected therapeutic agent (e.g. a vector) which is then introduced into a patient. The liposome may be manufactured either from pure phospholipid or a mixture of phospholipid and phosphoglyceride. Typically, liposomes can be manufactured with diameters of less than 200 nm, which enables them to be intravenously injected and able to pass through the pulmonary capillary bed. Furthermore, the biochemical nature of liposomes confers permeability across blood vessel membranes to gain access to selected tissues.

The poxvirus vector may be naked, that is, unassociated with any proteins or other agents which may affect the recipients' immune system. In this case, it is desirable for the poxvirus vector be in a physiologically acceptable solution, such as, but not limited to, sterile saline or sterile buffered saline. Alternatively, the vaccine may be associated with liposomes, such as lecithin liposomes or other liposomes known in the art. Agents which assist in the cellular uptake of nucleic acid molecules, such as, but not limited to, calcium ions, may also be used.

In the case of non-viral vectors, the amount of nucleic acid to be introduced into a recipient will have a very broad dosage range and may depend, for example, on the strength of the transcriptional and translational promoters used. In addition, the magnitude of the immune response may depend on the level of protein expression and on the immunogenicity of the expressed fusion protein product. An effective dose range may include about 1 ng to 5 mg, about 100 ng to 2.5 mg, about 1 µg to 750 µg, or about 10 µg to 300 µg of the nucleic acid (e.g. as part of a poxvirus vector).

The poxvirus vector may be administered or inoculated, subcutaneously, intramuscularly, intradermally, or by other modes such as intraperitoneal, intravenous, or inhalation, in the presence of adjuvants or other substances that have the capability of promoting DNA uptake or recruiting immune system cells to the site of inoculation. The chosen route of administration will depend on the composition and the disease status of patients. Relevant considerations include the types of immune cells to be activated, the time which the antigen is exposed to the immune system and the immunization schedule. It is also contemplated that booster treatments may be provided.

As described herein, the poxvirus vector is able to desensitize (i.e., induce tolerance in) a subject by expression of the fusion protein in a cell. The fusion protein is degraded within the cell and the degraded peanut allergen fragments are expressed on the cell surface in association with MHC Class I molecules. In some embodiments, no intact expressed peanut allergen is exposed to the subject's immune system during the methods of the present invention. This is as a result of the proteasome degradation tag, which drives the intracellular proteasomal degradation of the expressed fusion protein.

The method of desensitizing or inducing tolerance in a subject to a peanut allergen may involve administering the poxvirus vector, or a pharmaceutical composition including the poxvirus vector to the subject. Accordingly, the present invention provides a method of desensitizing a subject to a peanut allergen, wherein the method includes expressing the fusion protein in a cell of the subject, wherein the proteasome degradation tag of the expressed fusion protein targets the fusion protein for intracellular proteasomal degradation and association of the degraded peptides of the peanut allergen with MHC class I molecules to promote generation of a $T_H1$ response to the peanut allergen, thus desensitizing or inducing tolerance in the subject to the peanut allergen.

The present invention also provides a prophylactic treatment method for inducing tolerance to a peanut allergen in a subject, wherein the method includes expressing the fusion protein in a cell of the subject, wherein the proteasome degradation tag of the expressed fusion protein targets the fusion protein for intracellular proteasomal degradation and association of the degraded peptides of the peanut allergen with MHC class I molecules to promote generation of a $T_H1$ response to the peanut allergen, thus preventing sensitivity of the subject to the peanut allergen.

While these methods may involve expressing the fusion protein in a cell in vivo, other methods may include expressing the fusion protein in a cell ex vivo. As such, the present invention also provides a cell expressing the fusion protein. In this regard, the cell may be used for in vitro experiments, in vivo treatment and/or ex vivo treatments.

Subject

The terms "subject," "individual" and "patient" are used interchangeably herein to refer to any subject to which the present disclosure may be applicable, particularly a vertebrate subject, and even more particularly a mammalian subject. Suitable vertebrate animals that fall within the scope of the invention include, but are not restricted to, any member of the subphylum Chordata including primates, rodents (e.g., mice rats, guinea pigs), lagomorphs (e.g., rabbits, hares), bovines (e.g., cattle), ovines (e.g., sheep), caprines (e.g., goats), porcines (e.g., pigs), equines (e.g., horses), canines (e.g., dogs), felines (e.g., cats), avians (e.g., chickens, turkeys, ducks, geese, companion birds such as canaries, budgerigars etc), marine mammals (e.g., dolphins, whales), reptiles (snakes, frogs, lizards, etc.), and fish. In some embodiments, the subject is a primate (e.g., a human, ape, monkey, chimpanzee).

In a preferred embodiment, the subject is a human. Accordingly, in some embodiments, the nucleic acid sequence encoding the fusion protein is codon optimized for expression in human cells.

Pharmaceutical Compositions

The poxvirus vector according to the present invention may be provided in a form comprising a pharmaceutically or physiologically acceptable carrier and/or diluent.

Thus, in another aspect, there is provided a pharmaceutical composition for desensitizing or inducing tolerance in a subject to a peanut allergen, the composition comprising the poxvirus vector disclosed herein and a pharmaceutically acceptable carrier.

Pharmaceutical compositions are conveniently prepared according to conventional pharmaceutical compounding techniques. See, for example, Remington's Pharmaceutical Sciences, 18th Ed., Mack Publishing, Company, Easton, Pa., U.S.A., 1990. These compositions may comprise, in addition to one of the active substances, a pharmaceutically acceptable excipient, carrier, buffer, stabilizer or other materials well known in the art. Such materials should be non-toxic and should not interfere with the efficacy of the active ingredient. The carrier may take a wide variety of forms depending on the form of preparation desired for administration, e.g. intravenous, oral or parenteral.

In some embodiments, the present invention provides a method of desensitizing or inducing tolerance in a subject to a peanut allergen, the method including expressing the fusion peptide as described herein in a cell of the subject, wherein the proteasome degradation tag of the expressed fusion protein targets the fusion protein for intracellular proteasomal degradation and association of the degraded peptides of the peanut allergen with MHC class I molecules to promote generation of a $T_H1$ response to the peanut allergen, thus desensitizing or inducing tolerance in the subject to the peanut allergen.

In some embodiments, the present invention provides a prophylactic treatment method for inducing tolerance to a peanut allergen in a subject, the method including expressing the fusion peptide as described herein in a cell of the subject, wherein the proteasome degradation tag of the expressed fusion protein targets the fusion protein for intracellular proteasomal degradation and association of the degraded peptides of the peanut allergen with MHC class I molecules to promote generation of a $T_H1$ response to the peanut allergen, thus preventing sensitivity of the subject to the peanut allergen.

The present inventors have surprisingly found that a poxvirus vector comprising a nucleic acid sequence encoding a fusion protein comprising peanut allergens and a proteasome degradation tag, can, upon vaccination, produce a peanut-specific $T_H1$ immune response, as measured by the production of peanut allergen-specific IgG2a antibodies and peanut allergen-induced secretion of $T_H1$ cytokines from lymphocytes. As this poxvirus vector stimulated a peanut allergen-specific $T_H1$ immune response, it follows that the poxvirus vector disclosed herein can be used to desensitize (i.e., induce tolerance in) subjects who are allergic to peanut allergens.

The present invention also provides a nucleic acid sequence for desensitizing or inducing tolerance in a subject to a peanut allergen, the nucleic acid including a sequence encoding a fusion protein, the fusion protein including a proteasome degradation tag and a peanut allergen. The nucleic acid may be used as a genetic vaccine.

As described herein, in some embodiments, the nucleic acid is included in an expression vector (e.g., a viral vector) or pharmaceutical composition which can be administered to a subject to allow expression of the ubiquitinated fusion protein in a cell in vivo. Alternatively, the nucleic acid is expressed in an ex vivo cell (e.g., an antigen presenting cell) that may then be administered to a subject. Alternatively, or in addition, the transfected cell can be used to stimulate and expand a $T_H1$ lymphocyte population ex vivo, which are then administered to the subject.

In some embodiments, establishment of $T_H1$ memory to the presented peptides of the peanut allergen can prevent or reduce $T_H2$ immune responses against the peanut allergen upon subsequent expose to a peanut allergen. In some embodiments, $T_H1$ memory against the peanut allergen is established by the activation and maintenance of peanut allergen specific $CD8^+$ T cells.

Cells

In another aspect of the present invention, there is provided a cell expressing the fusion protein as described herein, such as a host cell or an antigen presenting cell (e.g., a dendritic cell). The transfected cell expressing the fusion protein can then be used to generate and/or expand a peanut allergen reactive $T_H1$ lymphocyte population in vivo or ex vivo. Thus, in an embodiment, the present disclosure enables a method of generating and/or expanding a peanut allergen reactive $T_H1$ lymphocyte population ex vivo, the method comprising culturing the cell (i.e., a transfected cell expressing the fusion protein) as described herein with one or more T lymphocytes. In another embodiment, the present disclosure enables a method of generating and/or expanding a peanut allergen reactive $T_H1$ lymphocyte population in vivo, the method comprising administering a transfected cell as described herein in a subject in need thereof, wherein the administered transfected cell activates naïve T cells in the subject to become peanut allergen-specific $T_H1$ cells.

In some embodiments, the present invention provides a method of desensitizing or inducing tolerance in a subject to a peanut allergen, the method comprising: i) collecting lymphocytes from the subject; ii) co-culturing the lymphocytes with cells as described herein (i.e., transfected cells expressing the fusion protein disclosed herein) to generate and/or expand a $T_H1$ lymphocyte population that recognizes the proteasomally degraded peanut allergen fusion protein associated with MI-IC Class I molecules on the cells; and iii) administering the $T_H1$ lymphocytes from (ii) to the subject.

In some embodiments, the cell may include a prokaryotic cell (e.g. a bacterial cell). The prokaryotic cell may be used to replicate the nucleic acid construct (e.g. in vector form) and/or in various cloning steps. In some embodiments, the cell may include a eukaryotic cell (e.g. a mammalian cell). In this regard, the present invention also includes a cell expressing the nucleic acid construct operably encoding the fusion protein.

The poxvirus vector as disclosed herein can also be used to activate naïve antigen presenting cells, which can then be reintroduced back into the subject to activate naïve T cells to become peanut allergen-specific $T_H1$ cells. Thus, in some embodiments, the present invention provides a method of desensitizing or inducing tolerance in a subject to a peanut allergen, the method comprising: i) collecting antigen presenting cells from the subject; ii) co-culturing the antigen presenting cells with the cells as described herein (i.e., transfected cells expressing the fusion protein disclosed herein) to generate and/or expand a population of activated $T_H1$ antigen presenting cell population; and iii) administering the activated $T_H1$ antigen presenting cell from (ii) to the subject to activate T lymphocytes towards an allergen-specific $T_H1$ phenotype. Suitable naïve antigen presenting cells would be known to persons skilled in the art. Illustrative examples include dendritic cells and fibroblasts.

The cell type expressing the fusion protein is only limited in that the cell should be a nucleated cell that expresses an MHC Class I molecule. In this regard, the cell may be a cell from a cell line (e.g. a CHO cell line, HEK cell line, fibroblast cell line, etc.) or a primary cell (e.g., a fibroblast, a dendritic cell). In embodiments whereby the cell is intended as an ex vivo autologous treatment, the cell may be cell which may be readily removed from a subject (e.g. a cell in blood, lymph, bone marrow) and/or readily cultured from a tissue sample (e.g. fibroblast cells). In some embodiments, the cell may be a professional antigen presenting cell (e.g. a dendritic cell, macrophage, B-cell, epithelial cell, etc.) or may be a non-professional antigen presenting cell (e.g. a fibroblast, thymic epithelial cell, thyroid epithelial cell, glial cell, pancreatic beta cell, vascular endothelial cell, etc.).

Expressing the fusion protein in a cell ex vivo (e.g., transfecting the cell with the poxvirus vector disclosed herein) can be advantageous in that the number of cells expressing the nucleic acid may be controlled. Furthermore, a wider range of nucleic acid delivery systems are available for cells ex vivo. The cells expressing the fusion protein (i.e., the transfected cells) may then be administered to a subject to activate naïve T cells in the subject towards a peanut allergen-specific $T_H1$ phenotype, which can then desensitize or induce tolerance in the subject to one or more peanut allergens. Alternatively, the cells expressing the fusion protein may be cultured with lymphocytes ex vivo to generate peanut allergen reactive $T_H1$ lymphocytes, which may then be administered to the subject.

Accordingly, the present invention also provides a method of generating and/or expanding a peanut allergen reactive $T_H1$ lymphocyte ex vivo, wherein the method includes culturing a cell expressing the fusion protein with one or more T lymphocytes. The T lymphocytes may be included in a mixed lymphocyte population or may be isolated T lymphocytes. Mixed lymphocyte populations may be readily obtained from peripheral blood, lymph or bone marrow by methods known in the art. T cells may be isolated from such mixed lymphocyte populations by methods known in the art including, for example, nylon wool isolation, FACS sorting, magnetic bead separation, etc. In some embodiments, particular T lymphocyte subsets may be isolated for culturing with the cell expressing the nucleic acid.

It would be understood by persons skilled in the art that, where cells are transfected ex vivo to express the fusion protein and/or where a population of $T_H1$ lymphocytes are generated and/or expanded ex vivo, as disclosed herein, it is often desirable to use autologous cells (i.e., cells derived from the subject to be treated), thereby avoiding or minimising an immune response that may occur where allogeneic cells (i.e., cells derived from a different subject) are used and administered to the subject.

Ex vivo expansion of peanut allergen reactive $T_H1$ lymphocyte may be used to generate large numbers of peanut allergen reactive $T_H1$ lymphocyte, which may then be administered to a subject as a prophylactic or therapeutic treatment of peanut allergy. In some instances, ex vivo expansion may accelerate the activation and expansion of peanut allergen reactive $T_H1$ lymphocytes compared with in vivo activation and expansion. Furthermore, ex vivo expansion allows control over the number and reactivity of peanut allergen reactive $T_H1$ lymphocytes that are expanded. In some embodiments, the peanut allergen reactive $T_H1$ lymphocytes may be autologous to the subject.

Accordingly, the present invention also provides a method of desensitizing a subject to a peanut allergen, the method including: (i) collecting lymphocytes from the subject; (ii) co-culturing the lymphocytes with cells expressing the fusion protein to generate and/or expand a $T_H1$ lymphocyte that recognizes proteasomally degraded fusion protein peptide fragments associated with MHC Class I molecules on the cells; and (iii) administering the $T_H1$ lymphocytes from (ii) to the subject. In some embodiments, the lymphocytes are collected from the subject before administration of the poxvirus vector as disclosed herein.

In some embodiments, the method may include isolating the lymphocytes from step (ii) prior to administration to the subject. Isolating the lymphocytes from step (ii) may include isolating all lymphocytes from the cells expressing the nucleic acid and/or may include isolating one or more lymphocyte types (e.g. all T cells lymphocytes, all $T_H1$ lymphocytes, etc.). Alternatively, the $T_H1$ lymphocytes from (ii) may be administered to the subject without isolating the lymphocytes from the cells expressing the fusion protein, in which case the administered cells expressing the fusion protein may continue to activate further $T_H1$ lymphocytes in vivo. Methods for isolating lymphocytes from a subject, methods for isolating T cells and T cell subsets include those methods described above.

Also enabled herein are methods in which T lymphocytes are obtained, whether isolated or not, from the subject treated in accordance with the present invention, and determining whether the lymphocytes are biased towards a $T_H1$ phenotype, as disclosed herein (e.g., determining the cytokine expression profile ex vivo). This approach has the added advantage of determining whether the administration of the poxvirus vector has induced a $T_H1$-biased allergen-specific immune response in the subject. Thus, in some embodiments, the method includes determining whether the lymphocytes isolated from step (ii) are biased towards a $T_H1$ phenotype prior to their administration to the subject.

In some embodiments, desensitization or tolerance induction of a subject to a peanut allergen may prevent or reduce hypersensitivity reactions against subsequent exposure of the subject to peanuts. As such, the methods described above may reduce the risk of anaphylactic reactions to peanuts in subjects previously allergic to peanuts upon subsequent exposure of the subject to peanuts and/or reduce the risk of anaphylactic reactions to peanuts in subjects at risk of developing a peanut allergy.

The present invention is further described by the following non-limiting examples. It is to be understood that the following description is for the purpose of describing particular embodiments only and is not intended to be limiting with respect to the above description.

EXAMPLES

Materials and Methods

Production of a PHAV Antigen:

A nucleic acid sequence for a fusion protein (PHAV antigen) including a human Ubiquitin C monomer (Ubc) and four peanut allergens was designed as set out below and illustrated in FIG. 1A.

The amino acid sequence for Ubc (NM_021009), ara h 1 (Swiss-Prot entry P43238), ara h 2 (TrEMBL entry Q8GV20), ara h 3 (Genbank Protein ACH91862) and ara h 6 (UniProtKB/TrEMBL entry Q647G9) were obtained from online protein sequence databases. The start codon amino acid Met (M) was removed from ara h 1, ara h 2, ara h 3 and ara h 6 protein sequences before joining the sequences to form one continuous protein sequence in the order of: Ubc+ara h1+ara h2+ara h3+ara h6. The DNA sequence coding this PHAVag protein was obtained by back translation using a *Homo Sapiens* codon preferred table.

The PHAVag amino acid sequence was back translated into a nucleotide sequence using Gene Designer (DNA2.0 Inc) and employed a *Homo Sapiens* codon optimisation set at a 10% threshold. Repeat sequences of 8 bases or more were also filtered out. The resulting sequence was further screened for secondary structure formation potential and destabilising elements by DNA2.0 Inc. The final nucleotide sequence of the PHAVag protein sequence was screened for the pox virus early transcriptional motif "TTTTTNT". However, none were found.

At the end of the nucleotide sequence coding for the PHAV antigen, a "TAA" stop codon was added. The Pox virus early transcriptional stop sequence TTTTTAT was also added immediately after the stop codon. The expression cassette was flanked with Pac I linkers. As Pac I recognition sites were not present within the cassette, this cassette could be cloned into plasmids and excised whole from a plasmid by Pac I restriction endonuclease digestion.

As shown in Table 1, Ubc, ara h 1, ara h 2, ara h 3 and ara h 6 in the PHAV Antigen had around 75% nucleic acid sequence identity to the native sequences.

TABLE 1

Sequence comparison of PHAV Antigen components and native sequences

| | Nucleotide sequence comparison | | Amino acid sequence comparison | |
|---|---|---|---|---|
| | Number of differences to native sequence/ total length | % identity to native sequence | Number of differences to native sequence/ total length | % identity to native sequence |
| Ubc | 53/228 | 76.8% | 1/76 | 98.7% |
| Ara h 1 | 440/1875 | 76.5% | 0/625 | 100% |
| Ara h 2 | 124/513 | 75.8% | 0/171 | 100% |
| Ara h 3 | 405/1587 | 74.5% | 22/529 | 95.8% |
| Ara h 6 | 103/435 | 76.3% | 0/145 | 100% |

A summary of the nucleic acid and amino sequences of the PHAV Antigen construct and components thereof is set out in Table 2.

TABLE 2

Sequence Summary

| | Name | Sequence Type |
|---|---|---|
| 1 | Ubc | Nucleic acid |
| 2 | Ubc | Amino acid |
| 3 | ara h 1 | Nucleic acid |
| 4 | ara h 1 | Amino acid |
| 5 | ara h 2 | Nucleic acid |
| 6 | ara h 2 | Amino acid |
| 7 | ara h 3 | Nucleic acid |
| 8 | ara h 3 | Amino acid |
| 9 | ara h 6 | Nucleic acid |
| 10 | ara h 6 | Amino acid |
| 11 | PHAV Antigen | Nucleic acid |
| 12 | PHAV Antigen | Amino acid |

Production of an Alternative PHAV Antigen:

A ubiquitinated peanut hypo-allergy vaccine antigen (UBc.PHAVag) was made comprising a PHAV antigen protein sequence made up of a fusion of the following protein coding sequences—ubiquitin C monomer, the peanut allergen ara h 1, peanut allergen ara h 2, peanut allergen ara h 3 and peanut allergen ara h 6.), pox virus early transcriptional stop sequence and finally another Pac1 linker.

Figure 9:
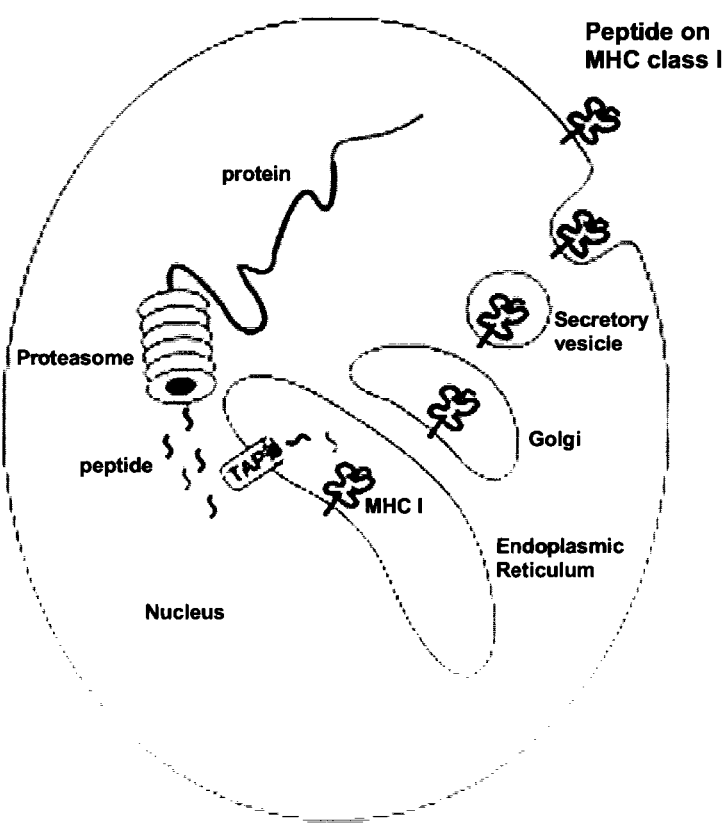
FIG. 9 is a diagrammatic representation of the proteasomal degradation pathway in a cell.

The ubiquitin C monomer was modified at the C-terminal to replace the terminal Gly (G) residue with Ala (A). The modified ubiquitin C targets the PHAV antigen upon synthesis to the proteasomal degradation pathway in the host cell (see FIG. 9). This ensures that no intact protein is presented for antibody production and that the resulting peptide fragments are processed by the MHC class I pathway, triggering a $T_H1$ immune response to the PHAV antigen.

Figure 1B:
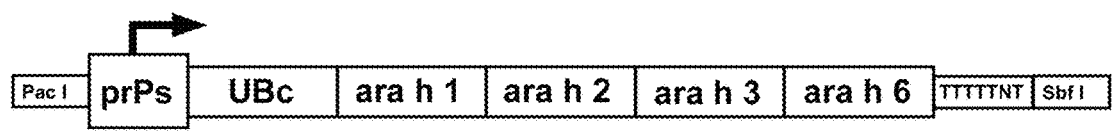

The configuration and features of the PHAV expression cassettes are shown diagrammatically in FIG. 1B and include Pac I restriction endonuclease linkers at the 5' and 3' ends, as well as a vaccinia early/late promoter at the 5'end.

The amino acid sequence for UBc, ara h 1, ara h 2, ara h 3 and ara h 6 were obtained from either Swit-Prot or EMBL protein databases. The start codon encoding a Met (M) residue was removed from the ara h 1, ara h 2, ara h 3 and ara h 6 nucleic acid sequences before joining then up to form the continuous nucleic acid sequence encoding the protein sequence UBc+h1+h2+h3+h6, in that order.

The DNA sequence for coding this UBc.PHAVag was obtained by back translation using a *Homo Sapiens* codon preferred table. The UBc.PHAVag amino acid sequence was back translated into a nucleotide sequence using Gene Designer (DNA2.0 Inc) and employing *Homo Sapiens* codon optimisation set at 10% threshold and filtering out repeat sequences of 8 bases or more. The resulting sequence was further screened for secondary structure formation potential and destabilising elements by DNA2.0 Inc. The final nucleotide sequence encoding UBc.PHAVag was screened for pox virus early transcriptional motif "TTTTTNT"—none were found. At the end of the nucleotide sequence coding for UBc.PHAV, "TAA" stop codon was added. The Pox virus early transcriptional stop sequence TTTTTAT was also added immediately after the stop codon. The expression cassette was flanked with Pac I linkers and because Pac I recognition sites are not present within the cassette, this cassette can be cloned into plasmids and excised whole from plasmid by Pac I restriction endonuclease digestion. The DNA sequence of the UBc.PHAV expression cassette can be found in FIG. 2.

Figure 1C:
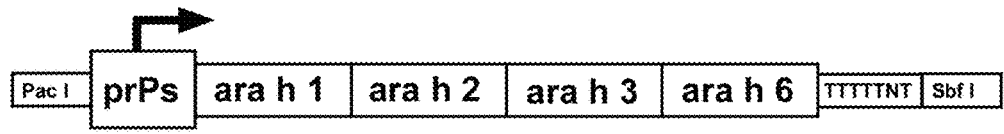

A peanut hypollergen vaccine antigen was also constructed in which the ubiquitin monomer at the 5' end was omitted. This construct was identical to the UBc.PHAVag construct, as described above, but without the ubiquitin sequence. This construct was referred to as PHAVag and a diagrammatic representation of the configuration and features of PHAVag can be found in FIG. 1C and the DNA sequence found in FIG. 3.

Both the UBc.PHAVag and PHAVag expression cassettes were cloned into bacterial plasmids so that these expression cassette could be retrieved after cloning by PacI/Sbf I digestion and gel purification.

Additional ubiquitinated peanut hypo-allergy vaccine antigens could be made that include the following peanut allergens:
(i) ara h 1, ara h 2, ara h 3, ara h 4, ara h 5, ara h 6, ara h 7, ara h 8, ara h 9, ara h 10 and ara h 11;
(ii) ara h 1, ara h 2, ara h 3, ara h 4, ara h 5, ara h 6, ara h 7, ara h 8, ara h 9 and ara h 10;
(iii) ara h 1, ara h 2, ara h 3, ara h 4, ara h 5, ara h 6, ara h 7, ara h 8 and ara h 9;
(iv) ara h 1, ara h 2, ara h 3, ara h 4, ara h 5, ara h 6, ara h 7 and ara h 8;
(v) ara h 1, ara h 2, ara h 3, ara h 4, ara h 5, ara h 6 and ara h 7;
(vi) ara h 1, ara h 2, ara h 3, ara h 4, ara h 5 and ara h 6;
(vii) ara h 1, ara h 2, ara h 3, ara h 4 and ara h 5;
(viii) ara h 1, ara h 2, ara h 3 and ara h 4;
(ix) ara h 1, ara h 2 and ara h 3;
(x) ara h 1 and ara h 2;
(xi) ara h 1;
(xii) ara h 2;
(xiii) ara h 2, ara h 3, ara h 4, ara h 5, ara h 6, ara h 7, ara h 8, ara h 9, ara h 10, and ara h 11;
(xiv) ara h 2, ara h 3, ara h 4, ara h 5, ara h 6, ara h 7, ara h 8, ara h 9 and ara h 10;
(xv) ara h 2, ara h 3, ara h 4, ara h 5, ara h 6, ara h 7, ara h 8 and ara h 9;
(xvi) ara h 2, ara h 3, ara h 4, ara h 5, ara h 6, ara h 7 and ara h 8;
(xvii) ara h 2, ara h 3, ara h 4, ara h 5, ara h 6 and ara h 7;
(xviii) ara h 2, ara h 3, ara h 4, ara h 5 and ara h 6;
(xix) ara h 2, ara h 3, ara h 4 and ara h 5;
(xx) ara h 2, ara h 3 and ara h 4;
(xxi) ara h 2 and ara h 3;
(xxii) ara h 3;
(xxiii) ara h 1, ara h 3, ara h 4, ara h 5, ara h 6, ara h 7, ara h 8, ara h 9, ara h 10 and ara h 11;
(xxiv) ara h 1, ara h 3, ara h 4, ara h 5, ara h 6, ara h 7, ara h 8, ara h 9 and ara h 10;
(xxv) ara h 1, ara h 3, ara h 4, ara h 5, ara h 6, ara h 7, ara h 8 and ara h 9;
(xxvi) ara h 1, ara h 3, ara h 4, ara h 5, ara h 6, ara h 7 and ara h 8;
(xxvii) ara h 1, ara h 3, ara h 4, ara h 5, ara h 6 and ara h 7;
(xxviii) ara h 1, ara h 3, ara h 4, ara h 5 and ara h 6;
(xxix) ara h 1, ara h 3, ara h 4 and ara h 5;
(xxx) ara h 1, ara h 3 and ara h 4;
(xxxi) ara h 1 and ara h 3;
(xxxi) ara h 1, ara h 2, ara h 4, ara h 5, ara h 6, ara h 7, ara h 8, ara h 9, ara h 10 and ara h 11;
(xxxiii) ara h 1, ara h 2, ara h 4, ara h 5, ara h 6, ara h 7, ara h 8, ara h 9 and ara h 10;
(xxxiv) ara h 1, ara h 2, ara h 4, ara h 5, ara h 6, ara h 7, ara h 8 and ara h 9;
(xxxv) ara h 1, ara h 2, ara h 4, ara h 5, ara h 6, ara h 7 and ara h 8;
(xxxvi) ara h 1, ara h 2, ara h 4, ara h 5, ara h 6 and ara h 7;
(xxxvii) ara h 1, ara h 2, ara h 4, ara h 5 and ara h 6;
(xxxviii) ara h 1, ara h 3, ara h 4 and ara h 5;
(xxxix) ara h 1, ara h 2 and ara h 4;
(xl) ara h 1, ara h 4, ara h 5, ara h 6, ara h 7, ara h 8, ara h 9, ara h10 and ara h 11;
(xli) ara h 1, ara h 4, ara h 5, ara h 6, ara h 7, ara h 8, ara h 9 and ara h 10;
(xlii) ara h 1, ara h 4, ara h 5, ara h 6, ara h 7, ara h 8 and ara h 9;
(xliii) ara h 1, ara h 4, ara h 5, ara h 6, ara h 7 and ara h 8;
(xliv) ara h 1, ara h 4, ara h 5, ara h 6 and ara h 7;
(xlv) ara h 1, ara h 4, ara h 5 and ara h 6;
(xlvi) ara h 1, ara h 4 and ara h 5;
(xlvii) ara h 1 and ara h 4;
(xlviii) ara h 4; and so on.

The amino acid sequences for ara h1, h2, h3, h4, h5, h6, h7, h8, h9, h10 and h11 are readily obtained from either Swit-Prot or EMBL protein databases. The start codon encoding a Met (M) residue and also the stop codon would be removed from the ara h nucleic acid sequences before joining them up to form a continuous nucleic acid sequence encoding a fusion protein of any two or more of the ara h proteins, and in any particular order. However, a start codon would be required at the start of the fusion protein coding sequence and stop codon to terminate expression of the encoded fusion protein.

Construction of Vaccinia Virus Homologous Recombination Plasmid:

The homologous recombination cassette consist of the following element, all of which were synthetically made by GeneArt GmbH of Life Technologies: (i) 500 bp left homologous recombination arm that flanks up-stream of the VACV-A39R ORF of the Copenhagen strain, (ii) EGFP expression cassette under the control of a vaccinia early/late promoter and terminating in the poxvirus early transcription stop sequence (TTTTTNT), (iii) Ecogpt expression cassette under the control of a vaccinia early/late promoter and terminating in the poxvirus early transcription stop sequence (TTTTTNT); (iv) the peanut hypoallergen vaccine antigen expression cassette (UBc.PHAVag or PHAVag) as described above, (v) 500 bp right homologous recombination arm that flanks down-stream of the VACV-A39R ORF of the Copenhagen strain. A diagrammatic presentation of these cassettes can be found in FIG. 4 and their DNA sequences can be found in FIGS. 6 and 7.

Figure 8A:
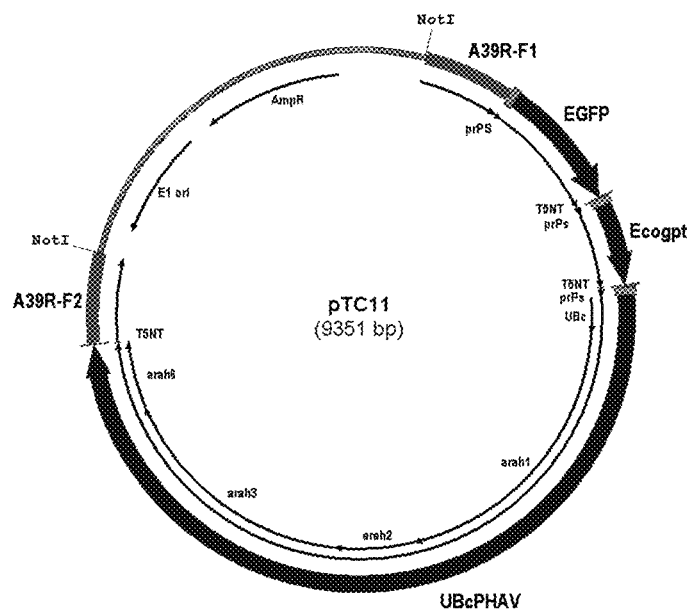
FIG. 8A is a diagrammatic representation of the pTC11 (UBc.PHAV) plasmid
Figure 8B:
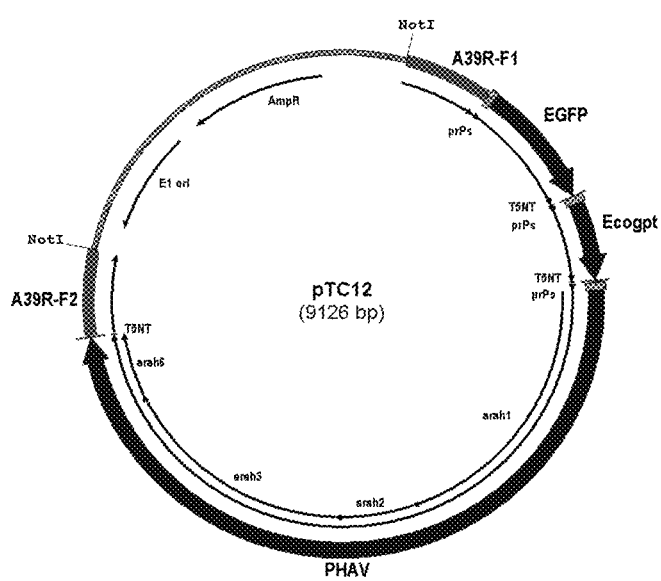
FIG. 8B is a diagrammatic representation of the pTC12 (PHAV) plasmid. The plasmids are shown in FIG. 8.

Both UBc.PHAV and PHAV homologous recombination cassettes were flanked with Not I restriction enzyme sites and cloned into plasmids to form clones pTC11 (UBc.PHAV) and pTC12 (PHAV). The plasmids are shown in FIG. 8. As these cassettes were synthetically made, any TTTTTNT sequences occurring with the protein coding sequences of EGFP and Ecogpt where disrupted with silent mutations without affecting the encoded amino acid sequences.

Figure 4A:
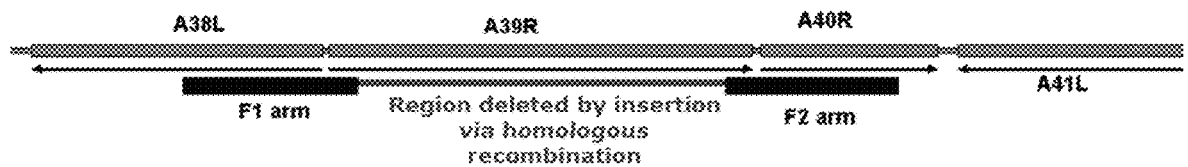
FIGS. 4a, 4B and 4C are diagrammatic representations of the insertion of the PHAV expression cassettes into the A39R ORF of vaccinia virus Copenhagen strain by homologous recombination.
Figure 4B:
Figure 4C:

Construction of Vaccinia Virus Expressing the Peanut Hypoallergen Vaccine Antigens:

The PHAV expression cassettes were inserted into the A39R ORF of vaccinia virus Copenhagen strain by homologous recombination. FIG. 4 shows a map illustrating site of the insertion within the A39R ORF. Briefly, this was carried out by infecting BHK21 cells at a low multiplicity of infection (moi) of 0.01 pfu per cell for 45 minutes and then transfecting the cells with either of the Not I linearized pTC11 or pTC12 plasmid vectors. The infected/transfected cells were then harvested once the infection reach near completion. Harvested cells were then sonicated to make viral extracts and these virus extracts where subjected to one round of plaque purification under positive selection with Mycophenolic acid (MPA) in the presence of xanthine, hypoxanthine, aminopterin and thymidine. Plaque purified clones where then sequentially amplified under MPA positive selection to make a seed stock of virus. Recombinant vaccinia virus harbouring the UBc.PHAVag expression cassette was designated as SCV201C and the recombinant virus harbouring the PHAVag expression cassette was designated SCV202C.

Detailed protocols for making recombinant vaccinia virus using Ecogpt selection method can be found in Smith 1993. The method employed to make SCV201C and SCV202C is outlined below.

Homologous Recombination:

For each virus construction, three T25 flasks containing growth medium (RPMI-1640/10% FCS/2 mM Glutamax/Pen-Strep) were seeded with BHK21 cells and culture until subconfluent at 37° C./5% $CO_2$. On the day of infection, two flasks were infected with VACV-COP at an moi 0.01 pfu/cell, where the other flask was not infected (uninfected control). After infecting flask 1 and 2 for 45 min at room temperature, the virus inoculums were removed and the monolayer of cells washed twice with PBS. After washing, 4 ml of Maintenance Medium (MM: RPMI-1640/2% FCS/2 mM Glutamax/Pen-Strep) was added to each flask including Flask 3 that had also gone through the same washing step.

Transfection was carried out using Effectene Transfection reagent (Qiagen, Cat No 301425) and following the manufacturer's instructions. Briefly, 16 μL of Enhancer was added to 2 μg of linearized pTC11 or pTC12 in 150μμL of EC buffer and left to stand for 5 minutes at room temperature after thoroughly mixing. To this 25 μl of Effectene Transfection reagent was added, thoroughly mixed and left to stand at room temperature for 10 minutes. Finally, 1 ml of MM (RPMI-1640/2% FCS/2 mM Glutamax/Pen-Strep) was added mixed thoroughly mixed gently together. This transfection mix was then added to flask 1 that had previously been infected with VACV-COP.

Flask 1 (homologous recombination), Flask 2 (infection only control) and Flask 3 (uninfected control) were incubated overnight at 37° C./5% $CO_2$ where the following day each flask had a media change with fresh MM containing 25 μg/mL mycophenolic acid (MPA), 250 μg/mL xanthine and $1^x$ HAT (Sigma Cat #H0262-10VL)—5 mL per flask and further incubated at 37° C./5% $CO_2$ until gross CPE can be seen in Flask 1 only. There was little or no sign of gross CPE in Flask 2 as the MPA treatment inhibited VACV-COP spread of infection, and the monolayer looked healthy in Flask 3.

Cells in Flask 1 were harvested by scraping the cells into the culture medium, then pelleted by low speed centrifugation (500 g for 5 minutes at room temperature) followed by resuspending the cell pellet in 1 mL of 10 mM Tris-HCl pH8. A viral extract was prepared by multiple freeze and thaw cycles and then stored at −80° C. ready for plaque purification phase. The viral constructs were designated SCV201C (UBc.PHAV insertion) and SCV202C (PHAV insertion).

Plaque Purification Process:

The homologous recombination extract was serially diluted and each dilution was used to infect one row of BHK21 cells cultured in a 48 well plate in the presence of MPA. The aim was to dilute the virus down to 1 pfu infection per well and look for wells that contain only 1 fluorescent plaque after approx. 30 hr of infection before harvesting.

BHK21 cells were seeded into each well of a 48-well plate and culture to 100% in growth medium (RPMI-1640/10% FBS/2 mM Glutamax/pen-strep) at 37° C./5% $CO_2$. Thereafter the medium was replaced with MM containing 25 μg/mL MPA, 250 μg/mL xanthine and $1^x$ HAT (Sigma Cat #H0262-10VL) and incubated further overnight.

For infection, the homologous recombination extracts (SCV201C and SCV202C) were thawed and briefly sonicated to break up lumps and aggregates. Tenfold serial dilution down to $10^{-5}$ of each viral extract was performed using MM (RPMI/2% FBS/Glutamax/PenStrep) in 1 mL volumes. For each dilution, one row of the 48-well plate was seeded with 100 μL of diluted virus after removing the growth medium from each well and washed once with PBS. The 48-well plate was left at room temperature for 45 minute for viral adsorption to occur. After viral adsorption, the virus inoculum was carefully removed from each well where residual inoculum was removed by a washing step consisting of 500 μL of PBS per well. After washing, 500 μL of MM (RPMI/2% FBS/Glutamax/PenStrep) containing 25 μg/mL MPA, 250 μg/mL xanthine and $1^x$ HAT (Sigma Cat #H0262-10VL) was added to each well and then incubated at 37° C./$CO_2$ until fluorescent green foci of infections could be clearly seen under a fluorescent microscope.

For harvesting, only wells containing a single fluorescent foci at the highest dilution possible was selected. The medium from selected wells were carefully removed and 100 μL of 10 mM TrisHCl pH8 was added. The plate was freeze-thawed three times and the contents of the selected wells were recovered.

One selected clone was then further amplified by infecting 1 well of a 6-well plate containing BHK21 cells at 100% confluency that had been pretreated overnight with 25 μg/mL MPA, 250 μg/mL xanthine and $1^x$ HAT (Sigma Cat #H0262-10VL), by removing the culture medium from the well and adding 10 μL of viral extract diluted to 500 μL in PBS. After 45 min at room temperature 2 mL of MM containing 25 μg/mL MPA, 250 μg/mL xanthine and $1^x$ HAT (Sigma Cat #H0262-10VL) was added to the well and incubated further at 37° C./5% $CO_2$ for 3 days until majority of the cells fluoresced green under a fluorescent microscope. The cells within the infected well were scraped into the culture medium and then pelleted at 500 g for 5 minutes. The pelleted cells were resuspended in 500 μL of 10 mM TrisHCl pH8 and briefly sonicated to make a viral extract.

A portion of this extract was used for further amplification by infecting five T175 flask of BHK21 under MPA selection. The infected cells were recovered and then pelleted at 500 g for 5 mins. The pelleted cells for all five flasks were resuspended in 5 mL of 10 mM TrisHCl pH8 and briefly sonicated to make a viral extract. Insoluble material was then remove by pelleting at 500 g for 5 min. The supernatant (viral extract) was then titrated in BHK21 cells using the following procedure outlined below and the presence of the inserted UBc.PHAV within the A39R ORF was confirmed by PCR analysis.

Titration:

Titration was carried out using 24-well plate format. Plaques were clearly distinguishable as Crystal violet counter-stained holes in the monolayer (plaques), as seen by the naked eye.

For each recombinant virus to be titrated, one 24 well plate was seeded with BHK21 cells and cultured to confluency in growth medium (RPMI/10% FBS/Glutamax/Pen Strep). On the day of titration, each viral stock was thawed and sonicated to break up lumps and clumps. Each virus was serially diluted in PBS down to $10^{-8}$. The medium was removed from each well and starting from the $10^{-8}$ dilution, 500 μL of each dilution was added to each well of a column in the 24 well plate (4 wells per dilution) and left to incubate at room temperature for 45 mins for the virus to adsorb to the cells. After this, the virus inoculum was removed from each well, where each well was then washed once with PBS. After washing, 1 mL of MM (RPMI/2% FBS/Glutamax/PenStrep) was added to each well and the plates were incubated at 37° C./5% $CO_2$ until plaques can been seen in the monolayers. For plaque counter staining, the medium from each well was removed and 500 μL of Crystal Violet solution (0.4% w/v in 20% ethanol) was added to each well. Staining was carried out at room temperature for 15-30 min where after the Crystal Violet stain was removed from each well and each well left to air dry before counting plaques. From the dilution that gave rise to 10-30 counts per well, the mean was calculated. This value was then multiplied by the reciprocal of the serial dilution and then further multiplied by 2 (i.e., 2×500 μL=1 mL) to produce the titre in pfu/mL.

Immunogenicity Testing of SCV201C in C3H/HeJ Mice:

To test the immunogenicity of SCV201C and determine if the ubiquitinated PHAV antigen can induce a peanut protein specific $T_H1$ immune response 3 groups of C3H/HeJ mice (5 mice per group) where vaccinated with the following: (i) $10^6$ pfu of SCV201C administered intraperitoneally (IP), (ii) $10^6$ pfu of SCV000 administered intraperitoneally (IP), and (iii) PBS administered intraperitoneally (IP). Blood samples were taken just prior to vaccination (prebleed) and 17 days after vaccination. Spleens for cytokine profiling was harvested 9 weeks are vaccination.

Preparation of Soluble Peanut Protein Extract:

The method used to extract soluble peanut protein from roasted unsalted peanuts was derived from the procedures described by Sachs et al. (1981) and Burks et al. (1992). Roasted unsalted peanuts were purchased from a local grocery store. The nuts were then pulverized in a blender to a meal and then to a butter paste. Lipids/fats were removed from the peanut butter by the additions of de-fatting reagent hexane. To do this, n-hexane was added to the peanut butter and shaken vigorously to mix. The mixture was transferred to a glass beaker and left to settle into solvent and solid phases. The solvent phase (which contains the extracted lipids/fats) was removed from the solid phase. The solid phase was air dried into a cake. This cake was dissolved in 0.1M $NH_4HCO_3$ (2 mL per gram) at 4° C. for 36 hours with stirring to extract soluble proteins. The slurry was centrifuged for 15 min at 10,000 g to remove solids. The supernatant was dialyzed against 5 mM phosphate buffer (pH7 to pH8) or PBS using 3500 MWCO membrane/tubing. The dialyzed solution was centrifuge at 10,000 g for 15 min at 4° C. to clarify the extract. Total protein concentration in the soluble extract was measured using standard techniques. The resulting soluble protein extract (10 mg/ml) was kept at −20° C. for storage, and thawed prior to use.

Quantification of Peanut-Specific Serum IgE and IgG2a:

Flat-bottom 96-well EIA/RIA ELISA plates (Costar) were coated with 2 μg/well purified peanut extract in PBS and incubated at 37° C. for 1 hr then overnight at 4° C. Plates were washed with 200 μl/well PBS three times before blocking with 5% skim milk with PBS and 0.05% Tween (SM+PBS+TW). Non-specific binding was blocked at 37° C. for at least one hour before three 200 μl/well washes with PBS with 0.05% Tween (PBS+TW). After washing, serum samples were first diluted 1:100 for IgE assays, or 1:500 for IgG1 and IgG2a assays, in SM+PBS+TW. Serum samples were serially diluted across three columns. Various wells were left without serum as background controls. The plates were incubated at 37° C. for one hour.

Plates were washed five times with 2000 of PBS and secondary antibody (1:500 Goat antimouse IgE HRP conjugate, Alpha Diagnostic; 1:1000 HRP rat anti-mouse IgG2a, BD Biosciences-BD Pharmingen) diluted in SM+PBS+TW was added (100 μl/well). The plates were incubated for one hour and then washed five times as above, and 1000/well of o-Phenylenediaminedihydrochloride (OPD) substrate solution prepared according to manufacturer's directions (SigmaFAST™ OPD, Sigma-Aldrich) was added. Reactions were stopped with 20 μl/well 1MHCl when colour had begun to develop in 'blank' wells (ranging from five minutes in IgG1 and IgG2a assays to 45 minutes for IgE assay). Optical densities were measured at 450 nm on a plate reader (EL808 Ultra Microplate Reader, Bio-tek Instruments Inc).

Optical densities for serial dilutions from each respective time point were plotted against dilution factor on a logarithmic scale using GraphPadPrisim V5.01 (GraphPad Software, San Diego, Calif., USA). The endpoint titre for each time point was determined as the dilution value at which the curve intercepted the calculated cut-off optical density (minimum of three times standard errormean (SEM) of pre-bleed samples but greater than the highest optical density value measured for all pre-bleed samples).

Statistical Analyses:

Statistical comparisons were performed using GraphPad Prism V5.01 (GraphPad Software, San Diego, Calif., USA). Two-way analysis of variance (ANOVA) with Bonferroni post-testing was used to deduce significant differences among the ELISA results.

Example 1

Ubiquitination of PHAV Antigen Enabled the Successful Expression of SCV201C but not SCV202C The expression of SCV201C following insertion of the UBc.PHAVag expression cassette into the A39R of vaccinia virus was successful. After homologous recombination and during the plaque purification step, MPA resistant plaques could be clearly identify and amplified in the presence of MPA to produce a seed stock that gave sufficient titres to proceed to the next step of immunogenicity testing in mice.

By contrast, the expression of SCV202C was difficult to progress beyond the plaque purification step, as no clearly discernable plaques could be found at the high dilution range. Fluorescent infected cells could be detected at the low dilution range and at these dilution only 100% CPE was seen in the infected wells as opposed to discernable plaques.

When these wells were harvested and subjected to further amplification in the presence of MPA, very little virus titre was obtained most of which consisted of parental virus as determined by PCR analysis and plaque assays showing the lack of fluorescent plaque in the absence of MPA.

The expression of PHAVag following infection had an inhibitory or toxic effect on virus propagation, which was overcome with the SCV201C construct. Without being bound by theory or by a particular mode of application, it is postulated that the inhibitory or toxic effect of the synthesized PHAVag was overcome by the use of a proteasome degradation tag such as ubiquitin to target the expressed PHAVag to proteasomal degradation.

This inhibitory effect of viral propagation by expressing the intact PHAVag was further confirmed because the construction a recombinant vaccinia containing only the Ecogpt and EFGP expression cassettes inserted into the A39R ORF was easily achievable (designated as SCV000).

Example 2

Antigen-Specific Antibody Responses Following Vaccination

Figure 10A:
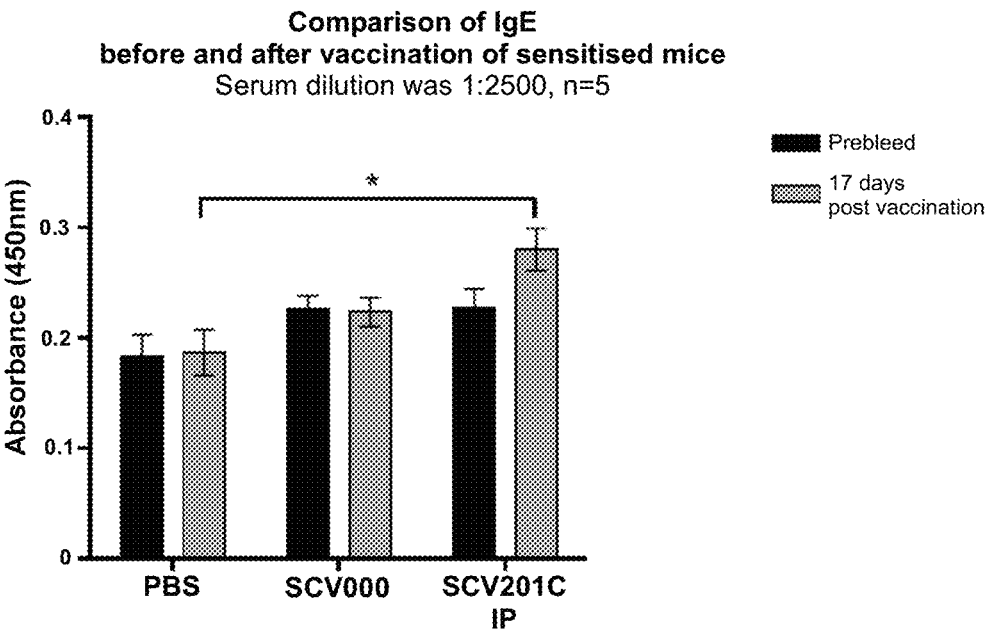
FIGS. 10A and 10B show the levels of peanut protein-specific serum IgE (FIG. 10A) and IgG2a (FIG. 10B) antibodies before and after vaccination (17 day post vaccination) with the empty vector (SCV000) or the UBc.PHAV vector (SCV201C); *p<0.05.
Figure 10B:
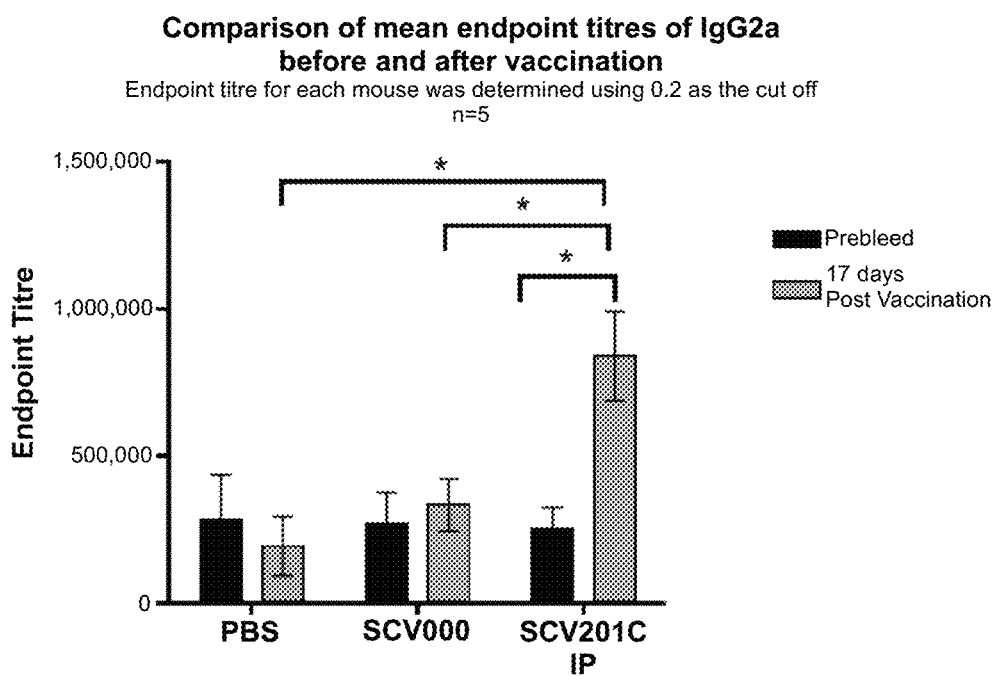

The results are present in FIG. 10 for both peanut protein-specific serum IgE (FIG. 10A) and IgG2a (FIG. 10B) antibody level before and after vaccination (17 day post vaccination). It can be clearly seen that vaccination with SCV201C produced significant levels of peanut protein-specific IgG2a after 17 day post vaccination. These level where significantly higher than the vector only control (SCV000) and PBS control, demonstrating SCV201C produces a specific anti-peanut protein antibody response. It is to be noted that SCV201C produced a much smaller IgE response as compared to an IgG2a response; that is, an endpoint dilution of 1:2,500 for IgE as compared to an endpoint dilution approaching 1:1,000,000 for IgG2a. Moreover, the IgE response was not much more above the responses induced by the empty vector (SCV000) or PBS controls.

These results show that SCV201C produces an IgG2a response to peanut proteins, but very little IgE response, indicating that SCV201C had initiated a peanut-specific $T_H1$ biased immune response in response to PHAVag.

Example 3

Lymphocyte Cytokine Profile Following SCV201C Vaccination in Mice

Spleens were harvested from mice and stored in complete RPMI before being transferred to a 60 mm tissue culture dish. Spleens were then cut into three sections and disaggregated into single-cell suspension. The cells were then filtered and washed with 5% RPMI (300 g×5 minutes). Red blood cells were then lysed in 5 ml of alkaline lysis buffer for 5 minutes, then diluted to 20 ml with 5% RPMI and centrifuged at 200 g for 5 minutes. Cells were then resuspended and counted. Meanwhile, 96-well plates with control RPMI, soluble peanut-antigen (100 μg/ml), and ConA (5 ug/ml) wells were prepared. Lymphocytes were then add at 400,000 cells/well and incubated at 37 C for 96 hours.

After the 96 hour incubation period, 100 μl of supernatant from each was collected and frozen at −80° C. Th1/Th2 cytokines were then quantified by flow cytometry according to the manufacturer's instructions (BD Biosciences #551287). The samples were then run on a BD FACSCanto II flow cytometer. Cytokine concentrations were determined using Soft Flow FCAP Array software. All further analysis was done in Graph Pad 6.0.

Figure 11A:
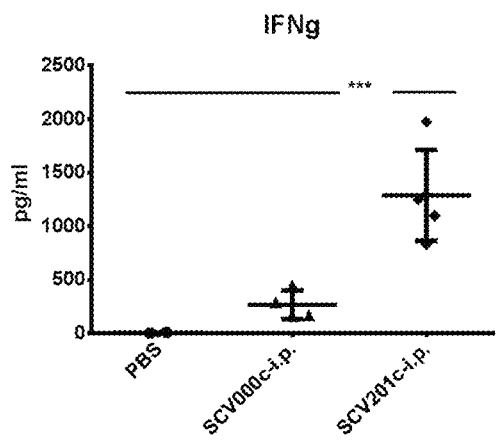
FIG. 11A), IL4 ($T_H2$ cytokines.
Figure 11B:
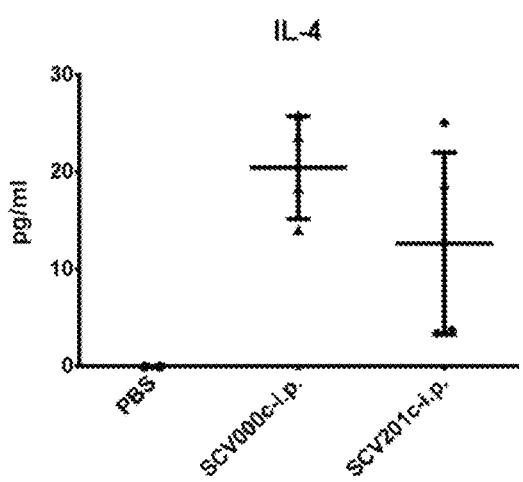
FIG. 11B) and IL5 ($T_H2$ cytokines.
Figure 11C:
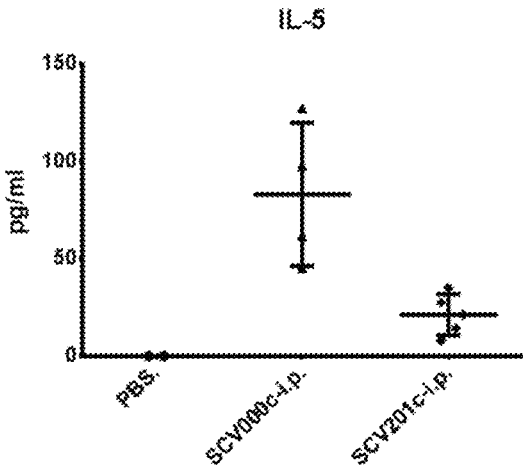
FIG. 11C) secreted by cultured lymphocytes obtained from the spleens of SCV000 and SCV201C vaccinate mice.

The results presented in FIG. 11 clearly show that vaccination with SCV201C produces a biased $T_H1$ immune response to peanut protein exposure. This is illustrated by the significantly higher level of IFN-gamma (IFN-g; a $T_H1$ cytokine; FIG. 11A) as compared to levels of IL4 and IL5 ($T_H2$ cytokines; FIGS. 11B and 11C) secreted by cultured lymphocytes obtained from the spleens of the SCV201C vaccinate mice.

CONCLUSION

Vaccination of mice with SCV201C produced a biased anti-peanut protein $T_H1$ immune response. An allergen-specific $T_H1$ immune response will dominate over an existing allergen-specific $T_H2$ immune response and, in doing so, will desensitize an individual to subsequent exposure to the allergen. The studies disclosed herein show that ubiquitinated peanut hypoallergen vaccine antigen (UB-c.PHAVag) stimulates an anti-peanut protein-specific $T_H1$ immune response. Thus, vaccines containing the ubiquitinated hypoallergen vaccine antigen as herein described can be used to desensitize individuals to peanut allergens and can therefore be used to treat and/or prevent allergic reactions in individuals that are triggered by exposure to peanut allergens.

As noted above, the expression of the SCV201C construct was successful following infection, whereas the expression of the non-ubiquitinated SCV202C construct was difficult to progress beyond the plaque purification step. The expression of PHAVag following infection therefore appears to have an inhibitory or toxic effect on virus propagation, which was overcome with the ubiquitinated SCV201C construct. Without being bound by theory or by a particular mode of application, it is postulated that the inhibitory or toxic effect of the synthesized PHAVag was overcome by the use of ubiquitin, targeting the expressed PHAVag to proteasomal degradation. As a result of ubiquitin-targeted proteasomal degradation of PHAVag, the small peptide fragments of PHAVag enter the endoplasmic reticulum (ER) where they are complexed with MHC class I proteins and then transported to the cell surface to be presented to T lymphocytes (see, for example, FIG. 9). The consequence of this is that there is enhanced presentation of the PHAVag fragments with MHC class I, resulting in a greater $T_H1$ immune response to peanut allergens. Thus, the proteasome degradation tag (e.g., ubiquitin) unexpectedly prevent the artificial, intact PHAVag fusion protein from inhibiting virus replication.

Ara h 1, ara h 2, ara h 3 are the three major peanut allergens that have been shown to cause peanut-specific allergic reactions in susceptible individuals. Ara h 6 has been implicated in childhood susceptibility to peanut allergy (Flinterman et al. 2007). Ara h 7 is recognised in 43% peanut allergic individuals, ara h 8 is recognised in 85% peanut allergic individuals, ara h 4 is recognised in 54% peanut allergic individuals and ara h 5 is recognised in 13% peanut allergic individuals.

The disclosure of every patent, patent application, and publication cited herein is hereby incorporated herein by reference in its entirety.

Many modifications will be apparent to those skilled in the art without departing from the scope of the present invention.

BIBLIOGRAPHY

Burks W A, Williams L W, Connaughton C, Cockrell G, O'Brien T J, Helm R M., 1992. Identification and characterization of a second major peanut allergen, Ara h II, with use of the sera of patients with atopic dermatitis and positive peanut challenge. J. Allergy Clin. Immunol., 90: 962-969.

DeLong J H, Simpson K H, Wambre E, James E A, Robinson D, Kwok W W. 2011. Ara h 1-reactive T cells in individuals with peanut allergy. J. Allergy Clin. Immunol. 127 (5): 1211-1218.e3.

Dudek T, Knipe D M. 2006. Replication-defective viruses as vaccines and vaccine vectors. Virology 344 (1): 230-239.

Flinterman A E, van Hoffen E, den Hartog Jager C F, Koppelman S, Pasmans S G, Hoekstra M O, Bruijnzeel-Koomen C A, Knulst A C, Knol E F. 2007. Children with peanut allergy recognize predominantly Ara h2 and Ara h6, which remains stable over time. Clin Exp Allergy. 37(8):1221-8.

Heath W R, Carbone F R. 1999. Cytotoxic T lymphocyte activation by cross-priming. Curr. Opin. Immunol. 11 (3): 314-318.

Hartl A, Kiesslich J, Weiss R, Bernhaupt A, Mostbock S, Scheiblhofer S, Ebner C, Ferreira F, Thalhamer J. 1999. Immune responses after immunization with plasmid DNA encoding Bet v 1, the major allergen of birch pollen. J Allergy Clin. Immunol. 103: 107-13.

Hartl A, Hochreiter R, Stepanoska T, Ferreira F, Thalhamer J. 2004. Characterization of the protective and therapeutic efficiency of a DNA vaccine encoding the major birch pollen allergen Bet v 1a. Allergy 59: 65-73.

Holgate S T. 1999. The epidemic of allergy and asthma. Nature 402 (6760 Suppl), B2-B4

Hsu C H, Chua K Y, Tao M H, Lai Y L, Wu H D, Huang S K, Hsieh K H. 1996. Immunoprophylaxis of allergen-induced immunoglobulin E synthesis and airway hyperresponsiveness in vivo by genetic immunization. Nat. Med. 2 (5): 540-544.

Jilek S, Barbey C, Spertini F, Corthesy B. 2001. Antigen-independent suppression of the allergic immune response to bee venom phospholipase A(2) by DNA vaccination in CBA/J mice. J. Immunol. 166: 3612-21.

Kumaraguru U, Rouse R J, Nair S K, Bruce B D, Rouse B T. 2000. Involvement of an ATP-dependent peptide chaperone in cross-presentation after DNA immunization. J. Immunol. 165 (2): 750-759.

Leitner W W, Hammerl P, Thalhamer J. 2001. Nucleic acid for treatment of cancer: genetic vaccines and DNA adjuvants. Curr. Pharm. Des. 7(16): 1641-1667.

Long A. 2002. The nuts and bolts of peanut allergy. N. Engl. J. Med. 346 (17): 1320-1322.

Lu Z, Yuan L, Zhou X, Sot E, Levitsky H I, Pardoll D M. 2000. CD4040-independent pathways of T cell help for priming of CD8(+) cytotoxic T lymphocytes. J. Exp. Med. 191 (3): 541-550.

Mosmann T R, Coffman R L. 1989. TH1 and TH2 cells: different patterns of lymphokine secretion lead to different functional properties. Annu. Rev. Immunol. 7: 145-173.

Oppenheimer J J, Nelson H S, Bock S A, Christenson F, Leung D Y. 1992. Treatment of peanut allergy with rush immunotherapy. J. Allergy Clin. Immunol. 90 (2): 256-262.

Parronchi P, Maggi E, Romagnani S. 1999. Redirecting Th2 responses in allergy. Curr. Top. Microbiol. Immunol. 238: 27-56.

Polo J M, Dubensky T W Jr. 2002. Virus-based vectors for human vaccine applications. Drug Discov. Today 7 (13): 719-727.

Raz E, Tighe H, Sato Y, Corr M, Dudler J A, Roman M, Swain S L, Spiegelberg H L, Carson D A. 1996. Preferential induction of a Th1 immune response and inhibition of specific IgE antibody formation by plasmid DNA immunization. Proc. Natl. Acad. Sci. USA. 93 (10): 5141-5145.

Ridge J P, Di Rosa F, Matzinger P. 1998. A conditioned dendritic cell can be a temporal bridge between a CD4+ T-helper and a T-killer cell. Nature 393 (6684): 474-478.

Rocha C D, Caetano B C, Machado A V, Bruna-Romero O. 2004. Recombinant viruses as tools to induce protective cellular immunity against infectious diseases. Int. Microbiol. 7 (2): 83-94.

Roy K, Mao H Q, Huang S K, Leong K W. 1999. Oral gene delivery with chitosan—DNA nanoparticles generates immunologic protection in a murine model of peanut allergy. Nat. Med. 1999; 5: 387-91.

Sachs M I, Jones R T, Yunginger J W. 1981. Isolation and partial characterization of a major peanut allergen. J. Allergy Clin. Immunol., 67: 27-34.

Sanderson I R, Walker W A. 1993. Uptake and transport of macromolecules by the intestine: possible role in clinical disorders (an update). Gastroenterology 104 (2): 622-639.

Shaheen S O, Aaby P, Hall A J, Barker D J, Heyes C B, Shiell A W, Goudiaby A. 1996. Measles and atopy in Guinea-Bissau. Lancet 347 (9018): 1792-1796.

Sicherer S H, and Leung D Y. 2010. Advances in allergic skin disease, anaphylaxis, and hypersensitivity reactions to foods, drugs, and insects in 2009. J Allergy Clin. Immunol. 125 (1), 85-97.

Singh V K, Mehrotra S, Agarwal S S. 1999. The paradigm of Th1 and Th2 cytokines: its relevance to autoimmunity and allergy. Immunol. Res. 20 (2): 147-161.

Slater J E, Colberg-Poley A. 1997. A DNA vaccine for allergen immunotherapy using the latexallergen Hey b 5. Arb. Paul Ehrlich Int. Bundesamt Sera ImpfstoffeFrankf. A. M. 91: 230-235.

Smith G L. 1993. Expression of genes by vaccinia virus vectors. In Molecular Virology: A practical approach. Edited by A J Dawson and R M Elliott. IRL Press at Oxford University Press, Oxford UK.

Spiegelberg H L, Orozco E M, Roman M, Raz E. 1997. DNA immunization: a novel approach to allergen-specific immunotherapy. Allergy 52 (10): 964-970.

Srivastava K D, Qu C, Zhang T, Goldfarb J, Sampson H A, Li X M. 2009. Food allergy herbal formula-2 silences peanut-induced anaphylaxis for a prolonged posttreatment period via IFN-gamma-producing $CD8^+$ T cells. J. Allergy Clin. Immunol. 123 (2), 443-451.

Toda M, Sato H, Takebe Y, Taniguchi Y, Saito S, Inouye S, Takemori T, Sakaguchi M. 2000. Inhibition of immunoglobulin E response to Japanese cedar pollen allergen (Cry j 1) in mice by DNA immunization: Different outcomes dependent on the plasmid DNA inoculation method. Immunology 99: 179-86.

Turcanu V, Stephens A C, Chan S M, Rance F, Lack G. 2010. IgE-mediated facilitated antigen presentation underlies higher immune responses in peanut allergy. Allergy 65 (10), 1274-1281.

deVries J E, Carballido J M, Aversa G. 1999. Receptors and cytokines involved in allergic TH2 cell responses. J. Allergy Clin. Immunol. 103 (5 Pt 2), S492-S496.

The invention claimed is:

1. A vaccinia virus vector comprising a nucleic acid sequence encoding a fusion protein, comprising:
   (i) a proteasome degradation tag to enhance intracellular degradation of the fusion protein; and
   (ii) peanut allergens:
   ara h 1 comprising the sequence of amino acids set forth as SEQ ID NO:4,
   ara h 2 comprising the sequence of amino acids set forth as SEQ ID NO:6,
   ara h 3 comprising the sequence of amino acids set forth as SEQ ID NO:8, and
   ara h 6 comprising the sequence of amino acids set forth as SEQ ID NO:10,
   wherein the fusion protein, when expressed from the vector and degraded, results in T-cell epitope-containing peptides that can complex with MHC class I proteins for presentation to T lymphocytes to produce a biased $T_H1$ immune response to the T-cell epitope containing peptides.

2. The vaccinia virus vector of claim 1, wherein the vector comprises a promoter and single start codon to facilitate expression of the intact fusion protein.

3. The vaccinia virus vector of claim 1, wherein the fusion protein comprises the amino acid sequence set forth in SEQ ID NO: 12.

4. The vaccinia virus vector of claim 1, wherein the vector comprises the nucleic acid sequence set forth in SEQ ID NO: 11.

5. The vaccinia virus vector of claim 1, wherein the only peanut allergens in the fusion protein are:
   ara h 1 comprising the sequence of amino acids set forth as SEQ ID NO:4,
   ara h 2 comprising the sequence of amino acids set forth as SEQ ID NO:6,
   ara h 3 comprising the sequence of amino acids set forth as SEQ ID NO:8, and
   ara h 6 comprising the sequence of amino acids set forth as SEQ ID NO:10.

6. The vaccinia virus vector of claim 1, wherein the vector is a modified vaccinia virus vector.

7. A medicament, comprising:
   the vaccinia virus vector of claim 1; and
   a pharmaceutically or physiologically acceptable carrier and/or diluent.

8. A method of inducing tolerance to a peanut allergen or suppressing an allergic response to a peanut allergen in a subject or patient, the method comprising administering to the subject or patient an effective amount of the vaccinia virus vector of claim 1 for a time and under conditions sufficient to elicit tolerance to a peanut allergen or suppression of an allergic response to a peanut allergen.

9. A method of vaccinating a subject to induce tolerance to a peanut allergen, comprising administering the vaccinia virus vector of claim 1 to the subject.

10. The method of claim 8, wherein the vaccinia virus vector induces tolerance to, or suppresses an allergic response to, ara h 1, ara h 2, ara h 4 and ara h 6.

11. A kit, comprising the vaccinia virus vector of claim 1.

12. The method of claim 8, wherein the subject or patient is a human.

13. The method of claim 12, wherein the nucleic acid sequence encoding the fusion protein is codon optimized for expression in human cells.

14. A poxvirus vector, comprising a nucleic acid sequence encoding a fusion protein that comprises the amino acid sequence set forth in SEQ ID NO:12.

15. A vaccinia virus vector, comprising a nucleic acid sequence encoding a fusion protein comprising:
 (i) a proteasome degradation tag to enhance intracellular degradation of the fusion protein; and
 (ii) only the following four peanut allergens:
 ara h 1 comprising the sequence of amino acids set forth as SEQ ID NO:4, ara h 2 comprising the sequence of amino acids set forth as SEQ ID NO:6, ara h 3 comprising the sequence of amino acids set forth as SEQ ID NO:8, and ara h 6 comprising the sequence of amino acids set forth as SEQ ID NO:10,
 wherein the fusion protein, when expressed from the vector and degraded, results in T-cell epitope-containing peptides that can complex with MHC class I proteins for presentation to T lymphocytes to produce a biased $T_H1$ immune response to the T-cell epitope containing peptides.

\* \* \* \* \*